(12) United States Patent
Kostrzewski

(10) Patent No.: US 10,251,646 B2
(45) Date of Patent: Apr. 9, 2019

(54) SURGICAL STAPLING APPARATUS

(71) Applicant: Covidien LP, Mansfield, MA (US)

(72) Inventor: Stanislaw Kostrzewski, Newtown, CT (US)

(73) Assignee: Covidien LP, Mansfield, MA (US)

( * ) Notice: Subject to any disclaimer, the term of this patent is extended or adjusted under 35 U.S.C. 154(b) by 682 days.

(21) Appl. No.: 14/918,720

(22) Filed: Oct. 21, 2015

(65) Prior Publication Data

US 2016/0038144 A1 Feb. 11, 2016

Related U.S. Application Data

(63) Continuation of application No. 14/567,331, filed on Dec. 11, 2014, now Pat. No. 9,237,890, which is a continuation of application No. 13/274,497, filed on Oct. 17, 2011, now Pat. No. 8,931,679.

(51) Int. Cl.
| | | |
|---|---|---|
| A61B 17/068 | (2006.01) | |
| A61B 17/072 | (2006.01) | |
| A61B 17/29 | (2006.01) | |
| A61B 17/10 | (2006.01) | |
| A61B 17/00 | (2006.01) | |

(52) U.S. Cl.
CPC ...... *A61B 17/07207* (2013.01); *A61B 17/068* (2013.01); *A61B 17/105* (2013.01); *A61B 17/2909* (2013.01); *A61B 2017/00367* (2013.01); *A61B 2017/00473* (2013.01); *A61B 2017/07228* (2013.01); *A61B 2017/07271* (2013.01); *A61B 2017/07278* (2013.01); *A61B 2017/2923* (2013.01)

(58) Field of Classification Search
CPC ............ A61B 17/07207; A61B 17/068; A61B 17/105; A61B 17/2909; A61B 2017/00367; A61B 2017/00473; A61B 2017/07278; A61B 2017/07271
USPC ........................................................ 227/175.1
See application file for complete search history.

(56) References Cited

U.S. PATENT DOCUMENTS

| | | | |
|---|---|---|---|
| 3,650,453 | A | 3/1972 | Smith, Jr. |
| 3,717,294 | A | 2/1973 | Green |
| 3,837,555 | A | 9/1974 | Green |
| 4,951,860 | A | 8/1990 | Peters et al. |
| 7,954,683 | B1 | 6/2011 | Knodel et al. |
| 7,963,432 | B2 | 6/2011 | Knodel et al. |

(Continued)

FOREIGN PATENT DOCUMENTS

| | | |
|---|---|---|
| EP | 0156774 A2 | 10/1985 |
| WO | 2010/054404 A1 | 5/2010 |

*Primary Examiner* — Michelle Lopez

(57) ABSTRACT

A surgical stapler includes an anvil assembly and a cartridge assembly. The anvil assembly defines staple forming depressions. One or both of the anvil assembly and the cartridge assembly are pivotable relative to the other between an open position and a clamped position. The cartridge assembly includes a first plurality of staples and a second plurality of staples. The first plurality of staples is initially positioned in alignment with the staple forming depressions of the anvil assembly for ejection from the cartridge assembly. The second plurality of staples is movably supported in the cartridge assembly from a first position misaligned with the staple forming depressions of the anvil assembly to a second position aligned with the staple forming depressions for subsequent ejection from the cartridge assembly.

20 Claims, 53 Drawing Sheets

(56) References Cited

U.S. PATENT DOCUMENTS

| | | | |
|---|---|---|---|
| 7,988,026 B2 * | 8/2011 | Knodel | A61B 17/072 227/175.1 |
| 8,931,679 B2 * | 1/2015 | Kostrzewski | A61B 17/07207 227/175.1 |
| 9,237,890 B2 * | 1/2016 | Kostrzewski | A61B 17/07207 |

* cited by examiner

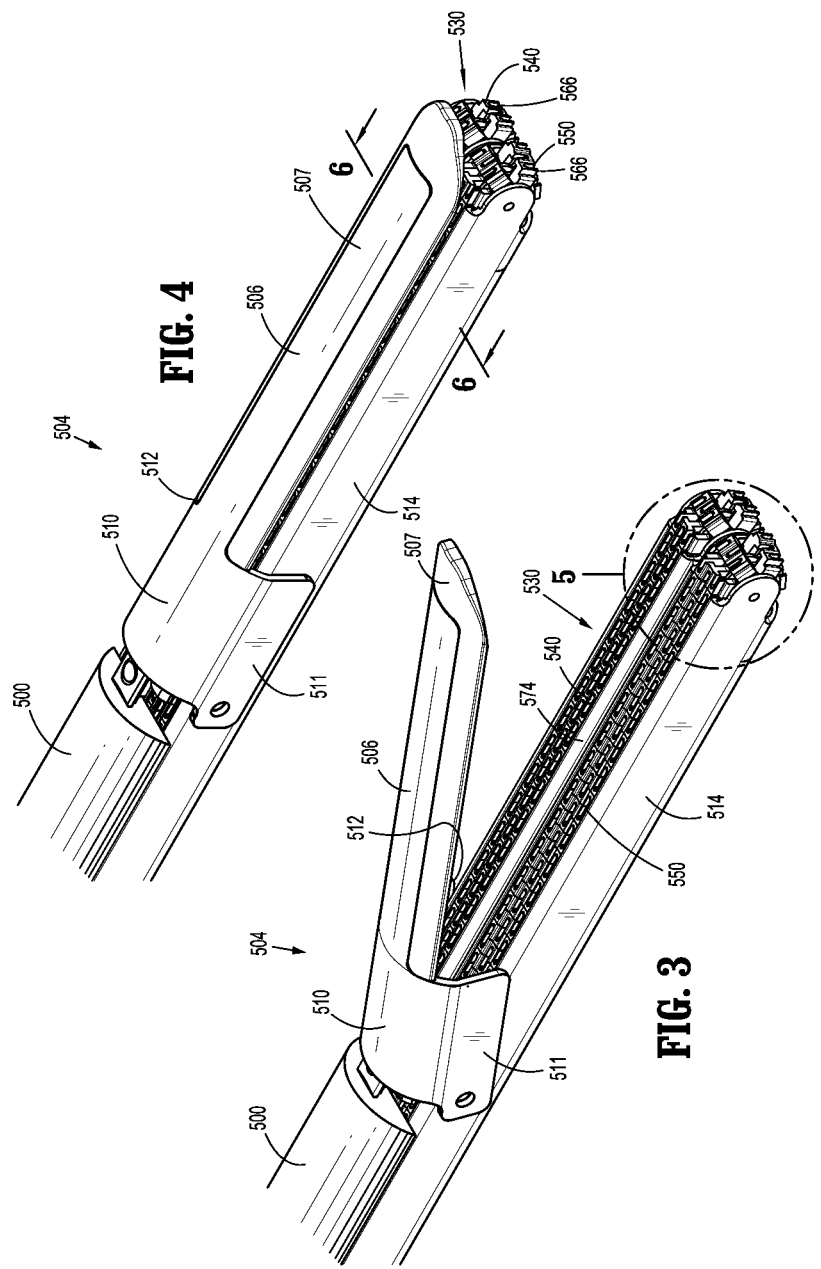

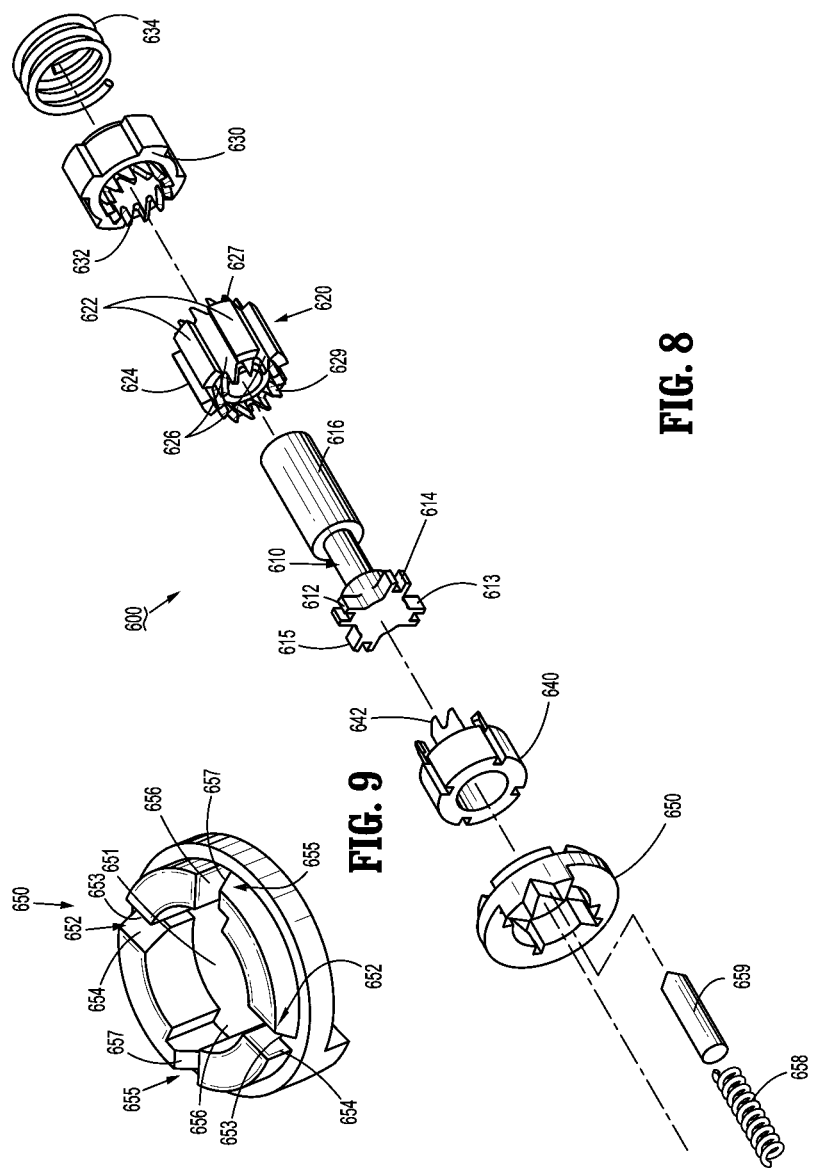

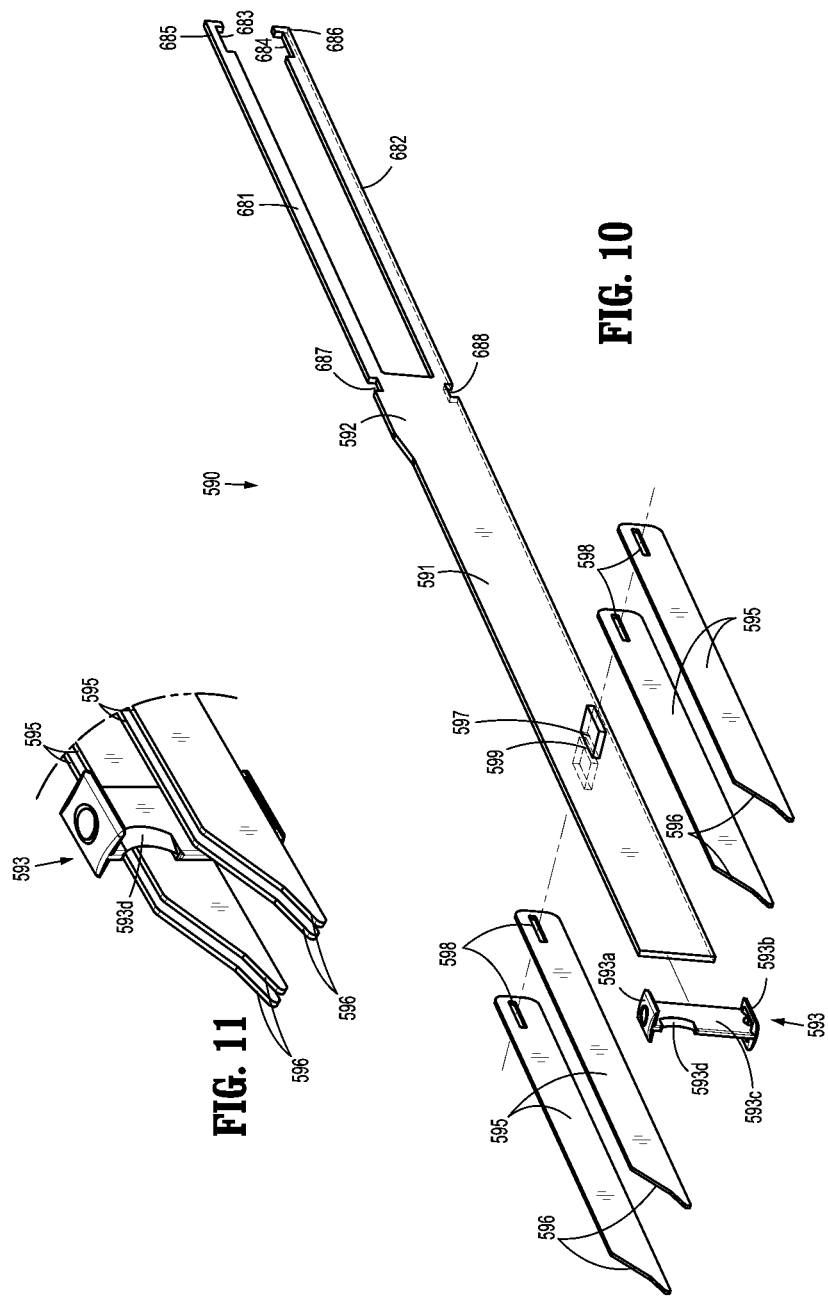

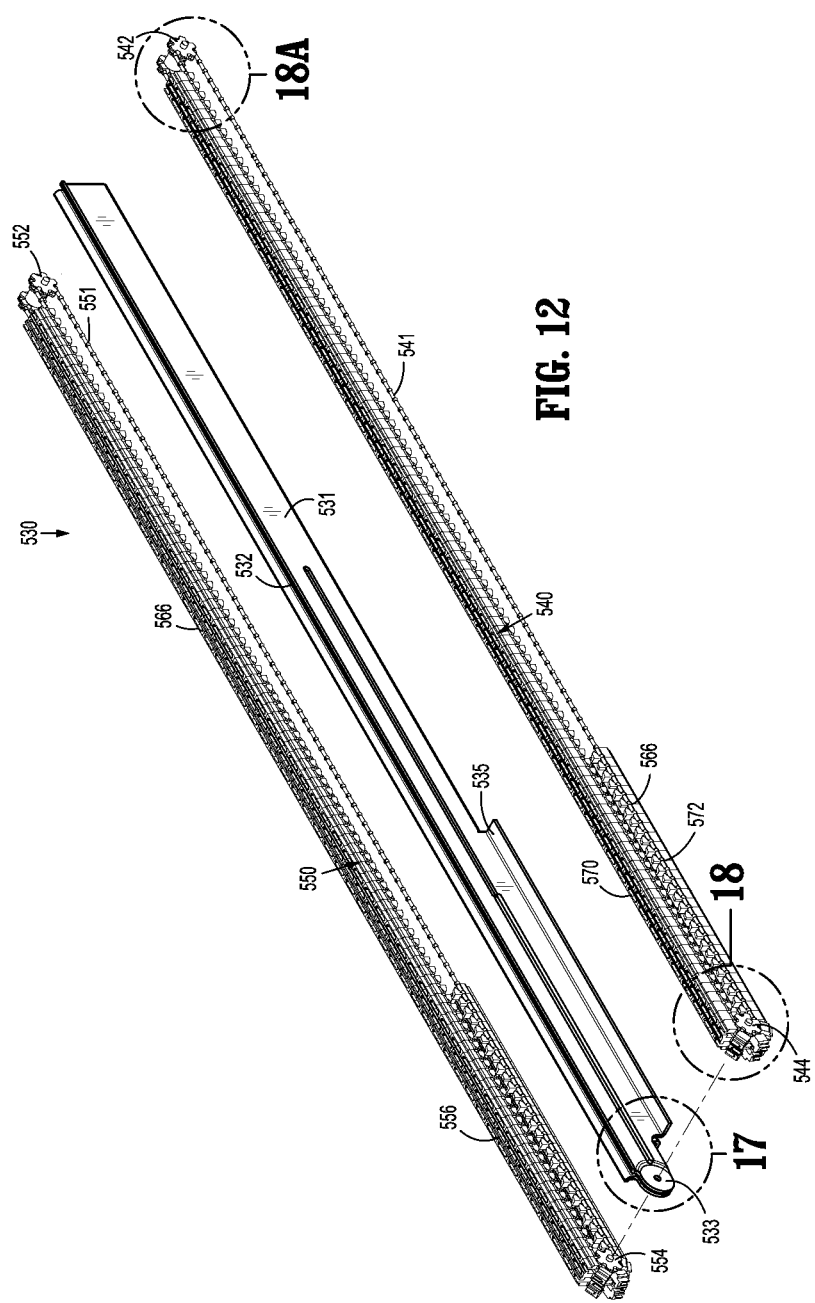

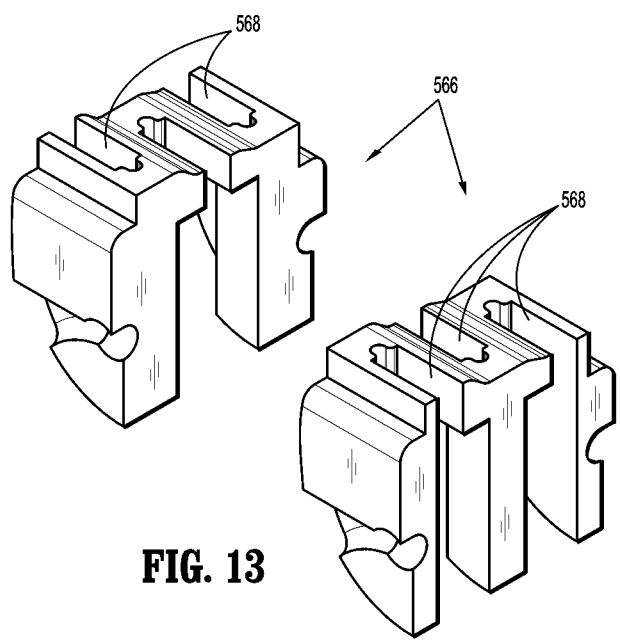
FIG. 13
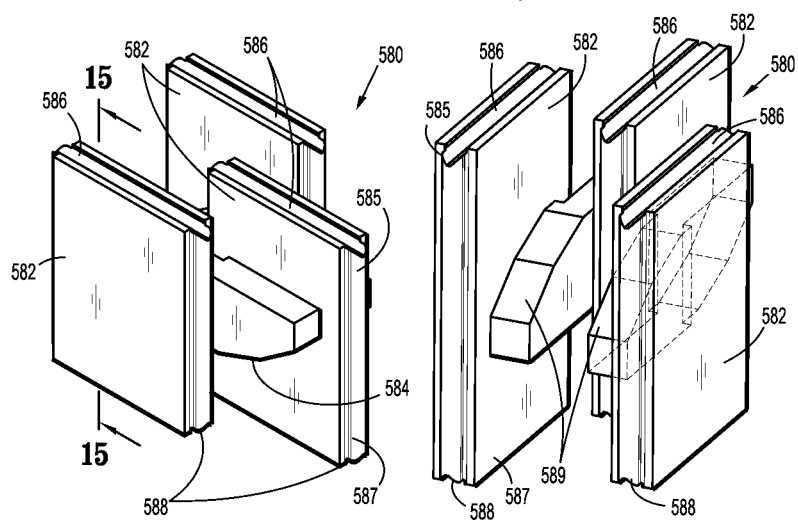
FIG. 14  FIG. 14A

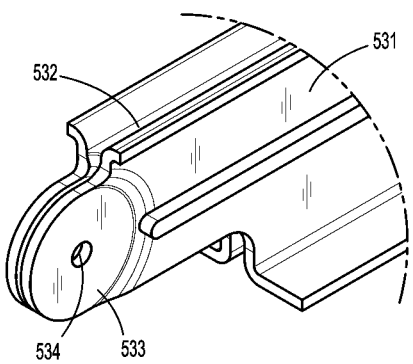
FIG. 17
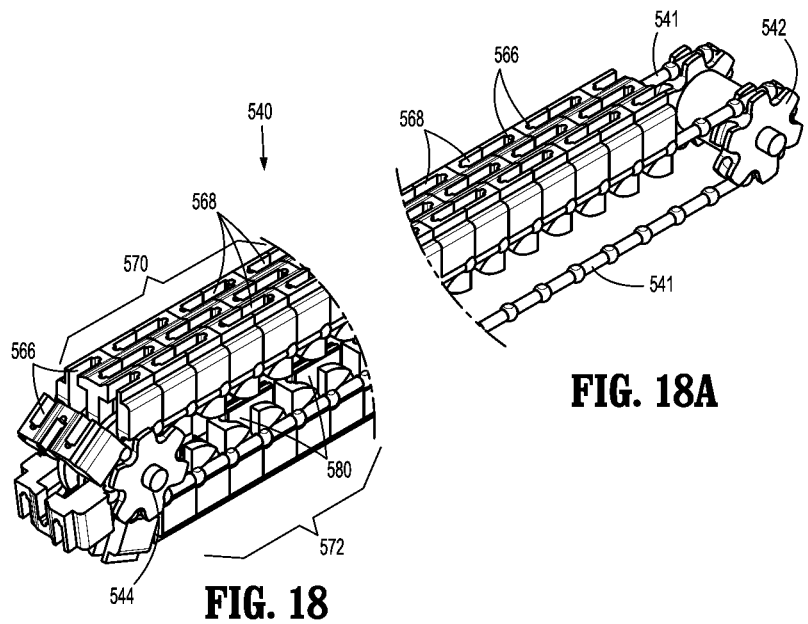
FIG. 18A
FIG. 18

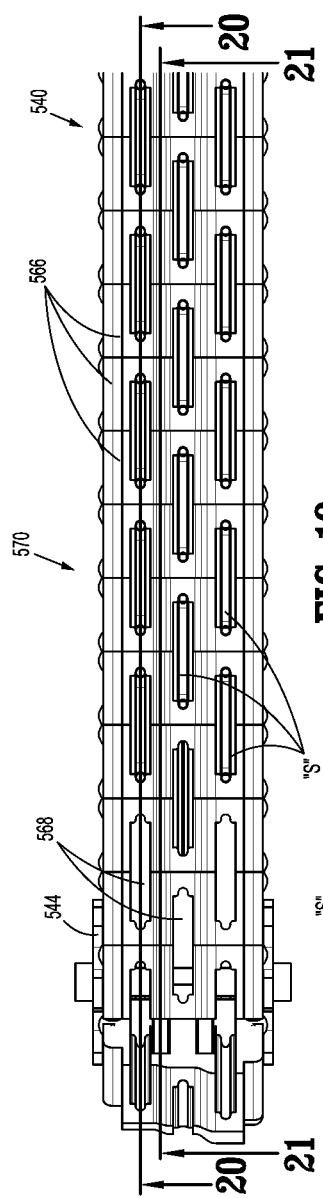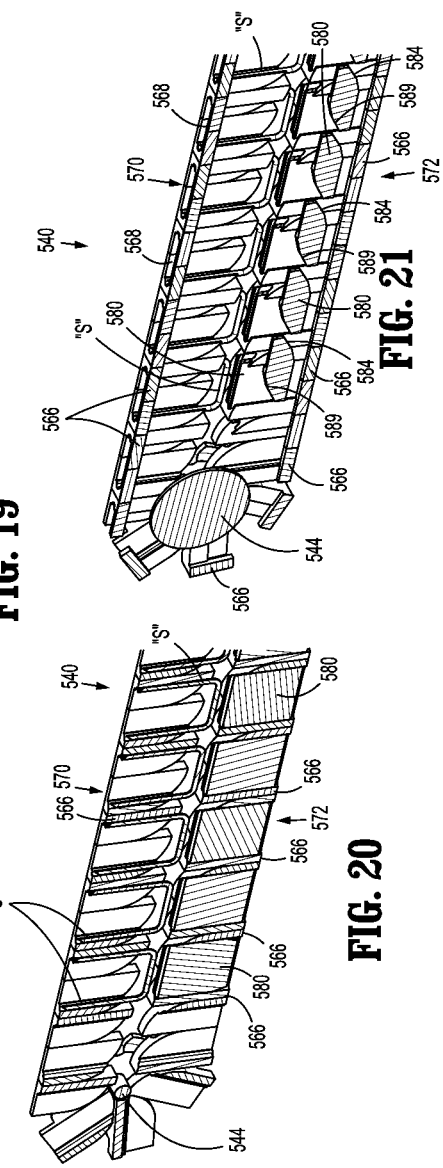

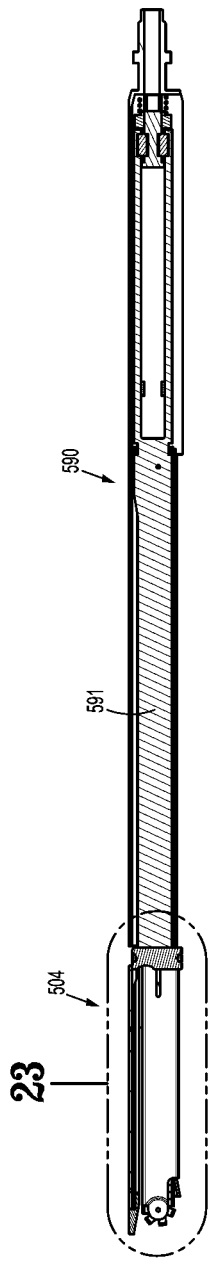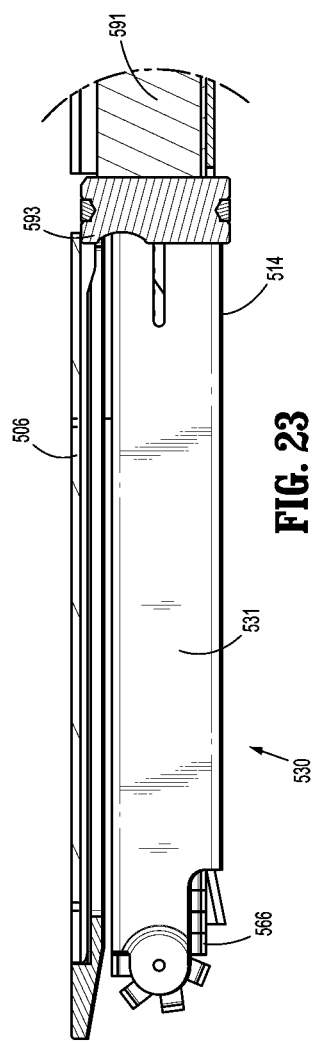
FIG. 22
FIG. 23

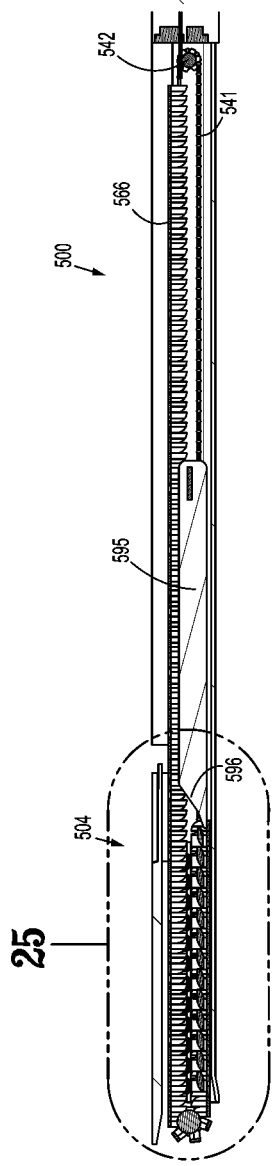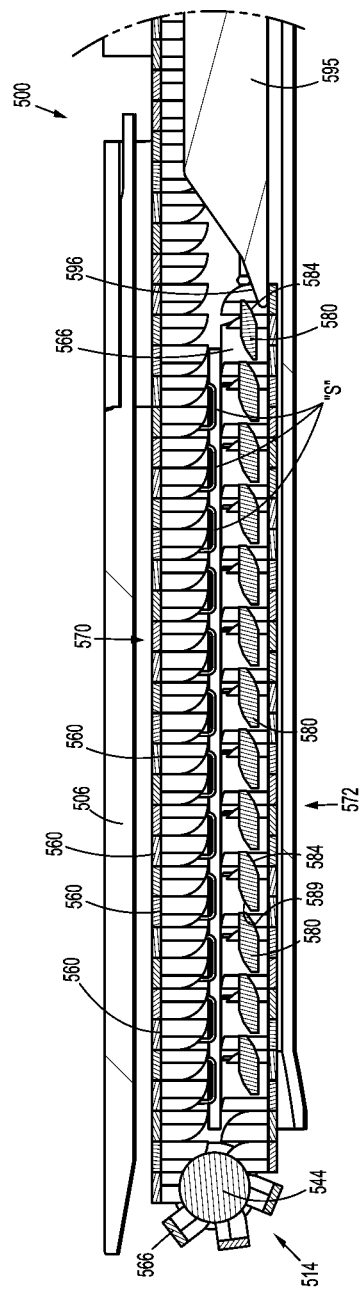
FIG. 24
FIG. 25

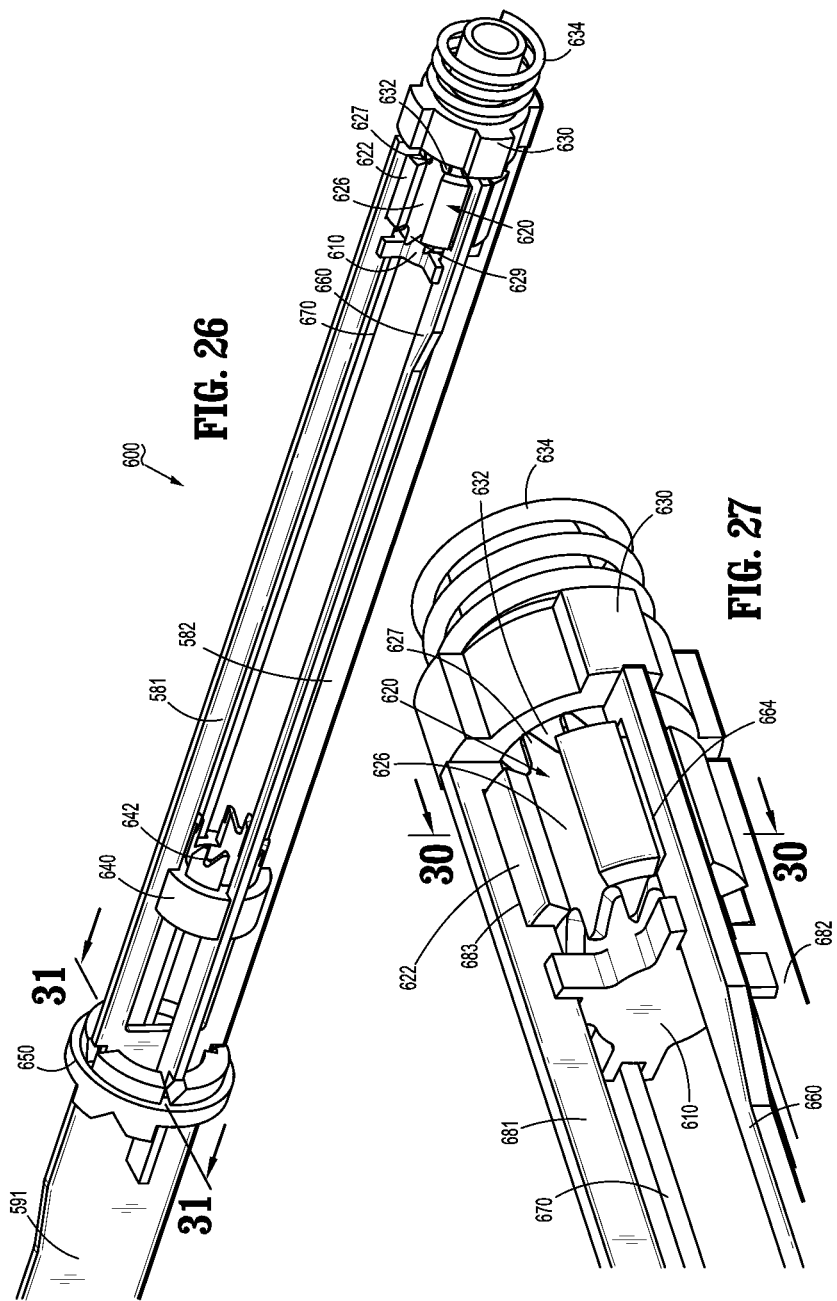

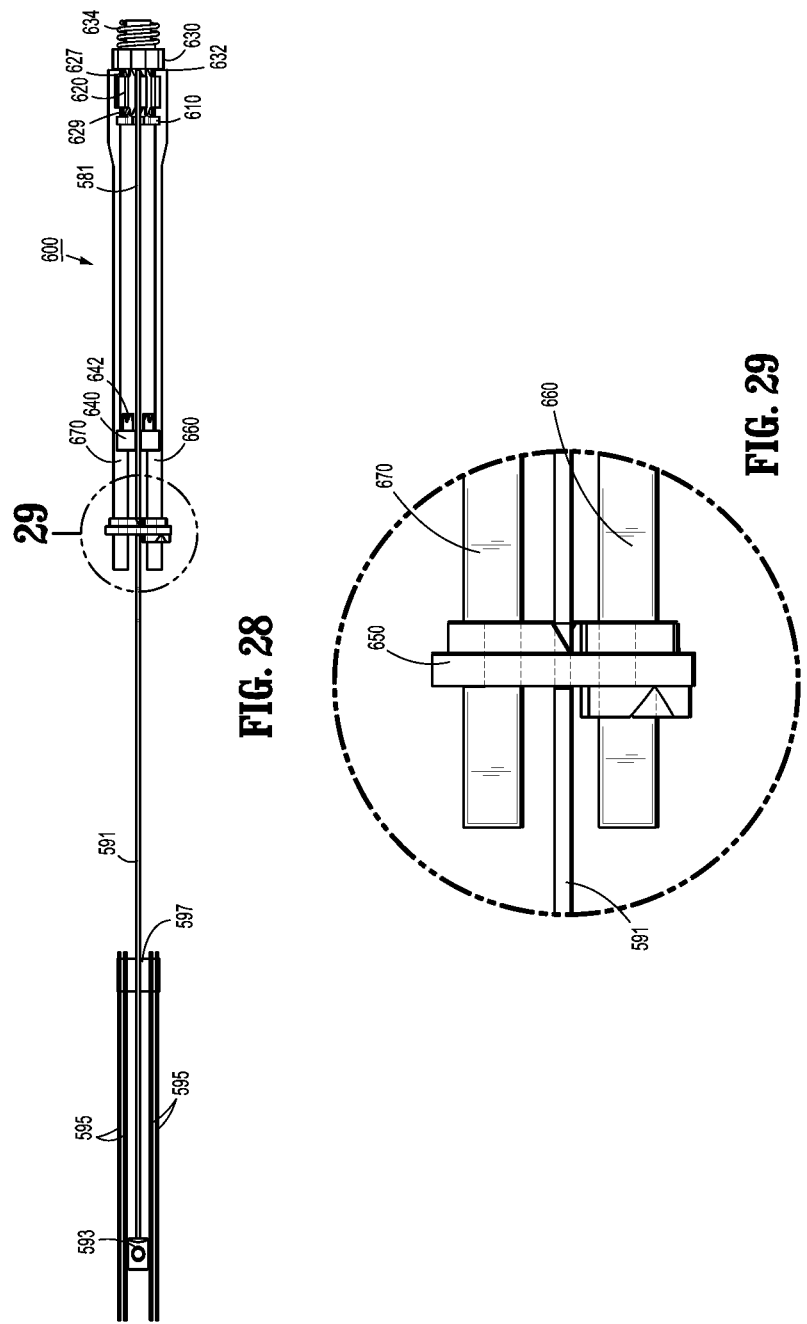

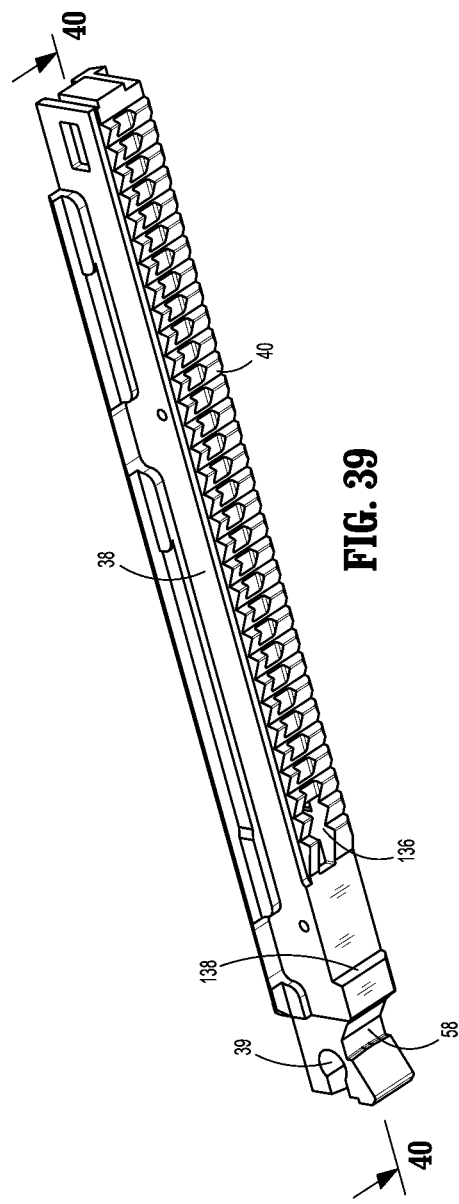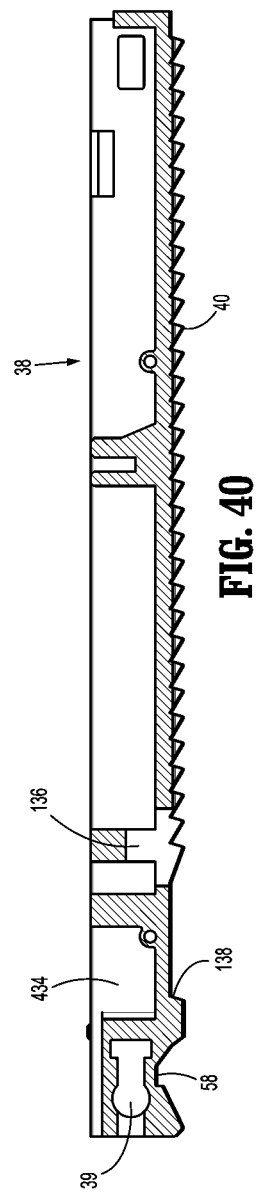
FIG. 39
FIG. 40

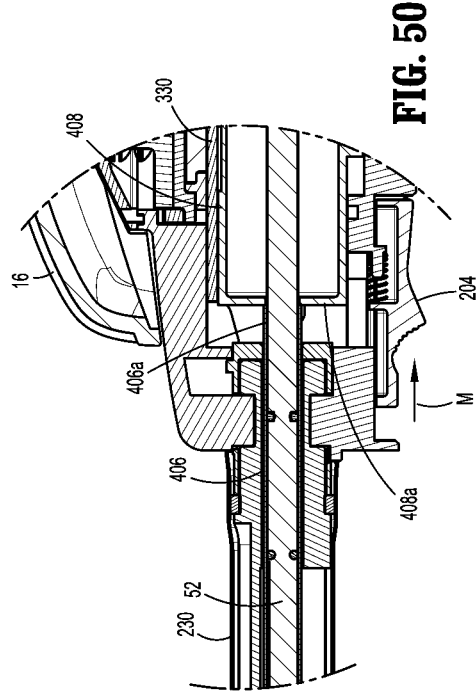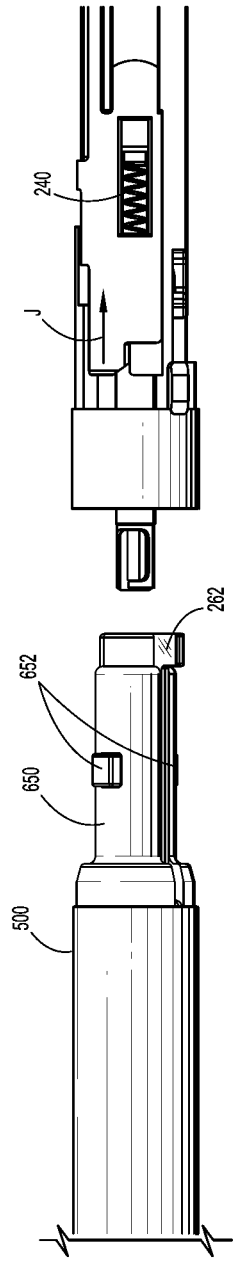

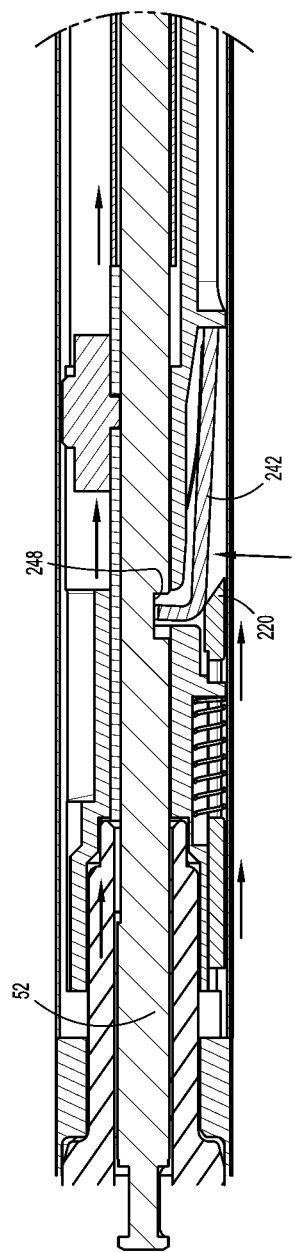
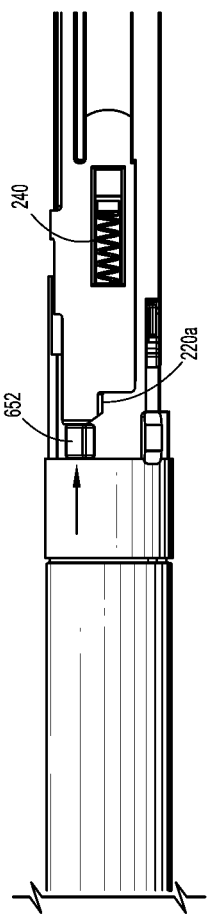
FIG. 54
FIG. 55

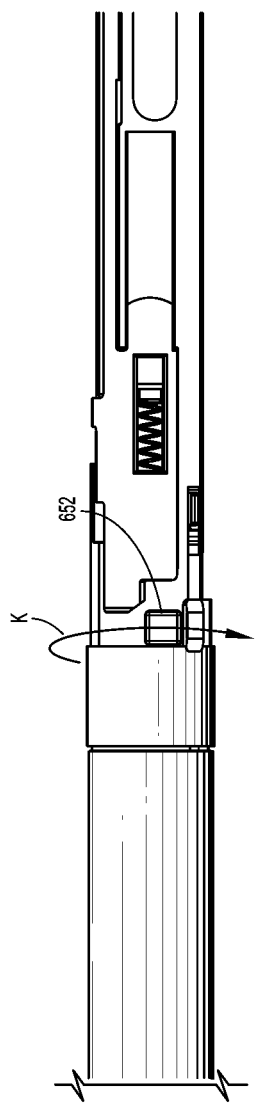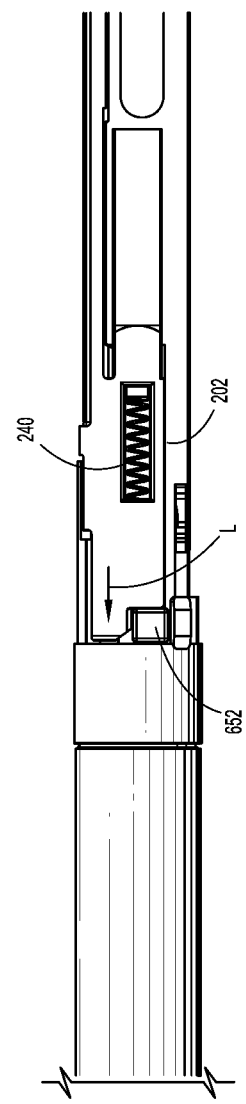

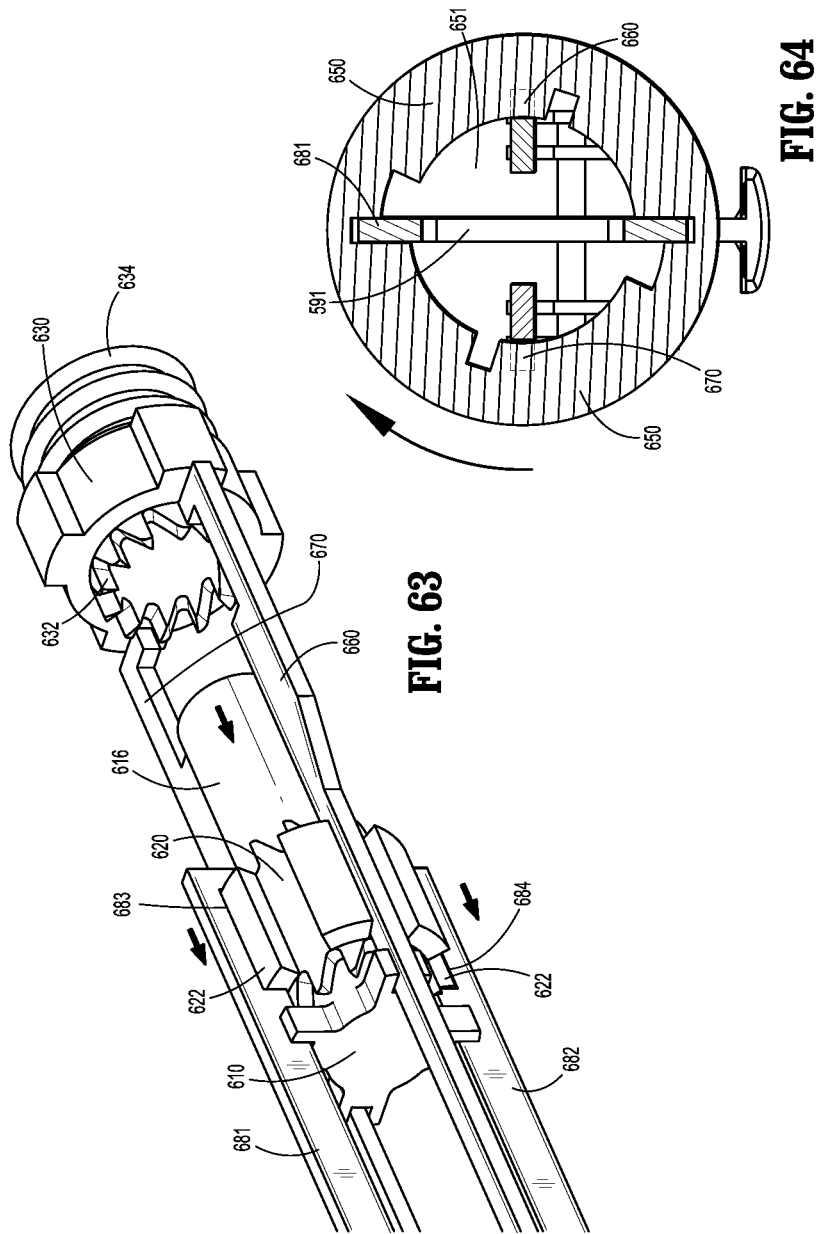

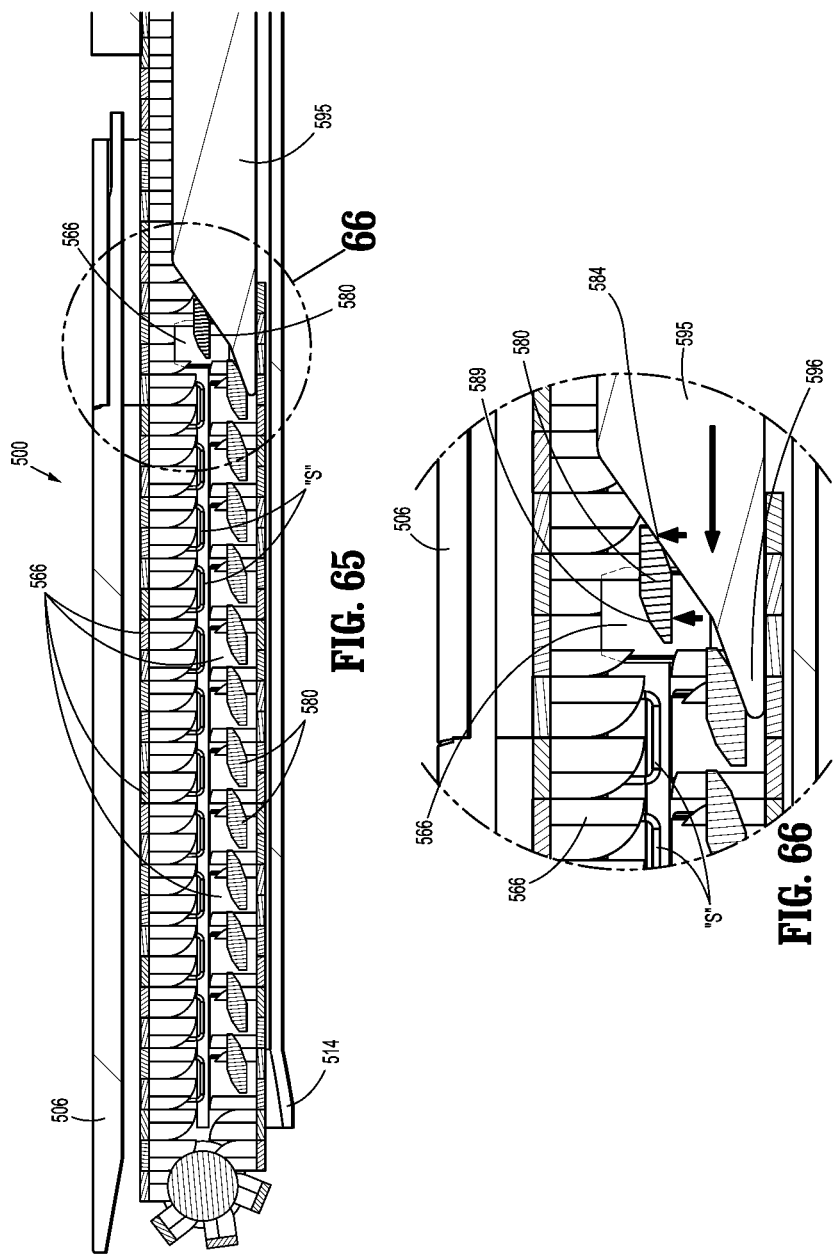

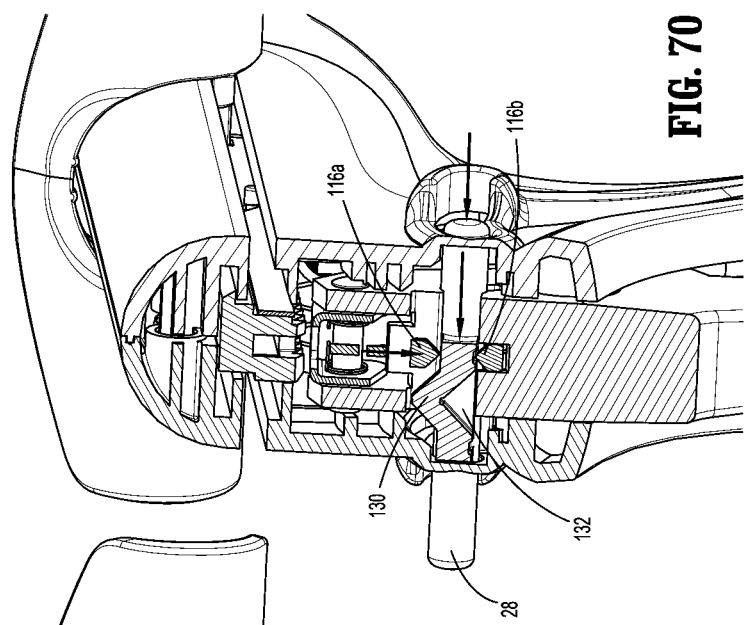
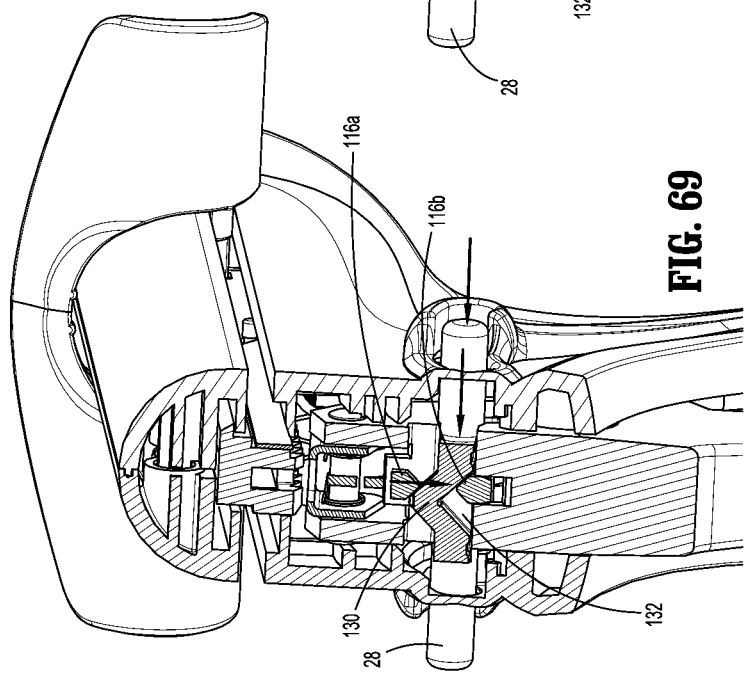

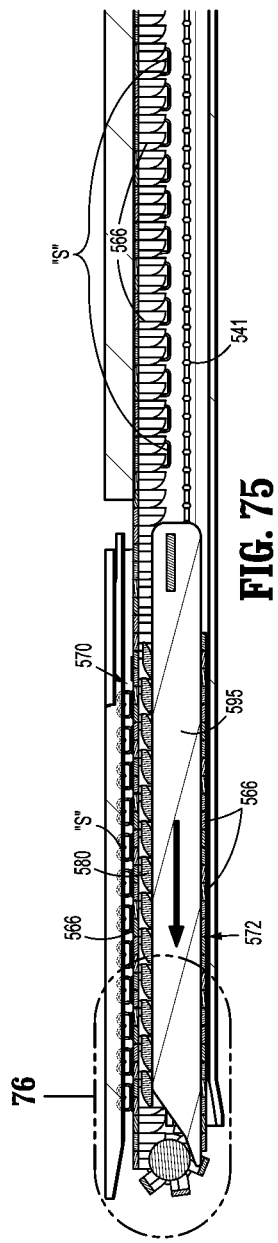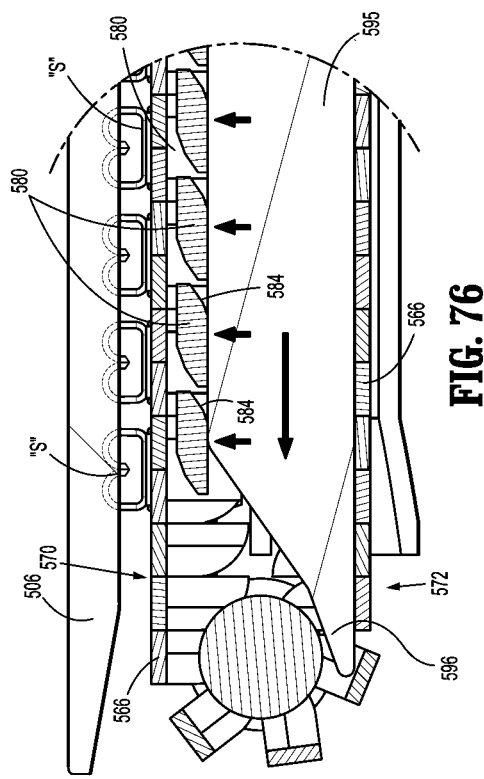

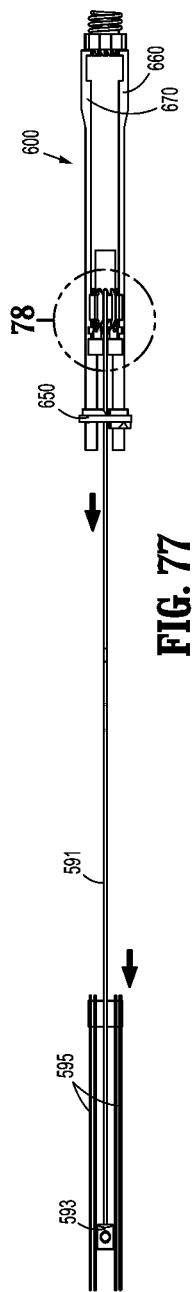
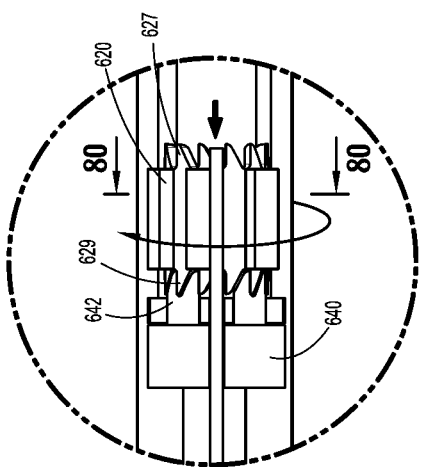
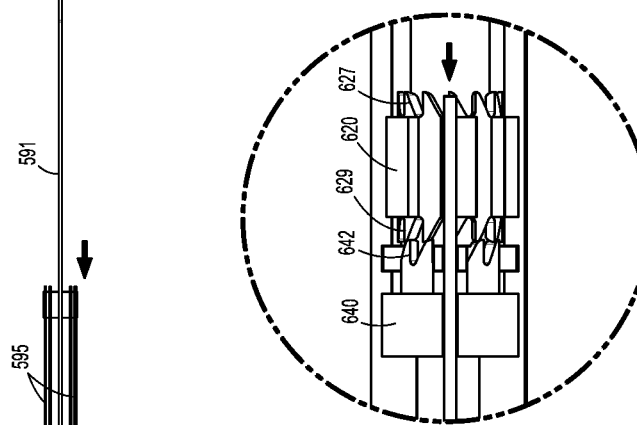
FIG. 77
FIG. 78
FIG. 79

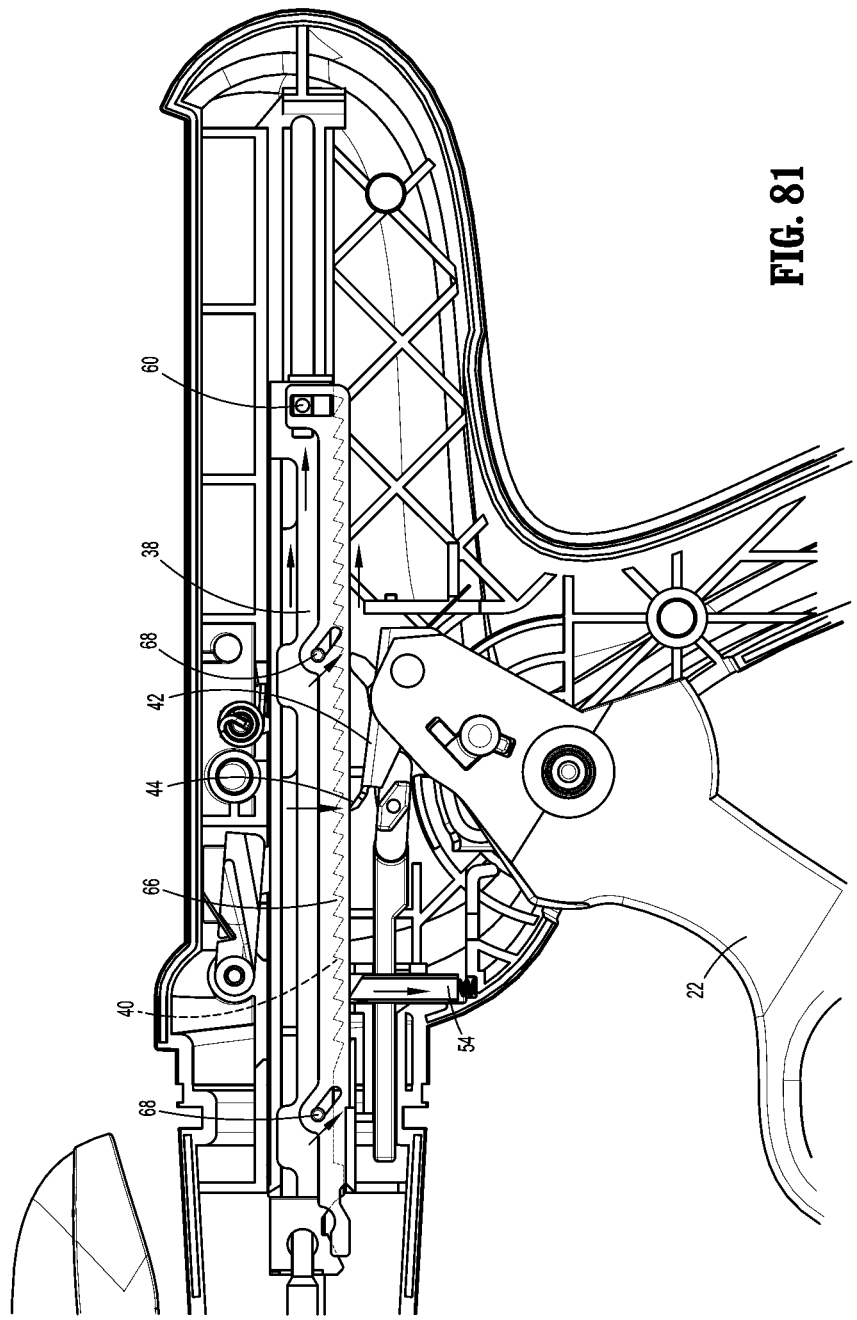

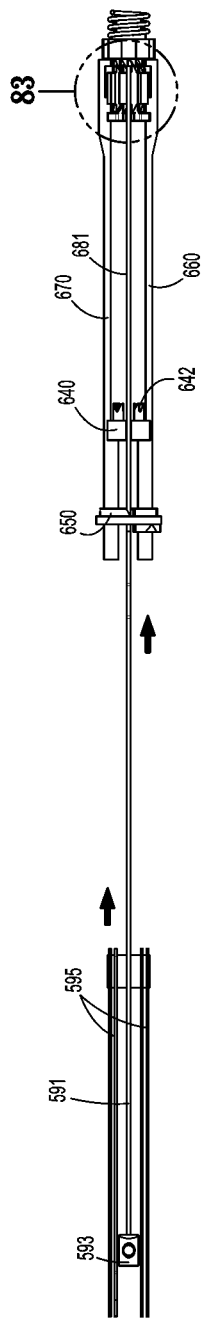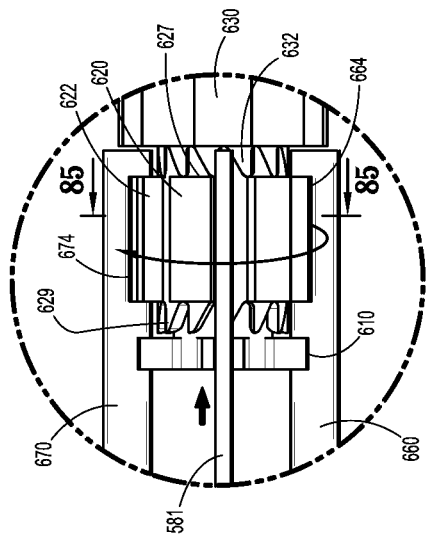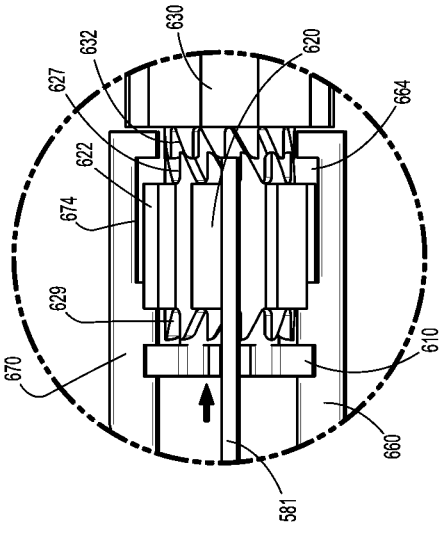

SURGICAL STAPLING APPARATUS

BACKGROUND

Technical Field

This application relates to a surgical stapling apparatus, and more particularly, to a reloadable, multi-fire endoscopic surgical stapling apparatus for sequentially applying a plurality of surgical fasteners to body tissue and incising fastened tissue.

Background of Related Art

Surgical devices wherein tissue is first grasped or clamped between opposing jaw structure and is then joined by surgical fasteners are well known in the art. In some instruments, a knife is provided to cut the tissue which has been joined by the fasteners. The fasteners are typically in the form of surgical staples, although two part polymeric fasteners can also be utilized.

Instruments for this purpose can include two elongated members which are respectively used to capture or clamp tissue. Typically, one of the members carries a staple cartridge which houses a plurality of staples arranged in at least two lateral rows while the other member has an anvil that defines a surface for forming the staple legs as the staples are driven from the staple cartridge. Generally, the stapling operation is effected by cam bars that travel longitudinally through the staple cartridge, with the cam bars acting upon staple pushers to sequentially eject the staples from the staple cartridge. A knife can travel between the staple rows to longitudinally cut and/or open the stapled tissue between the rows of staples.

In endoscopic or laparoscopic procedures, surgery is performed through a small incision or through a narrow cannula inserted through small entrance wounds or openings in the skin. In order to address the specific needs of endoscopic and/or laparoscopic surgical procedures, endoscopic surgical stapling devices have been developed.

Current endoscopic stapling devices are configured to operate with single use loading units ("SULU's") or disposable staple cartridges that are configured as single-use, or single-fire components. As such, during a normal operation, a surgeon may be required to utilize several SULU's or cartridges to perform a single endoscopic surgical procedure, e.g., where a plurality of firings is required. For each subsequent firing, the surgeon must remove the stapling device from the internal surgical site in order to replace the spent component(s) with new component(s). This repeated removal and manual reloading of the stapling device during the course of a single procedure increases the time, complexity, and overall costs associated with the endoscopic surgical procedure.

It would therefore be beneficial to provide a surgical stapling device and corresponding loading unit that is configured for multiple-firings, thus obviating the need to withdraw the device from the internal surgical site in order to manually reload the device for subsequent firings.

SUMMARY

In accordance with one embodiment of the present disclosure, a surgical stapler is provided. The surgical stapler includes an anvil assembly defining staple forming depressions and a cartridge assembly. The anvil assembly and/or the cartridge assembly are pivotable relative to one other between an open position and a clamped position. The cartridge assembly includes a first plurality of staples and a second plurality of staples. The first plurality of staples is initially positioned in alignment with the staple forming depressions of the anvil assembly for ejection from the cartridge assembly. The second plurality of staples is movably supported in the cartridge assembly from a first position misaligned with the staple forming depressions of the anvil assembly to a second position aligned with the staple forming depressions for subsequent ejection from the cartridge assembly.

In embodiments, the first plurality of staples is housed within a first plurality of conveyor links prior to ejection of the first plurality of staples from the cartridge assembly and the second plurality of staples is housed within a second plurality of conveyor links prior to ejection of the second plurality of staples from the cartridge assembly.

The first and second plurality of conveyor links may be supported on a conveyor. In such an embodiment, the conveyor is rotatable to rotate the second plurality of staples from the first position to the second position.

In embodiments, the first plurality of conveyor links initially define an upper tissue-contacting portion of the conveyor, the second plurality of conveyor links initially define an upper proximal portion of the conveyor, and a third plurality of conveyor links initially define a lower distal portion of the conveyor. Further, a plurality of pushers may initially be disposed within the third plurality of conveyor links. In such an embodiment, the pushers are movable from the third plurality of conveyor links to a position within the first plurality of conveyor links to eject the first plurality of staples from the cartridge assembly. When the second plurality of staples are moved to the second position, the first plurality of conveyor links may be positioned to define the lower distal portion of the conveyor and the second plurality of conveyor links may be positioned to define the upper tissue-contacting portion of the conveyor. As such, when the second plurality of staples is moved to the second position, the plurality of pushers may be positioned to be movable from within the first plurality of conveyor links into the second plurality of conveyor links to eject the second plurality of staples from the cartridge assembly.

In one embodiment, one or more cam bars is selectively translatable through the cartridge assembly. The cam bar(s) is configured to eject the staples positioned in alignment with the staple forming depressions of the anvil assembly from the cartridge assembly upon translation of the cam bar(s) through the cartridge assembly.

In another embodiment, one or more reload bars is selectively translatable through the cartridge assembly. The reload bar(s) is configured to effect movement of the second plurality of staples from the first position to the second position upon translation of the reload bar(s) through the cartridge assembly.

A fire and reload assembly may also be provided. The fire and reload assembly is transitionable between a firing mode, for ejecting the staples positioned in alignment with the staple forming depressions of the anvil assembly, and a reload mode, for rotating the second plurality of staples from the first position to the second position. Further, the fire and reload assembly may be alternately transitioned between the firing mode and the reload mode in response to complete advancement and retraction of the fire and reload assembly.

Another embodiment of a surgical stapler provided in accordance with the present disclosure includes an anvil assembly, a cartridge assembly, a drive bar, one or more reload bars, and a fire and reload assembly. The anvil assembly and/or the cartridge assembly are pivotable relative to one other between an open position and a clamped position. The cartridge assembly includes a first plurality of staples and a second plurality of staples. The drive bar is translatable through the cartridge assembly to eject the first plurality of staples from the cartridge assembly. The reload bar(s) is translatable through the cartridge assembly to move the second plurality of staples within the cartridge assembly to a position for subsequent ejection from the cartridge assembly. The fire and reload assembly includes a coupler and is transitionable between a firing mode and a reload mode. When the fire and reload assembly is in the firing mode, the coupler is engaged to the drive bar and when the fire and reload assembly is in the reload mode, the coupler is engaged to the reload bar(s).

In embodiments, the coupler is configured such that translation of the coupler in the firing mode advances the drive bar to eject the first plurality of staples from the cartridge assembly and/or such that translation of the coupler in the reload mode advances the reload bar(s) to move the second plurality of staples within the cartridge assembly into the position for subsequent ejection from the cartridge assembly. Translation of the coupler in the firing mode once the coupler has been translated in the reload mode to move the second plurality of staples into position for subsequent ejection may be operable to eject the second plurality of staples from the cartridge assembly.

In one embodiment, a handle assembly including a movable handle is provided. The movable handle is movable from a non-compressed position to a compressed position to translate the coupler. In the firing mode of the fire and reload assembly, the movable handle is movable from the non-compressed position to the compressed position to eject the first plurality of staples from the cartridge assembly. In the reload mode of the first and reload assembly, the movable handle is movable from the non-compressed position to the compressed position to move the second plurality of staples within the cartridge assembly into the position for subsequent ejection from the cartridge assembly. Additionally, movement of the movable handle from the non-compressed position to the compressed position and back to the non-compressed position may be operable to transition the fire and reload assembly between the firing mode and the reload mode.

In one embodiment, the fire and reload assembly further includes a lock ring. The lock ring is configured to inhibit translation of the reload bar(s) when the fire and reload assembly is in the firing mode and to inhibit translation of the drive bar when the fire and reload assembly is in the reload mode.

BRIEF DESCRIPTION OF THE DRAWINGS

Various embodiments of the present disclosure are described herein with reference to the drawings wherein:

FIG. 3 is a front, perspective view of the distal end of the SULU shown in an open position;

FIG. 4 is a front, perspective view of the distal end of the SULU shown in a clamped position;

FIG. 8 is an enlarged view of the indicated area of detail of FIG. 7;

FIG. 9 is a perspective view of the lock ring of the fire and reload assembly of the SULU;

FIG. 10 is a front, perspective view of the drive assembly of the SULU shown with parts separated;

FIG. 11 is an enlarged view of the indicated area of detail of FIG. 7;

FIG. 12 is an enlarged view of the indicated area of detail of FIG. 7;

FIG. 13 is a rear, perspective view of adjacent conveyor links of the SULU;

FIG. 14 is a rear, perspective view of one of the pushers of the SULU;

FIG. 14A is a front, perspective view of the pusher of FIG. 14;

FIG. 17 is an enlarged view of the indicated area of detail of FIG. 12;

FIG. 18 is an enlarged view of the indicated area of detail of FIG. 12;

FIG. 18A is an enlarged view of the indicated area of detail of FIG. 12;

FIG. 19 is a plan view of the conveyor assembly of the SULU;

FIG. 20 is a cross-sectional view taken along section line 20-20 of FIG. 19;

FIG. 21 is a cross-sectional view taken across section line 21-21 of FIG. 19;

FIG. 22 is a cross-sectional view taken along section line 22-22 of FIG. 2;

FIG. 23 is an enlarged view of the indicated area of detail of FIG. 22;

FIG. 24 is a longitudinal, cross-sectional view of the SULU shown during advancement of the drive assembly;

FIG. 25 is an enlarged view of the indicated area of detail of FIG. 24;

FIG. 26 is a rear, perspective view of the fire and reload assembly of the SULU;

FIG. 27 is an enlarged, perspective view of the proximal end of the fire and reload assembly;

FIG. 28 is a plan view of the fire and reload assembly;

FIG. 29 is an enlarged view of the indicated area of detail of FIG. 28;

FIG. 39 is a perspective view of the toothed rack of the handle assembly;

FIG. 40 is a cross-sectional view taken along section line 40-40 of FIG. 39;

FIG. 50 is a longitudinal, cross-sectional view of the proximal end of the elongated body of the stapler;

FIG. 51 is a side view of the proximal end of the SULU and the elongated body of the stapler, wherein the SULU and elongated body are disengaged from one another;

FIG. 54 is a longitudinal, cross-sectional view of the distal end of the elongated body shown in the engaged position;

FIG. 55 is a side view of the proximal end of the SULU inserted into the elongated body;

FIG. 56 is a side view of the proximal end of the SULU shown rotating into engagement within the elongated body;

FIG. 57 is a side view of the proximal end of the SULU engaged within the elongated body;

FIG. 63 is a front, perspective view of the fire and reload assembly shown in a partially fired position;

FIG. 64 is a transverse, cross-sectional view of the lock ring of the fire and reload assembly shown in a first position;

FIG. 65 is a longitudinal, cross-sectional view of the SULU shown in a partially fired position;

FIG. 66 is an enlarged view of the indicated area of detail of FIG. 65;

FIG. 69 is a transverse, cross-sectional view of a portion of the handle assembly illustrating the actuator assembly moving from the grasper mode to the firing mode;

FIG. 70 is a cross-sectional view taken along section line 70-70 of FIG. 68;

FIG. 75 is a longitudinal, cross-sectional view of the SULU after firing a first set of staples;

FIG. 76 is an enlarged view of the indicated area of detail of FIG. 75;

FIG. 77 is a plan view of the fire and reload assembly of the SULU shown in the firing mode;

FIG. 78 is an enlarged view of the indicated area of detail of FIG. 77;

FIG. 79 is an enlarged view of a portion of the fire and reload assembly of the SULU transitioning from the firing mode towards the reload mode;

FIG. 81 is a longitudinal, cross-sectional view of the handle assembly showing the toothed rack retracting proximally;

FIG. 82 is a plan view of the fire and reload assembly transitioning from the firing mode further towards the reload mode;

FIG. 83 is an enlarged view of the indicated area of detail of FIG. 82;

FIG. 84 is an enlarged view of a portion of the fire and reload assembly shown in the reload mode;

DETAILED DESCRIPTION

Figure 1:
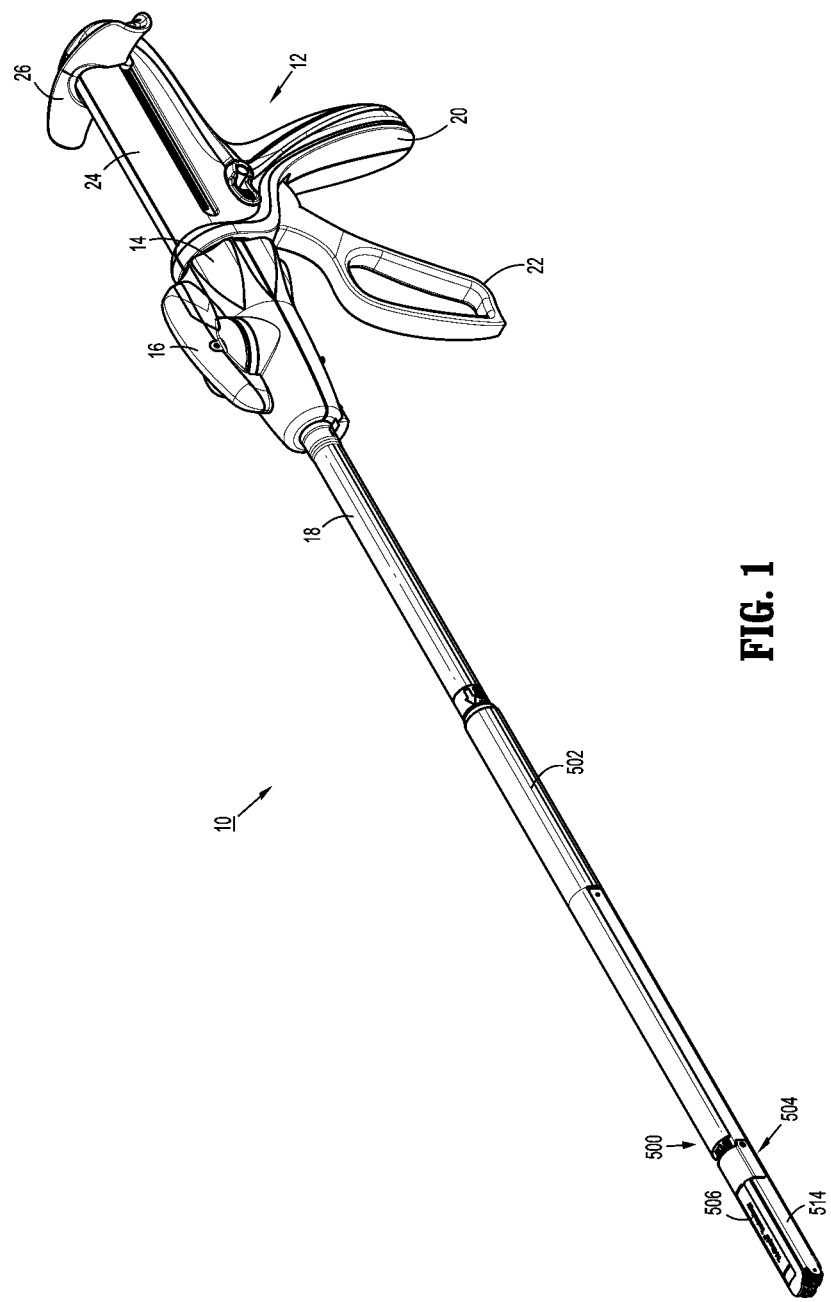
FIG. 1 is a front, perspective view of one preferred embodiment of the presently disclosed surgical stapling apparatus.

Embodiments of the present disclosure are described in detail with reference to the drawing figures wherein like reference numerals identify similar or identical elements. As used herein, the term "distal" refers to the portion of the apparatus that is being described which is further from a user, while the term "proximal" refers to the portion of the apparatus that is being described which is closer to a user.

Figure 2:
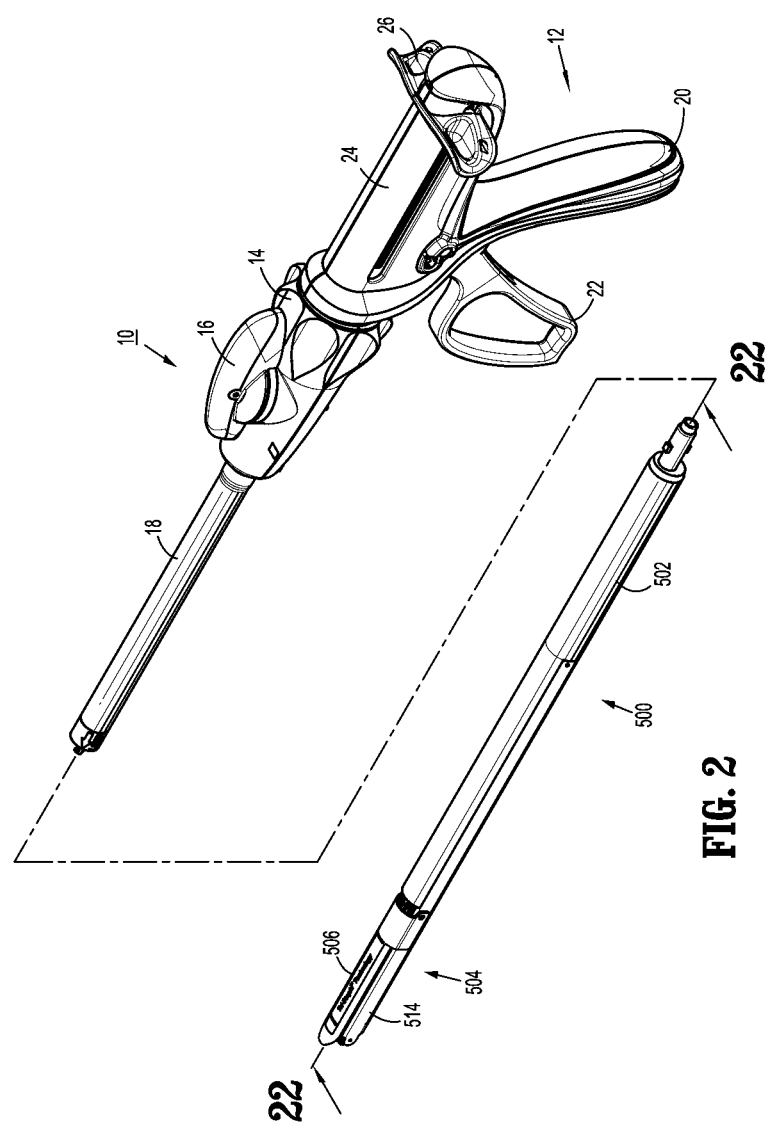
FIG. 2 is a rear, perspective view of the surgical stapling apparatus with the SULU detached from the elongated body.
Figure 5:
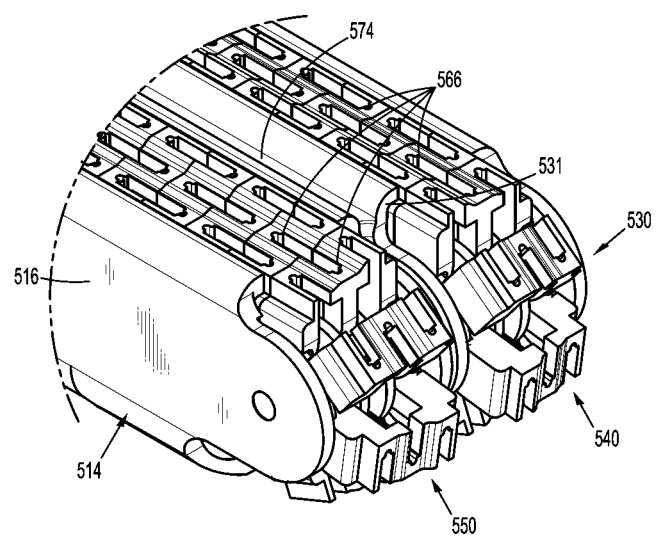
FIG. 5 is an enlarged view of the indicated area of detail shown in FIG. 3.

Turning now to FIGS. 1-2, an endoscopic surgical stapler provided in accordance with the present disclosure is shown generally identified by reference numeral 10. Stapler 10 generally includes a handle assembly 12, a rotation knob 14, an articulation lever 16 and an elongated body portion 18 that is configured to engage a SULU 500. Each of these components will be described in detail below. Although one embodiment of a stapler 10 is shown and described herein, it is envisioned that the SULU 500 may be configured for use in conjunction with any other suitable surgical stapling apparatus.

Turning to FIGS. 2-32, SULU 500 is described. With initial reference to FIGS. 2-4, SULU 500 generally includes a proximal body portion 502 and a tool assembly 504. Proximal body portion 502 is releasably attachable to a distal end of elongated body portion 18 of stapler 10, as will be described below, and tool assembly 504 extends from a distal end of proximal body portion 502. Tool assembly 504 includes an anvil assembly 506 and a cartridge assembly 514. Anvil assembly 506 is pivotal in relation to cartridge assembly 514 from an open or unclamped position (FIG. 3) to a closed or clamped position (FIG. 4), as will be discussed in further detail below.

Figure 6:
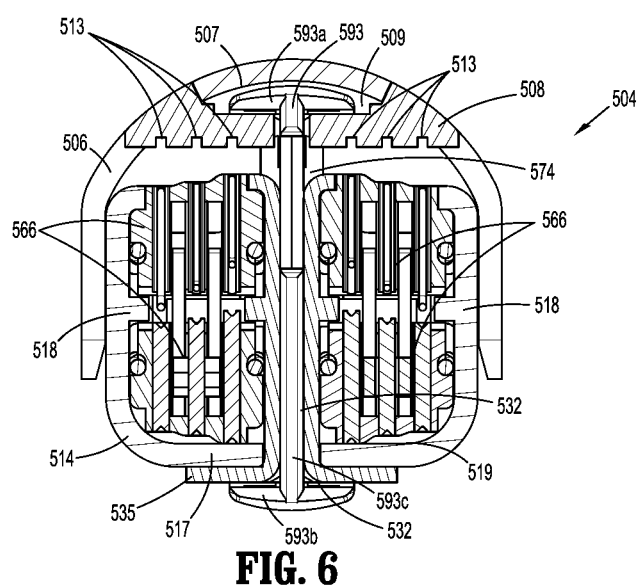
FIG. 6 is a transverse, cross-sectional view taken along section line 6-6 of FIG. 4.
Figure 7:
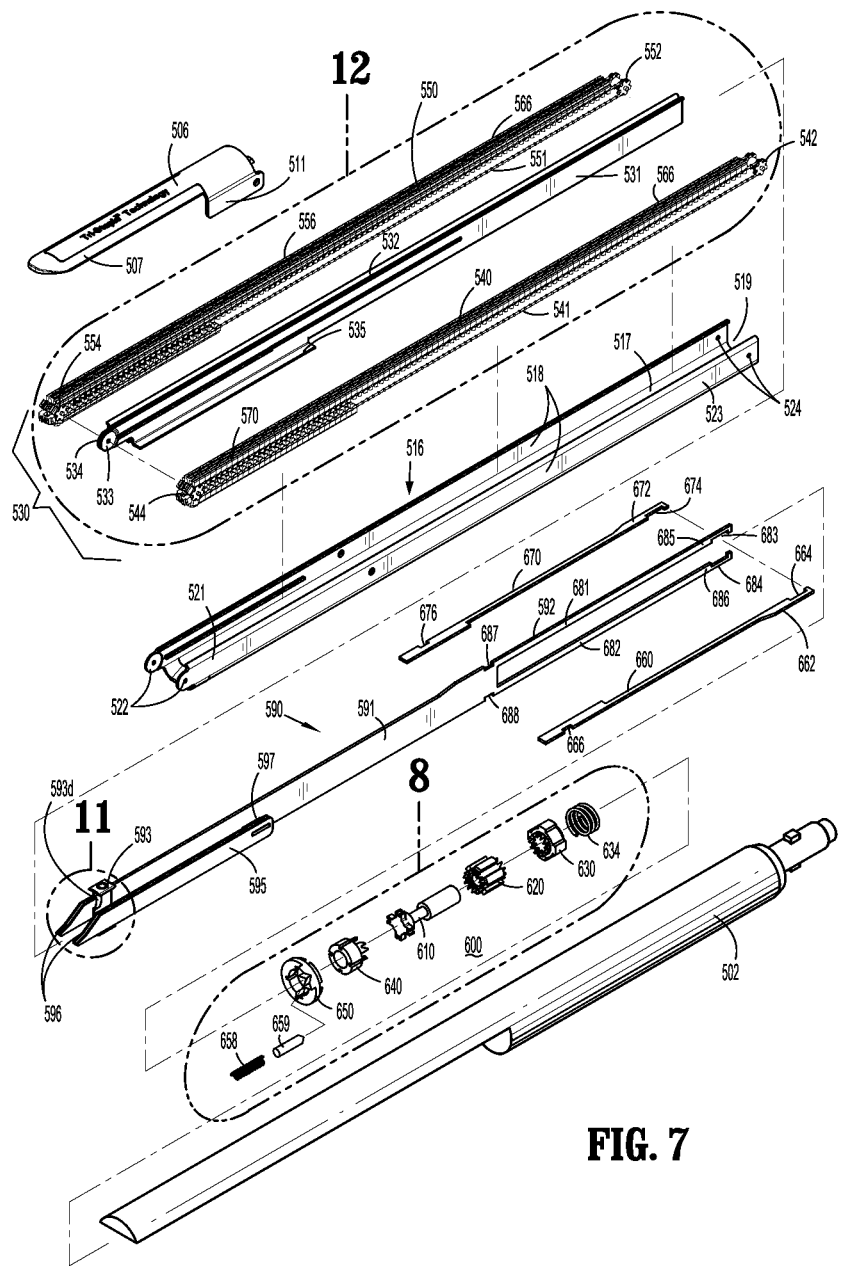
FIG. 7 is a front, perspective view of the SULU with parts separated.

Referring to FIGS. 3-7, anvil assembly 506 includes an anvil cover 507 that supports an anvil plate 508. Anvil plate 508 may include a plurality of staple forming depressions 513 configured such that, when tool assembly 504 is in the clamped position (FIG. 1), staple forming depressions 513 are positioned in juxtaposed alignment with staple slots 568 (FIG. 13) formed within cartridge assembly 514. Accordingly, as each staple "S" (FIGS. 20-21) is ejected from one of staple slots 568 (FIG. 13) of cartridge assembly 514, each staple "S" (FIGS. 20-21) is advanced through tissue grasped between anvil assembly 506 and cartridge assembly 514 and into one of the staple forming depressions 513 such that staples "S" (FIGS. 20-21) are formed about tissue. Anvil plate 508 is secured to an underside of anvil cover 507 to define a channel 509 between plate 508 and cover 507 (FIG. 6). Channel 509, as will be descried below, defines a generally "T"-shaped configuration that is adapted to receive and guide upper beam 593a of dynamic clamping member 593 therethrough. Anvil cover 507 includes a proximal portion 510 having a pair of spaced-apart flanges 511, 512 that are pivotably coupled to cartridge assembly 514 on either side of cartridge assembly 514, thus allowing anvil assembly 506 to pivot relative to cartridge assembly 514 between the open position (FIG. 3) and the clamped position (FIG. 4). Alternately, cartridge assembly 514 may be pivotally mounted in relation to anvil assembly 506.

With reference to FIGS. 6-7 and 12-21, cartridge assembly 514 includes a frame member 516 which rotatably supports a conveyor assembly 530, a drive assembly 590, and a fire and reload assembly 600. Frame member 516 defines a generally U-shaped configuration having a base 517 and a pair of spaced-apart sidewalls 518 that define an elongated channel 519 therebetween. Elongated channel 519 is configured to receive conveyor assembly 530 therein. More specifically, frame member 516 includes a pair of opposed proximal apertures 522 defined through sidewalls 518 at proximal ends 521 thereof that are configured to rotatably support the proximal end of conveyor assembly 530 and a pair of distal apertures 524 defined through sidewalls 518 at distal ends 523 thereof that are configured to rotatably support the distal end of conveyor assembly 530.

Conveyor assembly 530 generally includes a central support member 531 and first and second conveyors 540, 550, respectively, disposed on either side of central support member 531. Central support member 531 defines an elongated channel 532 (FIG. 6) therethrough that is configured to receive and guide translation of dynamic clamping member 593 to cut tissue grasped between anvil assembly 506 and cartridge assembly 514. Central support member 531 further includes an outwardly-flanged lower portion 535 that, as best shown in FIG. 6, extends through a slot defined within base 517 of frame member 516 to secure central support member 531 and frame member 516 to one another. Each of the conveyors 540, 550 includes a pair of conveyor chains 541, 551, respectively, that define looped configurations (FIG. 12). More specifically, the pair of conveyor chains 541, 551 of each conveyor 540, 550, respectively, is disposed about a proximal sprocket 542, 552, respectively, at the proximal end thereof and a distal sprocket 544, 554, respectively, at the distal end thereof. Proximal sprockets 542, 552 are rotatably supported within opposed proximal apertures 522 defined through sidewalls 518 of frame member 516. Distal sprockets 544, 554, on the other hand, are rotatably supported within opposed distal apertures 524 defined through sidewalls 518 of frame member 516 and within aperture 534 defined through distal disc 533 of central support member 531. First and second conveyors 540, 550, respectively, of conveyor assembly 530 are substantially similar to one another and, thus, only first conveyor 540 will be described hereinbelow to avoid unnecessary redundancy.

Continuing with reference to FIGS. 6-7 and 12-21, the conveyor chains 541 of conveyor 540 cooperate with one another to support a plurality of conveyor links 566 thereon along a substantial portion of conveyor chains 541. Conveyor links 566, as best shown in FIG. 13, are shaped complementary to one another such that adjacent conveyor links 566 mate with one another to form an upper, tissue-contacting surface 570 of conveyor 540 on the upper portion thereof and a lower portion 572 of conveyor 540 (see FIGS. 18, 18A and 19). Similarly, conveyor links 566 mate with one another to form an upper, tissue-contacting surface 556 of second conveyor 550 on the upper portion thereof. Upper, tissue-contacting surfaces 570, 556 of first and second conveyors 540, 550, respectively, are disposed on either side of channel 574 (see FIG. 3) and together form the upper, tissue-contacting surface of cartridge assembly 514. Conveyor links 566 also cooperate to form three linear rows of staple slots 568 (although greater or fewer than three rows of staple slots are contemplated) extending longitudinally along upper, tissue-contacting surfaces 570, 556 of conveyors 540, 550, respectively. A staple "S" is housed within each of staple slots 568. Further, each staple slot 568 is configured to receive a portion of a pusher 580 to fire, or eject staples "S" from cartridge assembly 514. More specifically, pushers 580, as shown in FIG. 14, 14A, 16 and 19-21, each define three blocks 582 that each engage the backspan of a staple "S" (one from each of the linear rows) such that, upon actuation, cam wedges 596 of cam bars 595 urge pushers 580 upwardly into staple slots 568, which, in turn, urge staples "S" upwardly to eject staples "S" from cartridge assembly 514. Staples "S," pushers 580, and cam bars 595 will be described in detail below.

A set of conveyor links 566, as best shown in FIGS. 13, 18, 18A and 19, and as mentioned above, mate with one another to form the upper, tissue-contacting surface 570 of conveyor 540 (and, similarly, upper, tissue-contacting surface 556 of conveyor 550), while the remainder of conveyor links 566 are disposed at other positions along conveyor chains 541, e.g., proximally of upper, tissue-contacting surface 570, on lower portion 572, about proximal sprocket 542, about distal sprocket 544, etc. Conveyor links 566 are rotatable along frame member 516 and about proximal and distal sprockets 542, 544, respectively. More specifically, conveyor links 566 are rotated along the loop formed by conveyor chains 541 of conveyor 540 from a position on the upper portion of conveyor 540 wherein conveyor links 566 define upper, tissue-contacting surface 570, counter-clockwise about distal sprocket 544, proximally along lower portion 572, counter-clockwise about proximal sprocket 542, distally to form the upper, tissue-contacting surface 570, etc. As will be described in greater detail below, such a configuration permits a new set of conveyor links 566 (the conveyor links 566 positioned proximally of upper, tissue-contacting surface 570) to be moved into position in juxtaposed alignment with staple forming depressions 513 (FIG. 6) of anvil plate 508 (FIG. 6) to define the upper, tissue-contacting surface 570 of conveyor 540 once the staples "S" of the previous set of conveyor links 566 have been fired. With new conveyor links 566 in position, stapler 10 may be fired to eject a second set of staples "S" from cartridge assembly 514. In other words, a plurality of sets of staples "S" can be fired from SULU 500 without requiring a new SULU for each firing operation. The operation of SULU 500 in firing multiple sets of staples "S" will be described in greater detail hereinbelow.

Figure 15:
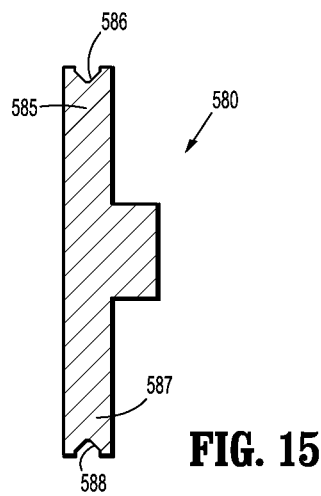
FIG. 15 is a cross-sectional view taken along section line 15-15 of FIG. 14.
Figure 16:
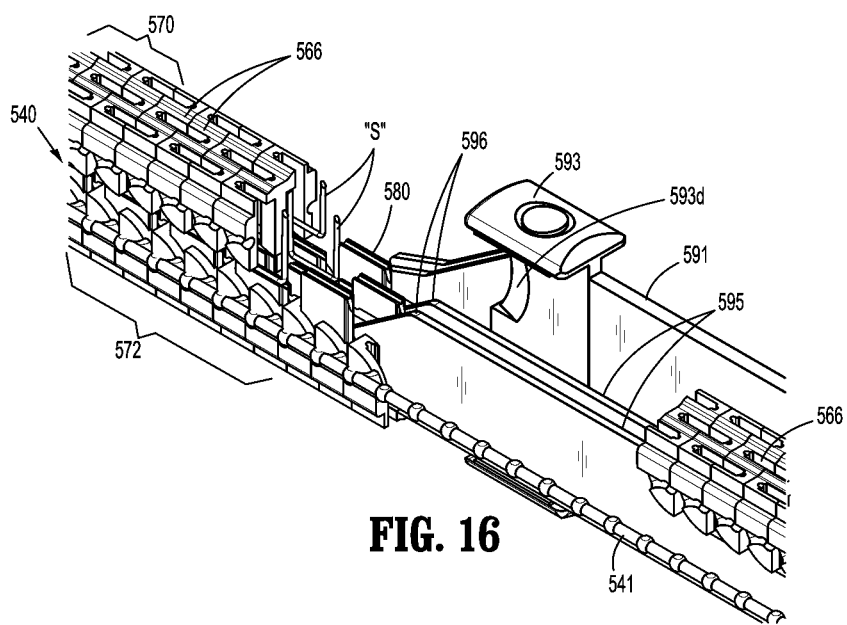
FIG. 16 is a rear, perspective view of the conveyor assembly and drive assembly of the SULU.
Figure 31:
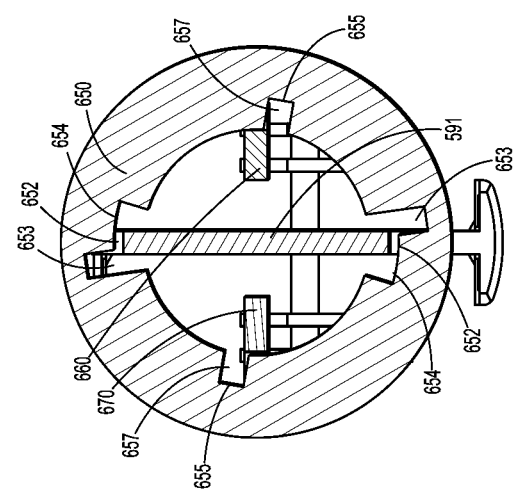
FIG. 31 is a cross-sectional view taken along section line 31-31 of FIG. 26.
Figure 30:
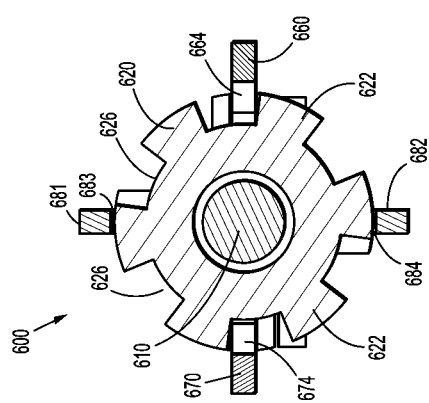
FIG. 30 is a cross-sectional view taken along section line 30-30 of FIG. 27.
Figure 32:
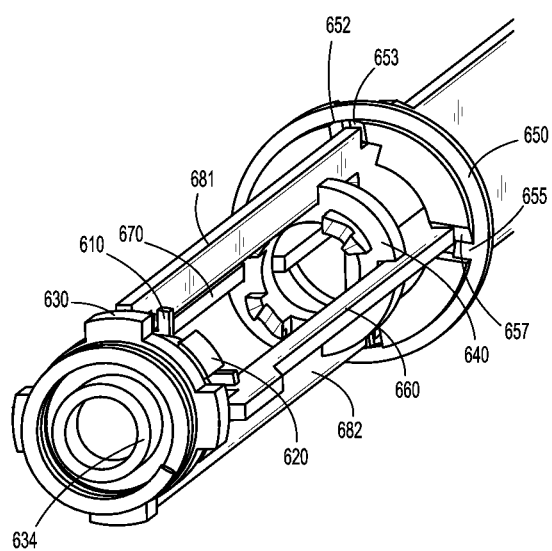
FIG. 32 is a rear, perspective view of the fire and reload assembly.

With additional reference to FIGS. 14, 14A, 15, 19, 20, 21 and 25, each pusher 580, as mentioned above, defines three blocks 582 (although greater or fewer blocks are contemplated) that each engage the backspan of one of staples "S" (one from each of the linear rows) during firing to facilitate ejection of staples "S" from cartridge assembly 514. Pushers 580 are disposed between the conveyor links 566 forming upper, tissue-contacting surface 570 of conveyor 540 and the conveyor links 566 disposed on the lower portion 572 of conveyor 540 directly beneath upper, tissue-contacting surface 570, and are configured as bi-directional pushers 580. Initially, as shown in FIG. 25, pushers 580 are disposed within slots 568 defined within conveyor links 566 of lower portion 572 of conveyor 540 such that, upon actuation, cam wedges 596 of cam bars 595 contact angled surfaces 584 of pushers 580 to urge pushers 580 upwardly from slots 568 of conveyor links 566 of lower portion 572 into slots 568 defined within conveyor links 566 forming upper, tissue-contacting surface 570 of conveyor 540 to eject staples "S" therefrom. Pushers 580, as shown in FIG. 15, define grooves 586 at first end 585 thereof that are configured to receive the backspans of staples "S" to guide the ejection of staples "S" from conveyor links 566.

Figure 89:
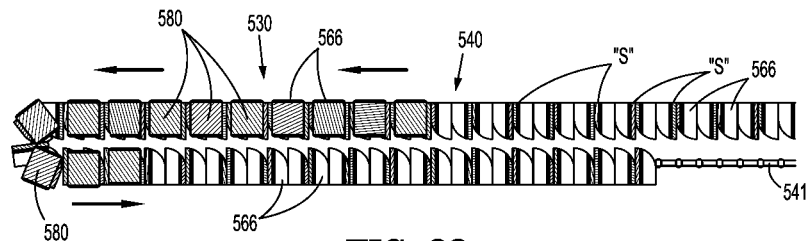
FIG. 89 is a schematic illustration showing the conveyor assembly rotating to reload the SULU.

Referring also to FIG. 89, once the initial set of staples "S" has been ejected, as will be described below, conveyor 540 is rotated such that the conveyor links 566 which housed the previously fired stapled, which now house pushers 580 disposed within slots 568 thereof, are rotated about distal sprocket 544 to lower portion 572 of conveyor 540, while a new set of conveyor links 566 (which include un-fired staples "S" therein) are translated distally along conveyor 540 to form upper, tissue-contacting surface 570 or a portion of surface 570 of conveyor 540. In this position, wherein pushers 580 are disposed within conveyor links 566 of lower portion 572 of conveyor 540, pushers 580 are oriented upside-down (due to the rotation of conveyor links 566 about distal sprocket 544). Accordingly, pushers 580 also define grooves 588 at a second end 587 thereof that are configured to receive the backspans of staples "S" therein to guide the ejection of staples "S" and also include angled surfaces 589 that are configured to cam along cam wedges 596 of cam bars 595 when in this upside-down orientation. That is, pushers 580 are operable to eject staples "S" from conveyor links 566 regardless of the orientation of pushers 580.

Referring now to FIGS. 6, 7, 10, 11, 12 and 16, drive assembly 590 includes a drive bar 591 having a bifurcated proximal end 592 and a distal end 594 that engages dynamic clamping member 593. Drive assembly 590 further includes a pair of cam bars 595 coupled to drive bar 591 on either side thereof. Cam bars 595 each include an angled distal end surface defining a cam wedge 596 configured to slidably contact complementary-shaped angled surfaces 584, 589 of pushers 580 (depending on the orientation of pushers 580) (see FIGS. 14-15) upon distal translation of drive bar 591 to urge pushers 580 upwardly to eject staples "S" from slots 568 of conveyor links 566. A tab 597 (FIG. 10) is received through slots 598 defined within each of cam bars 595 and through slot 599 defined within drive bar 591 to secure cam bars 595 and drive bar 591 in spaced-relation relative to one another.

Dynamic clamping member 593, as mentioned above, and as best shown in FIGS. 6-7 and 10-11, is disposed at distal end 594 of drive bar 591. Dynamic clamping member 593 includes an upper beam 593a and a lower beam 593b interconnected by an upright-member 593c. Upright member 593c defines a cutting blade 593d to facilitate advancement of dynamic clamping member 593 through tissue. Upon the initial actuation of drive assembly 590, as will be described in greater detail below, upper beam 593a of dynamic clamping member 593 is advanced into the upper transverse portion of T-shaped channel 509 defined between plate 508 and cover 507 of anvil assembly 506, distal beam 593b is translated along the exterior of frame member 516 and central support member 531, and upright member 593c is translated into the upright portion of T-shaped channel 509 of anvil assembly 506 and elongated channel 532 of central support member 531 (the upright portion of T-shaped channel 509 and elongated channel 532 of central support member 531 cooperate with one another to define channel 574 (FIG. 3)) to pivot anvil assembly 506 relative to cartridge assembly 514 to the clamped position (FIG. 4). However, this initial actuation, i.e., the clamping stroke, only advances dynamic clamping member 593 a sufficient distance to pivot anvil assembly 506 relative to cartridge assembly 514 to the clamped position (FIG. 4) without translating cam bars 595 into contact with pushers 580. Thus, upon the initial actuation, cam bars 595 remain proximally of pushers 580 such that neither firing of staples "S" nor cutting of tissue is effected.

Upon subsequent actuations of handle assembly 12, i.e., the firing stroke, (with handle assembly 12 disposed in the firing mode), as will be described in greater detail below, dynamic clamping member 593 is incrementally advanced further through SULU 500 such that cam bars 595 are urged into contact with pushers 580 to fire staples "S" therefrom and such that dynamic clamping member 593 is advanced through tissue to cut tissue between conveyors 540, 550 of cartridge assembly 514.

Referring to FIGS. 7-10, and 25-32, fire and reload assembly 600 generally includes a pair of laterally-opposed reload bars 660, 670, a non-rotary driver 610, a rotary coupler 620, a proximal cam 630, a distal cam 640, and a lock ring 650. Fire and reload assembly 600, as will become apparent in view of the following, is configured to alternately transition between a firing mode, wherein drive bar 591 is selectively advancable to eject staples "S" from cartridge assembly 514 and to cut tissue grasped between anvil assembly 506 and cartridge assembly 514, and a reload mode, wherein reload bars 660, 670 are advancable distally to urge conveyor links 566 to rotate about conveyors 540, 550 such that a new set of conveyor links 566 is positioned to form the upper, tissue-contacting surfaces 570, 556 of conveyors 540, 550, respectively, of cartridge assembly 514, while conveyor links 566 which housed the fired staples are rotated about distal sprockets 544, 554 to the lower portion of cartridge assembly 514. Due to this configuration, as can be appreciated, and as will be described in greater detail below, each complete firing operation is followed by a reloading operation that reloads SULU 500 for subsequent firing.

Proximal end 592 of drive bar 591, as mentioned above, defines a bifurcated configuration. More specifically, proximal end 592 of drive bar 591 includes an upper arm 681 and a lower arm 682 that are spaced-apart from one another and extend proximally from drive bar 591 to form proximal end 592 of drive bar 591. Upper and lower arms 681, 682, respectively, each define an opposed cut-out 683, 684 at free end 685, 686, respectively, thereof. Opposed cut-outs 683, 684 receive block protrusions 622 of rotary coupler 620 when fire and reload assembly 600 is disposed in the firing mode such that advancement of rotary coupler 620 effects similar advancement of drive bar 591. In the reload mode, cut-outs 683, 684, are offset relative to block protrusions 622 of rotary coupler 620 such that rotary coupler 620 is no longer coupled to upper and lower arms 681, 682 of drive bar 591 and, thus, translation of rotary coupler 620 does not effect corresponding translation of drive bar 591. Further, upper and lower arms 681, 682 are slidably supported within vertically-opposed slots 612, 613, respectively, defined within non-rotary driver 610 of fire and reload assembly 600 (see FIGS. 26-27), to guide translation of drive bar 591 when fire and reload assembly 600 is operating in the firing mode.

With continued reference to FIGS. 7-10, and 25-32, laterally-opposed reload bars 660, 670, similar to arms 681, 682 of drive bar 691, each include a proximal end 662, 672 defining a cut-out 664, 674, respectively. Laterally-opposed reload bars 660, 670, are offset 90 degrees relative to upper and lower arms 681, 682 of drive bar 591 and are slidably supported within laterally-opposed slots 614, 615, respectively, defined within non-rotary driver 610 to guide translation of reload bars 660, 670 when fire and reload assembly 600 is operating in the reload mode. Further, opposed cut-outs 664, 674 of reload bars 660, 670, respectively, are configured to receive block protrusions 622 of rotary coupler 620 when fire and reload assembly 600 is operating in the reload mode such that advancement of rotary coupler 620 effects similar advancement of reload bars 660, 670. In the firing mode, cut-outs 664, 674, are offset relative to block protrusions 622 of rotary coupler 620 such that rotary coupler 620 is no longer coupled to reload bars 660, 670 and, thus, translation of rotary coupler 620 does not effect corresponding translation of reload bars 660, 670.

Rotary coupler 620 is rotatably disposed about a proximal extension 616 of non-rotary driver 610 and, as mentioned above, is engaged to arms 681, 682 of drive bar 591 in the firing mode and to reload bars 660, 670 in the reload mode. More specifically, body portion 624 of rotary coupler 620 includes a plurality of spaced-apart block protrusions 622 disposed about the outer periphery thereof. Block protrusions 622 are spaced-apart from one another to define gaps 626 therebetween. As will be described below, rotary coupler 620 is rotatable about proximal extension 616 of non-rotary driver 610 and relative to drive bar 591 and reload bars 660, 670 to transition fire and reload assembly 600 between the firing mode and the reload mode. More specifically, in the firing mode, rotary coupler 620 is oriented such that opposed cut-outs 683, 684 of arms 681, 682, respectively, of drive bar 591 receive block protrusions 622, while reload bars 660, 670 are disposed within gaps 626. In the reload mode, on the other hand, rotary coupler 620 is rotated such that opposed cut-outs 664, 674 of reload bars 660, 670, respectively, receive block protrusions 622, while arms 681, 682 of drive bar 591 are disposed within gaps 626.

Rotary coupler 620 further includes a toothed proximal portion 627 and a toothed distal portion 629. Toothed proximal portion 627 includes a plurality of teeth, each generally defining a right triangle-shaped configuration. In other words, each tooth defines a longitudinal surface and an angled surface. The teeth are oriented similarly relative to one another to define a continuous toothed configuration about the circumference of toothed proximal portion 627. Toothed distal portion 629 also includes a plurality of teeth that generally define a right triangle-shaped configuration and are oriented similarly relative to one another. Alternately, different tooth configurations are envisioned.

Referring still to FIGS. 7-10, and 25-32, proximal and distal cams 630, 640, respectively, are stationarily disposed at the proximal and distal ends, respectively, of fire and reload assembly 600. Proximal cam 630 includes a toothed distal portion 632 that includes a plurality of teeth that are shaped complementarily to the teeth of toothed proximal portion 627 of rotary coupler 620. The teeth of proximal cam 630 are initially aligned with the teeth of toothed proximal portion 627 of rotary coupler 620. Proximal cam 630 is biased distally by a biasing member 634. Distal cam 640, on the other hand, includes a toothed proximal portion 642 that includes a plurality of teeth that are shaped complementarily to the teeth of toothed distal portion 629 of rotary coupler 620. Initially, the teeth of distal cam 640 are offset relative to the teeth of toothed distal portion 629 of rotary coupler 620.

Proximal cam 630 and distal cam 640 cooperate to rotate rotary coupler 620 upon full advancement and retraction of fire and reload assembly 600 such that fire and reload assembly 600 is transitioned between the firing mode and the reload mode after each full advancement and retraction of fire and reload assembly 600. More specifically, upon full advancement of fire and reload assembly 600, rotary coupler 620 is urged distally such that toothed distal portion 629 of rotary coupler 620 ultimately contacts toothed proximal portion 642 of distal cam 640. Due to the aligned configuration of the teeth of distal cam 640 and the teeth of toothed distal portion 629 of rotary coupler 620, as toothed distal portion 629 of rotary coupler 620 is urged into contact with toothed proximal portion 642 of distal cam 640, rotary coupler 620 is rotated relative to distal cam 640 such that the respective teeth are complementarily offset relative to one another, thus allowing rotary coupler 620 and distal cam 640 to mate with one another. Similarly, upon full retraction of fire and reload assembly 600, rotary coupler 620 is pulled proximally such that toothed proximal portion 627 of rotary coupler 620 ultimately contacts toothed distal portion 632 of proximal cam 630. Prior to contacting proximal cam 630, but after contacting and being rotated by distal cam 640, the teeth of toothed proximal portion 627 of rotary coupler 620 are aligned with the teeth of proximal cam 630 due to the rotation of rotary coupler 620 from its original position, as described above. Thus, due to the now aligned configuration of the teeth of proximal cam 630 and the teeth of toothed proximal portion 627 of rotary coupler 620, as toothed proximal portion 627 of rotary coupler 620 is urged into contact with toothed distal portion 632 of proximal cam 630, rotary coupler 620 is rotated relative to proximal cam 630 such that the respective teeth are complementarily offset relative to one another, thus allowing rotary coupler 620 and proximal cam 630 to mate with one another.

Continuing with reference to FIGS. 7-10, 25-32, 78-79 and 83-84, the rotation of rotary coupler 620 upon contact with proximal cam 630 during retraction of fire and reload assembly 600 is similar in direction to the rotation of rotary coupler 620 upon contact with distal cam 640. In fact, each rotation corresponds to a partial rotation of rotary coupler 620 between the firing mode and the reload mode. Thus, in use, with fire and reload assembly 600 initially in the firing mode, full advancement of fire and reload assembly 600 occurs when drive bar 591 is moved distally to eject staples "S" from SULU 500 and to advance dynamic clamping member 593 to cut stapled tissue. As the end of the firing stroke is reached, rotary coupler 620 contacts distal cam 640 and is rotated partially from the firing mode towards the reload mode, but is not rotated enough so as to disengage drive bar 591 from rotary coupler 620. Accordingly, with drive bar 591 and rotary coupler 620 still engaged, fire and reload assembly 600 can be retracted to thereby retract drive bar 591. Upon full retraction, rotary coupler 620 contacts proximal cam 630 and is rotated from the partially rotated orientation to the reload mode, wherein arms 681, 682 of drive bar 591 are disengaged from rotary coupler 620 and wherein reload bars 660, 670 are engaged to rotary coupler 620.

Upon subsequent full advancement and retraction of fire and reload assembly 600, reload bars 660, 670 are advanced to urge a new set of conveyor links 566 into position to form upper, tissue-contacting surfaces 570, 556 of conveyors 540, 550, respectively, of cartridge assembly 514 for subsequent firing. Contact of rotary coupler 620 with distal cam 640 at the end of the reload stroke rotates rotary coupler 620 partially back towards the firing mode and, upon retraction, contact of rotary coupler 620 with proximal cam 630 rotates rotary coupler 620 back into engagement with drive bar 591 such that fire and reload assembly 600 is returned to the firing mode for subsequent firing.

Referring now to FIGS. 9 and 26-31, lock ring 650 provides a locking feature that inhibits advancement of reload bars 660, 670 when fire and reload assembly 600 is in the firing mode, and inhibits advancement of drive bar 591 when fire and reload assembly 600 is in the reload mode. Lock ring 650, as shown in FIG. 8, includes a central aperture 651 and two pairs of opposed detent portions 652, 655. Drive bar 591 includes a pair of opposed intermediate cut-outs 687, 688 that are configured to be received within detent portions 652 of lock ring 650. Reload bars 660, 670 each include a distal cut-out 666, 676, respectively, that is configured to be received within detent portions 655.

Each detent portion 652, 655 further includes a slot 653, 656 adjacent respective detent portions 652, 655 and an angled surface 654, 657, respectively, leading to slots 653, 656, respectively. Slots 653 of the first pair of detent portions 652 and slots 656 of the second pair of detent portions 655 are not equally-spaced about lock ring 650, but, rather, are offset relative to one another. Due to this configuration, as will be described below, when drive bar 591 is aligned with slots 653, reload bars 660, 670 are offset relative to slots 656 and, similarly, when reload bars 660, 670 are aligned with slots 656, drive bar 591 is offset relative to slots 653, thus providing the locking feature of lock ring 650.

Lock ring 650 is rotatable between a first position, wherein drive bar 591 is aligned with slots 653 of detent portions 652 and reload bars 660, 670 are offset relative to slots 656 of detent portions 655, and a second position, wherein reload bars 660, 670 are aligned with slots 656 of detent portions 655 and drive bar 591 is offset relative to slots 653 of detent portions 652. In the first position, which corresponds to the firing mode, drive bar 591 is permitted to be translated through lock ring 650 due to the alignment of drive bar 591 with slots 653, while distal cut-outs 666, 676 of reload bars 660, 670, respectively, are disposed about detent portions 655, inhibiting translation of reload bars 660, 670. In the second position, which corresponds to the reload mode, reload bars 660, 670 are permitted to be translated through lock ring 650 due to the alignment of reload bars 660, 670 with slots 656, while intermediate cut-outs 687, 688 of drive bar 591 are disposed about detent portions 652, inhibiting translation of drive bar 591.

Angled surfaces 654, 657 of detent portions 652, 655, respectively, facilitate the rotation of lock ring 650 between the first and second positions. More specifically, as drive bar 591 is advanced distally during the firing mode, drive bar 591 is urged into contact with angled surfaces 654 of detent portions 652 to rotate lock ring 650, thus ensuring that drive bar 591 is aligned with slots 653 and that distal cut-outs 666, 676 of reload bars 660, 670, respectively, are disposed about detent portions 655. In the reload mode, during distal advancement of reload bars 660, 670, reload bars 660, 670, are urged into contact with angled surfaces 657 of detent portions 655 to rotate lock ring 650 in the opposite direction, thus ensuring that reload bars 660, 670 are aligned with slots 656 and that intermediate cut-outs 687, 688 of drive bar 591 are disposed about detent portions 652. A biasing member 658 and centering plunger 659 return lock ring 650 to a centered position in the absence of drive bar 591 or reload bars 660, 670 urging lock ring 650 to rotate to the first and second positions, respectively.

Referring to FIGS. 33-36, in conjunction with FIG. 1, stapler 10, as mentioned above, generally includes a handle assembly 12, a rotation knob 14, an articulation lever 16, and an elongated body portion 18 that is configured to engage SULU 500.

Handle assembly 12 is selectively operable, as will be described below, to clamp tissue between anvil assembly 506 and cartridge assembly 514, to fire a set of staples "S" (FIGS. 20-21) from SULU 500, and for reloading SULU 500 for subsequent firing. More specifically, handle assembly 12 is transitionable between a grasper mode and a firing mode for grasping tissue between anvil assembly 506 and cartridge assembly 514 and for incrementally firing a plurality of staples "S" through tissue and dividing tissue grasping between anvil assembly 506 and cartridge assembly 514, respectively. Handle assembly 12 generally includes a stationary handle portion 20, a trigger or movable handle portion 22, a barrel portion 24, and retraction knobs 26. An actuator button 28 extends transversely through and projects outwardly from opposite sides of handle assembly 12. Handle assembly 12 is formed from a pair of housing sections 12a and 12b that cooperate to form stationary handle portion 20 and barrel portion 24. Housing sections 12a and 12b also define a cavity 30 for receiving the internal components of handle assembly 12, which will be described in greater detail hereinbelow.

Figure 33:
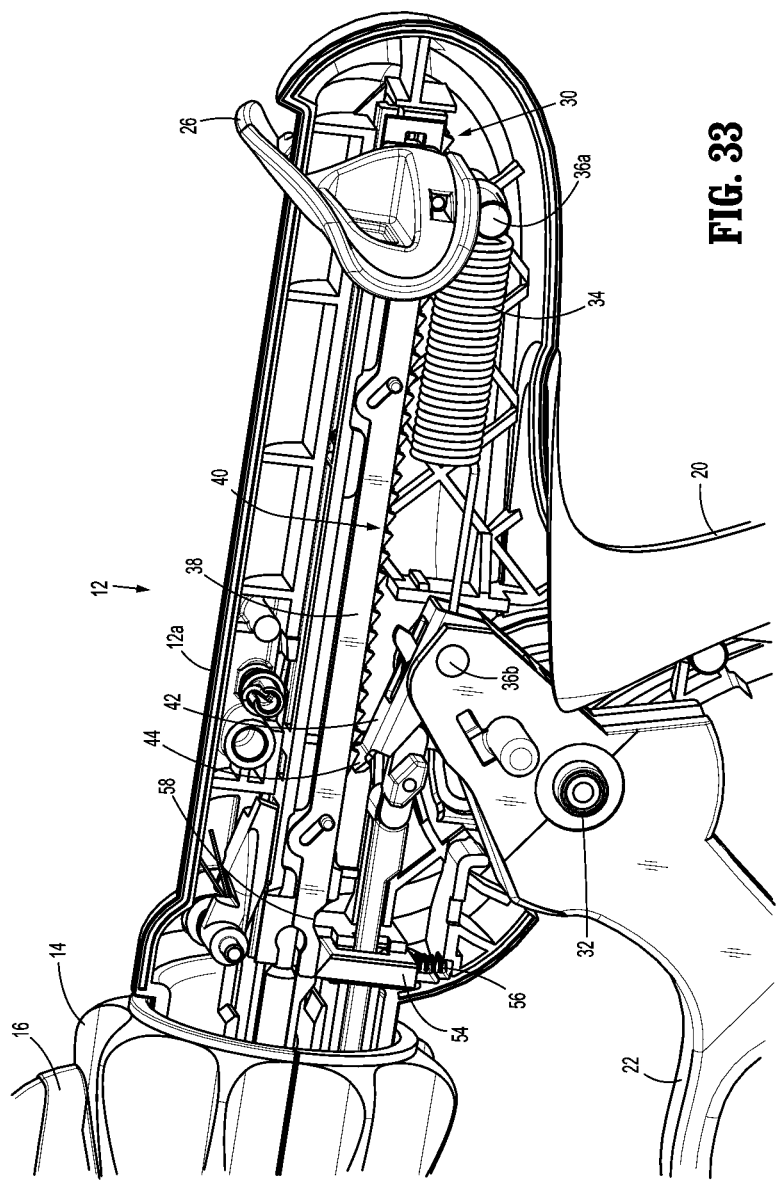
FIG. 33 is a perspective view of the handle assembly of the stapler with a portion of the housing removed to show the internal components, and with the movable handle in the original position.
Figure 34:
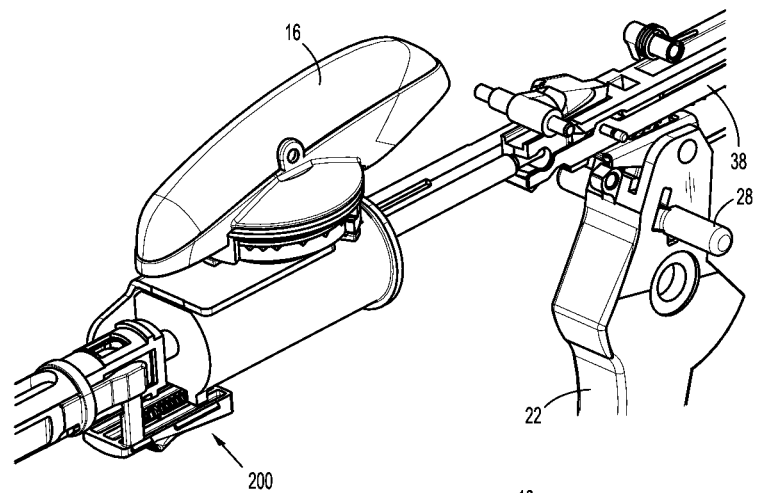
FIG. 34 is a front, perspective view of the shaft assembly of the stapler.
Figure 35:
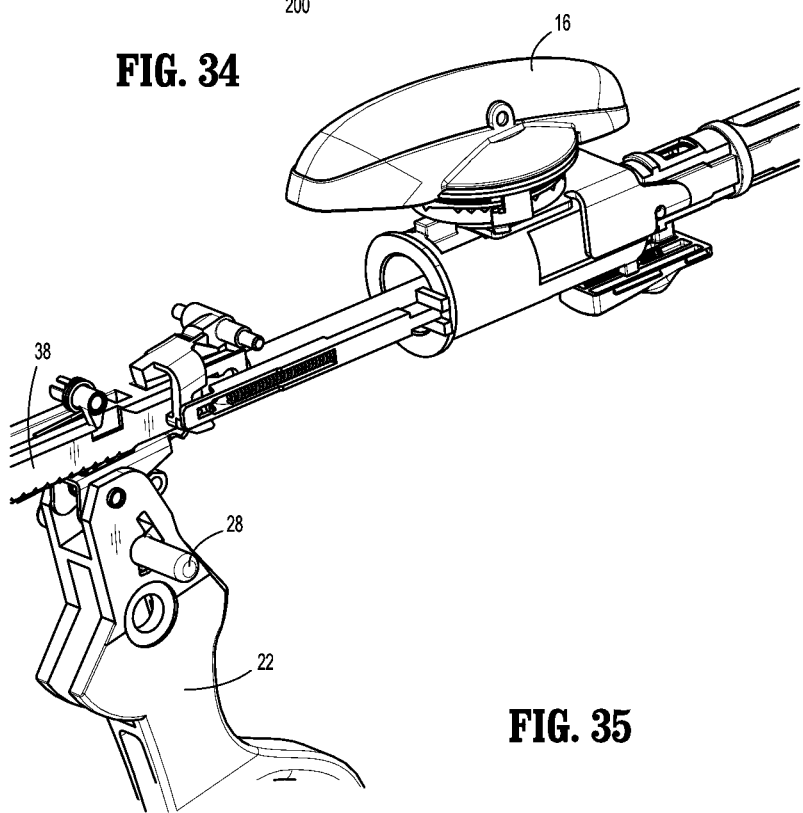
FIG. 35 is a rear, perspective view of the shaft assembly.

With continued reference to FIGS. 33-36, movable handle 22 of handle assembly 12 is pivotably supported between housing sections 12a and 12b about a pivot member 32 (FIG. 33). A biasing member 34 has a first end secured about a post 36a on housing half-section 12a and a second end which engages a post 36b supported on movable handle 22 to bias movable handle 22 away from stationary handle 20 to a non-compressed position corresponding to the open or unclamped position of tool assembly 504 of SULU 500 (see FIG. 1).

An actuation shaft 38 is supported within barrel portion 24 of handle assembly 12 and includes a toothed rack 40. A driving pawl 42 having a rack engagement finger 44 with laterally extending wings 44a and 44b is pivotably mounted to one end of movable handle 22 about post 36b. A biasing member 48 is positioned to urge engagement finger 44 of driving pawl 42 towards toothed rack 40 of actuation shaft 38. Movable handle 22 is pivotable to move engagement finger 44 of driving pawl 42 into contact with toothed rack 40 of actuation shaft 38 to advance actuation shaft 38 linearly in the distal direction. The forward end of actuation shaft 38 includes a recess 39 (FIG. 39) for rotatably receiving the proximal end 50 of a control rod 52 (FIG. 41) such that linear advancement of actuation shaft 38 causes corresponding linear advancement of control rod 52, which, in turn, correspondingly translates rotary coupler 620 of fire and reload assembly 600 to advance drive bar 591 or reload bars 660, 670, depending on whether fire and reload assembly 600 is in the firing mode or the reload mode (see FIGS. 26, 28).

A vertical pawl 54 is movably supported within handle assembly 12 and is biased towards a cutout 58 in actuation shaft 38 by biasing member 56. Vertical pawl 54 is movable into engagement with cutout 58 and toothed rack 40 to retain actuation shaft 38 in a longitudinally fixed position.

A retraction mechanism 57 which includes retraction knobs 26 (See FIG. 1) is connected to the proximal end of actuation shaft 38 by a coupling rod 60. Coupling rod 60 includes right and left engagement portions 62a and 62b for receiving retraction knobs 26 and a central portion 62c which is dimensioned and configured to translate within a pair of longitudinal slots 64 formed in actuation shaft 38 adjacent the proximal end thereof. A release plate 66 is operatively associated with actuation shaft 38 and is mounted for movement with respect thereto in response to manipulation of retraction knobs 26. A pair of spaced-apart pins 68 extend outwardly from a lateral face of actuation shaft 38 to engage a pair of corresponding angled cam slots 70 formed in release plate 66. Referring also to FIG. 81, upon rearward movement of retraction knobs 26, pins 68 cam release plate 66 downwardly with respect to actuation shaft 38 and with respect to toothed rack 40 such that the bottom portion of release plate 66 extends below toothed rack 40 to disengage vertical pawl 54 and engagement finger 44 of driving pawl 42 from toothed rack 40. A transverse slot 72 (FIG. 36) is formed at the proximal end of release plate 66 to accommodate the central portion 62c of coupling rod 60. Coupling rod 60 is biased distally by spring 76 (FIG. 36) which is secured at one end to coupling rod portion 60 via connector 78 and at the other end to post 80 on actuation shaft 38. By urging coupling rod 60 distally, release plate 66 is urged towards a position above toothed rack 40. Elongated slots 74 (See FIG. 1) are defined in the barrel portion 24 of handle assembly 12 to accommodate the longitudinal translation of coupling rod 60 as retraction knobs 26 are pulled rearwardly to retract actuation shaft 38 and thus retract control rod 52 (FIG. 41) rearwardly.

Figure 36:
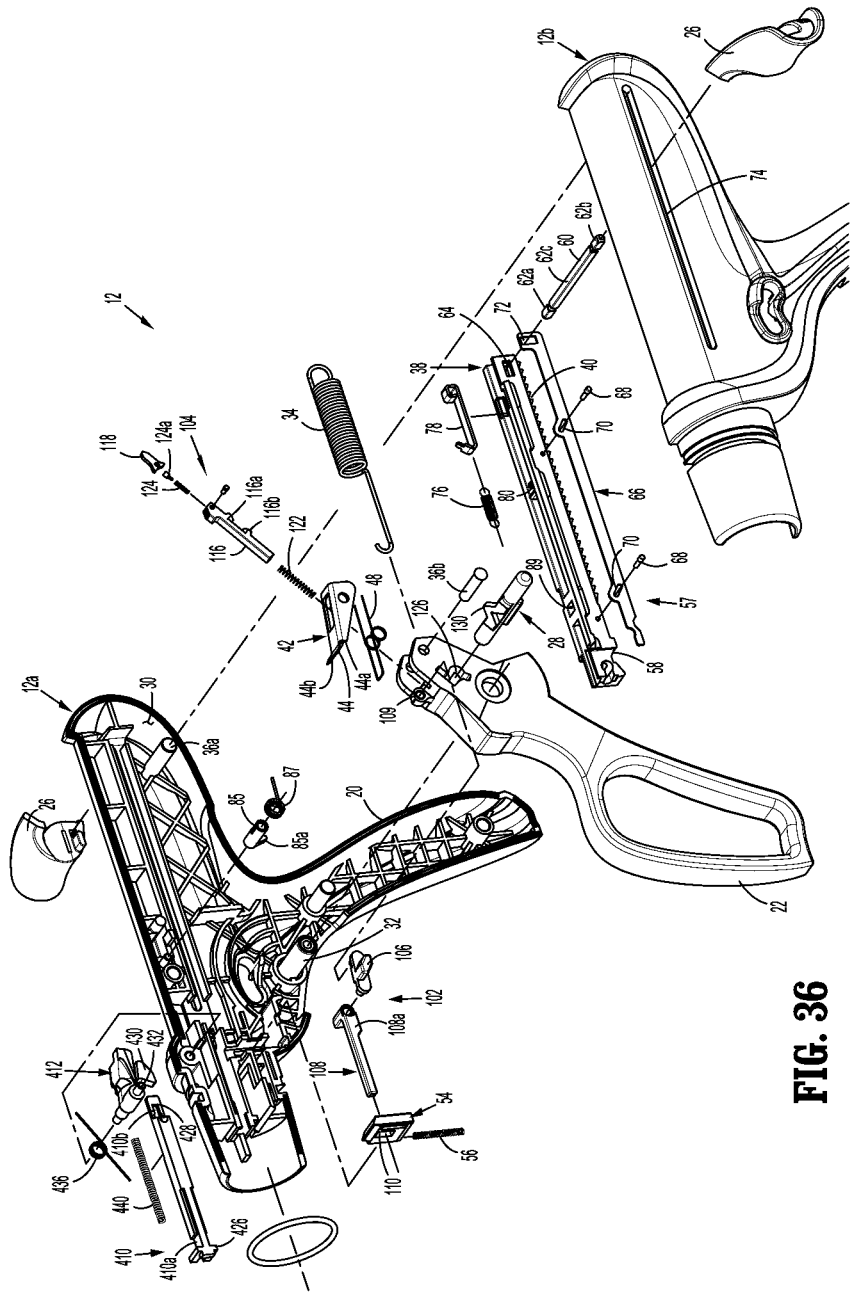
FIG. 36 is a perspective view of the handle assembly of the stapler shown with parts separated.
Figure 46:
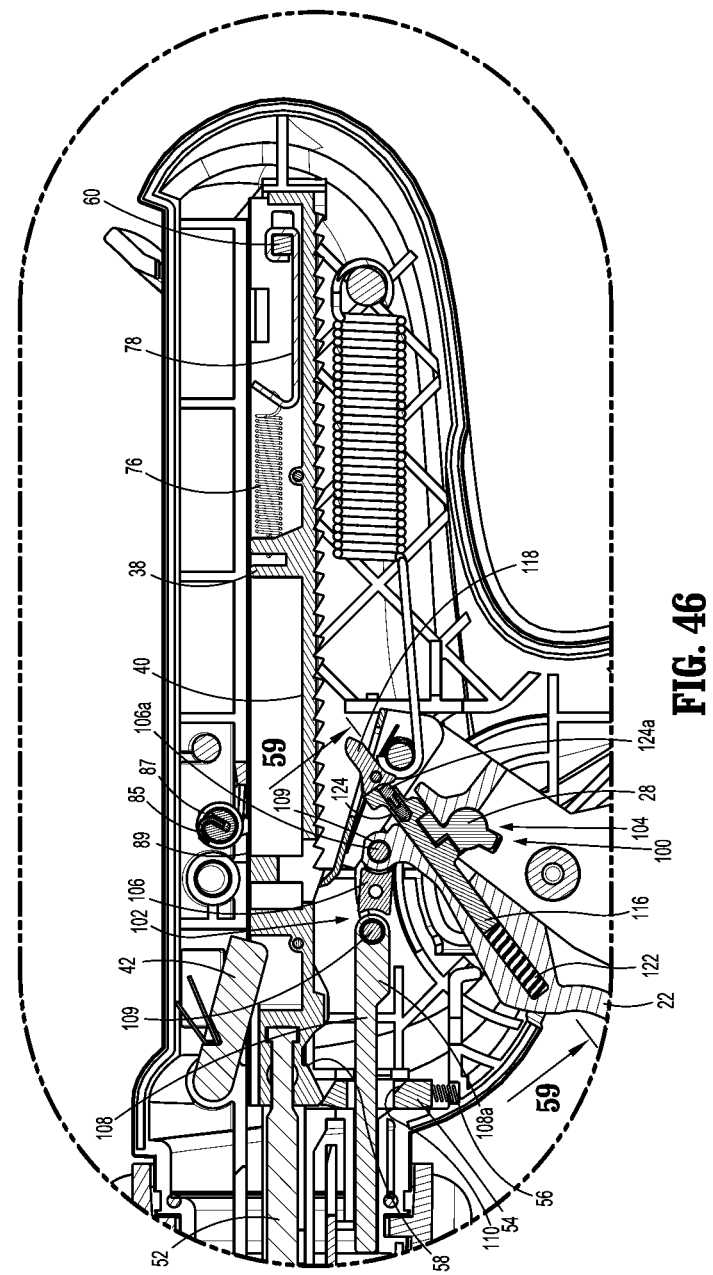
FIG. 46 is an enlarged view of the indicated area of detail of FIG. 45.

Referring to FIGS. 36 and 46, handle assembly 12 includes a retraction arm 85 which is rotatably supported within barrel portion 24 of handle assembly 12. A torsion spring 87 is positioned to urge retraction arm 85 in counter-clockwise rotation as viewed in FIG. 46. Retraction arm 85 includes a protrusion 85a which is positioned within a notch 89 of actuation shaft 38. As spring 87 urges arm 85 in counter-clockwise rotation, protrusion 85a engages actuation shaft 38 to urge actuation shaft 38 proximally within handle assembly 12.

Referring still to FIGS. 36 and 46, handle assembly 12 of stapler 10 includes a grasper jaw mechanism 100 which includes a disconnect link assembly 102 and an actuator assembly 104. As will be discussed in further detail below, disconnect link assembly 102 functions to prevent engagement of vertical pawl 54 with actuation shaft 38 when handle assembly 12 is in the grasper mode, allowing for proximal and distal movement of actuation shaft 38 to move anvil assembly 506 relative to cartridge assembly 516 between the open and clamped positions only (not for firing drive assembly 590). Actuator assembly 104 prevents the movable handle 22 from returning fully to the non-compressed position when handle assembly 12 is in grasper mode to prevent driving pawl 42 from engaging toothed rack 40. By doing this, operation of movable handle 22 is prevented from advancing actuation shaft 38 distally beyond the clamped position of SULU 500 (FIG. 1) when handle assembly 12 is in the grasper mode, thus preventing firing of the drive assembly 590 (FIG. 10).

Disconnect link assembly 102 includes a proximal link 106 and a distal link 108. Proximal link 106 has a proximal end pivotally secured to a cylindrical boss 109 formed on movable handle 22 about a pivot member 106a and a distal end pivotally secured to a proximal end of distal link 108 via a pivot member 109. Distal link 108 is linearly slidable along a track defined within housing cavity 30 of handle assembly 12 and includes an angled stepped portion 108a formed at its proximal end. Distal link 108 is slidably positioned to engage a cam surface 110 formed on vertical pawl 54. As discussed above, vertical pawl 54 is urged upwardly by a biasing member 56 into engagement with a cutout 58 (FIGS. 39 and 40) formed in actuation shaft 38 to prevent movement of actuation shaft 38 after SULU 500 (FIG. 1) has been moved to a clamped position. When stepped portion 108a of distal link 108 is moved distally into engagement with cam surface 110 of vertical pawl 54 by moving movable handle 22 towards stationary handle 20, vertical pawl 54 is moved downwardly against the bias of biasing member 56 out of engagement with cutout 58 of actuation shaft 38. When this occurs, actuation shaft 38 is free to move proximally as will be discussed in further detail below.

Figure 58:
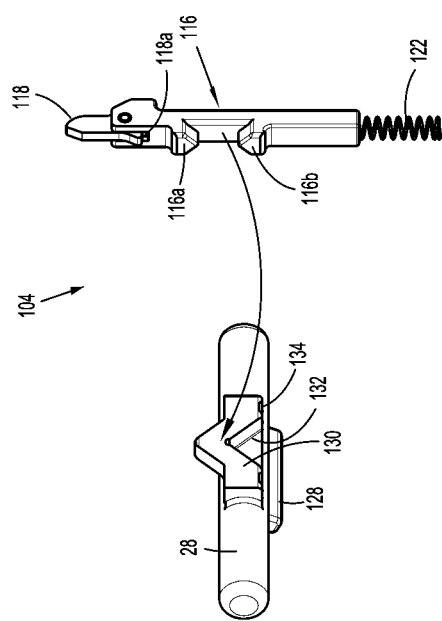
FIG. 58 side view of the actuator assembly of the handle assembly shown with parts separated.
Figure 61:
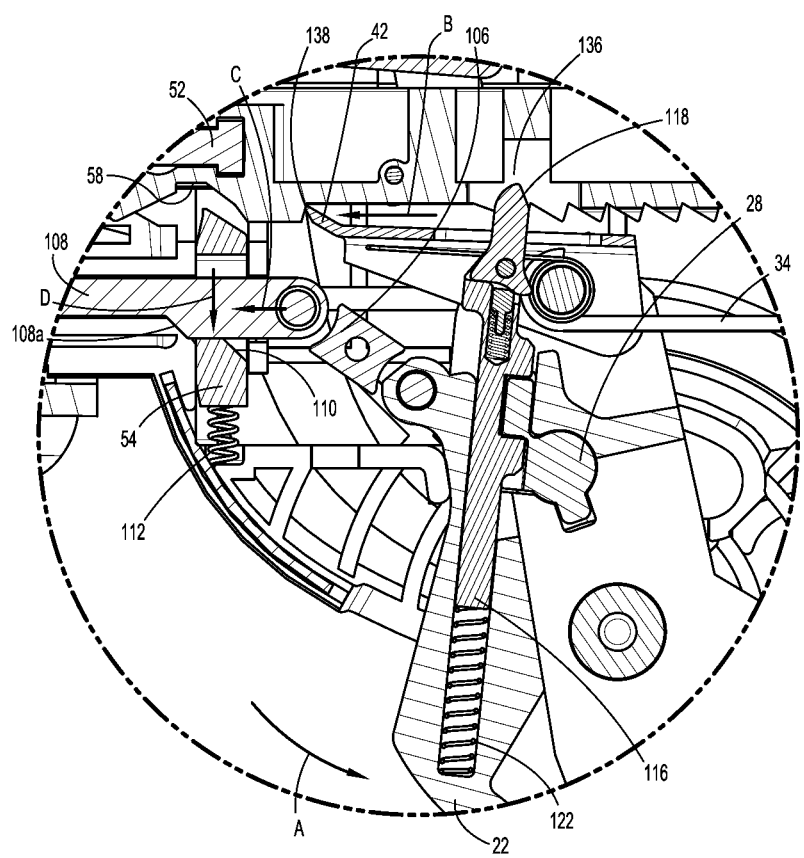
FIG. 61 is an enlarged view of the indicated area of detail of FIG. 60.
Figure 74:
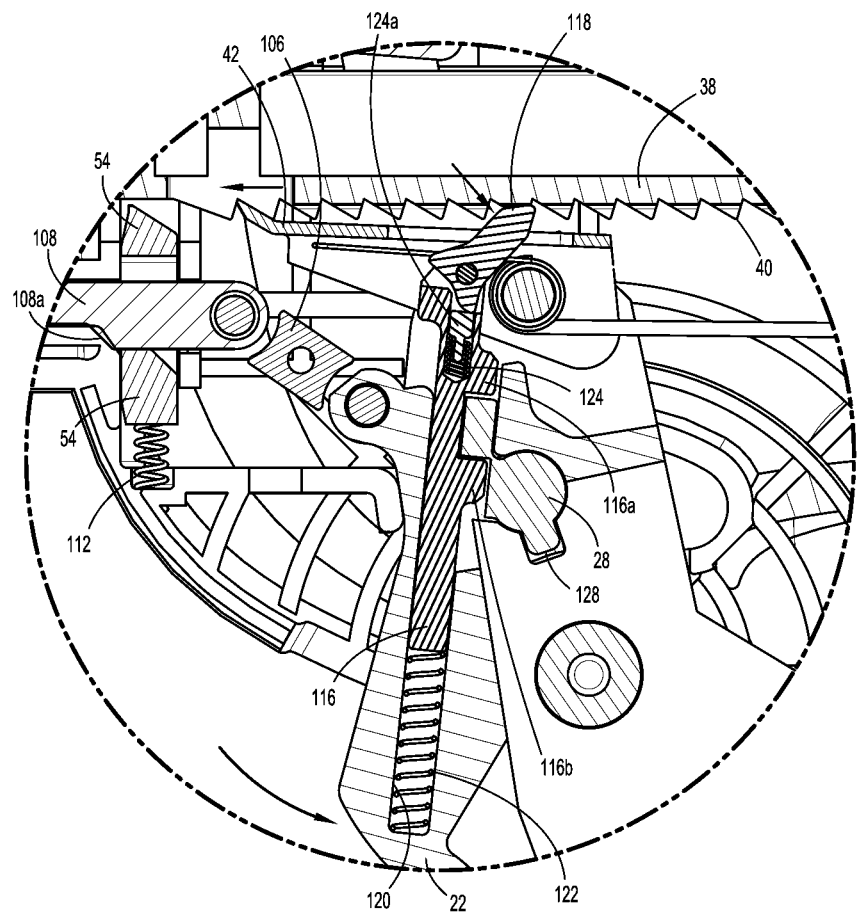
FIG. 74 is a longitudinal, cross-sectional view of the actuation assembly in the firing mode with the movable handle in the compressed position and the toothed rack translated distally.
Figure 80:
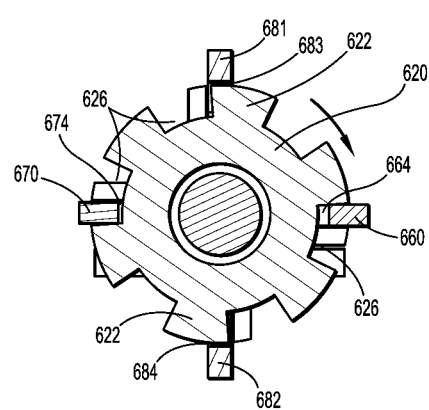
FIG. 80 is a cross-sectional view taken along section line 80-80 of FIG. 79.
Figure 85:
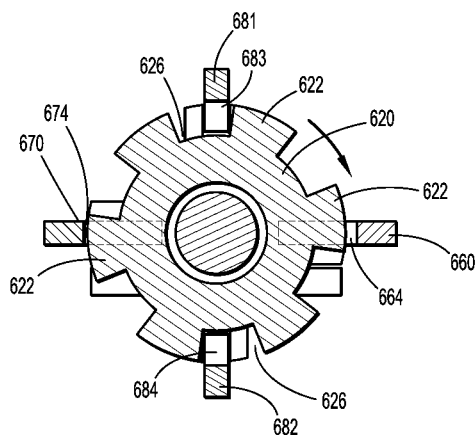
FIG. 85 is a cross-sectional view taken along section line 85-85 of FIG. 84.
Figure 86:
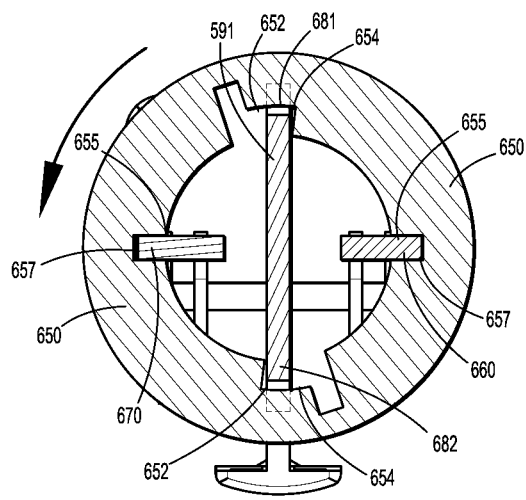
FIG. 86 is a transverse, cross-sectional view of the lock ring of the fire and reload assembly shown in a second position.

Referring also to FIG. 58, actuator assembly 104 includes actuator button 28, a pawl arm 116 and a grasping pawl 118. As will be described in greater detail below, actuator button 28 is selectively movable between a centered position and an off-centered position for transitioning handle assembly 12 of stapler 10 between the grasper mode and the firing mode. Pawl arm 116 is slidably received in a recess 120 (FIG. 46) formed in movable handle 22. A biasing member 122 is positioned within recess 120 to urge pawl arm 116 towards an extended position (FIG. 61). Pawl arm 116 has upper and lower spaced triangular cam surfaces 116a and 116b which will be discussed in further detail below. Grasping pawl 118 is pivotally supported within a slot 118a (FIG. 58) formed in a distal end of pawl arm 116. A biasing member 124 (FIG. 36) is positioned to urge a piston 124a into grasping pawl 118 to urge grasping pawl 118 in a counter-clockwise direction as viewed in FIG. 74. Pivoting movement of grasping pawl 118 allows pawl arm 116 to ratchet or slide over toothed rack 40 of actuation shaft 38 (FIG. 74).

Figure 59:
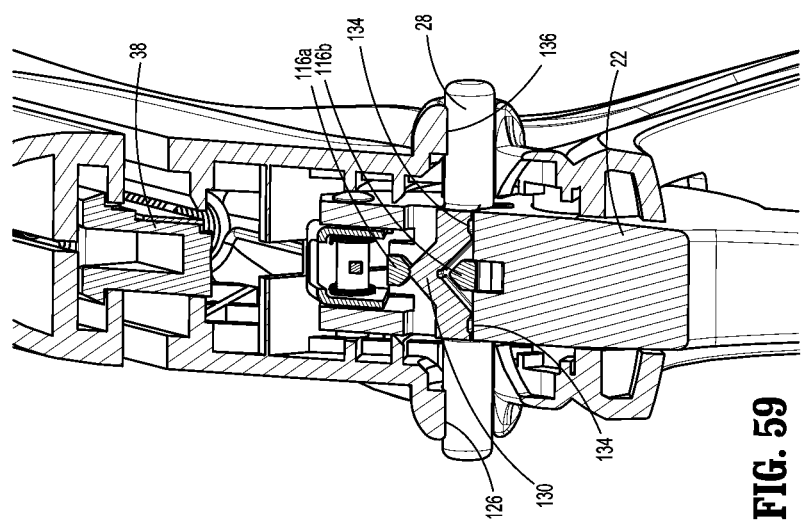
FIG. 59 is a transverse, cross-sectional view of a portion of the handle assembly illustrating the actuator assembly in the grasper mode.

Referring also to FIG. 59, actuator button 28 is slidably positioned through a bore 126 (FIG. 36) formed in movable handle 22 from a centered position (FIG. 59) to an off-center position (FIG. 70). Bore 126 is substantially orthogonal to recess 120 such that actuator button 28 is slidably positioned between upper and lower cam surfaces 116a and 116b of pawl arm 116. Actuator button 28 is substantially cylindrical and includes a linear rib 128 and a V-shaped cam member 130. V-shaped cam member 130 defines a slot 132 (FIG. 58) which is configured to receive lower cam surface 116b of pawl arm 116 when actuator button 28 is in the centered position and pawl arm 116 is in an extended position within recess 120. Actuator button 28 defines recesses 134 (FIG. 59) on opposite sides of slot 132. Opposite ends of actuator button 28 extend from opposite sides of housing sections 12a and 12b of handle assembly 12 (FIG. 59) and can be pressed by a surgeon from either side of handle assembly 12 to move actuator button 28 linearly through bore 126 in either direction to move actuator button 28 from the centered position to the off-center position. When actuator button 28 is moved linearly within bore 126, lower cam surface 116b is engaged by V-shaped cam member 130 to urge pawl arm 116 from its initial, extended position, downwardly within recess 120 to its retracted position. When actuator button 28 is moved linearly to its off-center position and pawl arm 116 is cammed to its retracted position, the apex of lower cam surface 116b is received within one of recesses 134 to retain actuator button 28 in the off-centered, or actuated position (see FIG. 70). When pawl arm 116 is moved to the retracted position, grasping pawl 118 is also moved from an initial extended position, to a retracted position and is withdrawn from a slot 136 of actuation shaft 38 (FIG. 40).

Figure 49:
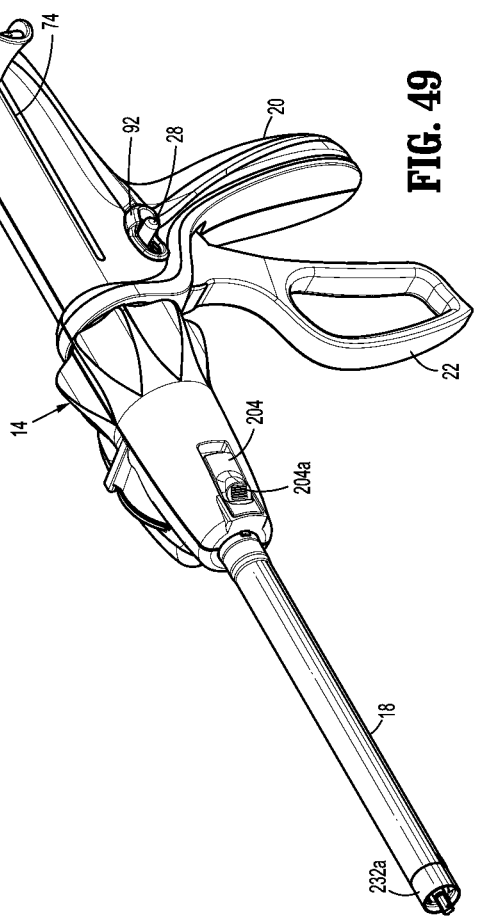
FIG. 49 is a front, perspective view of the stapler absent the SULU.
Figure 52:
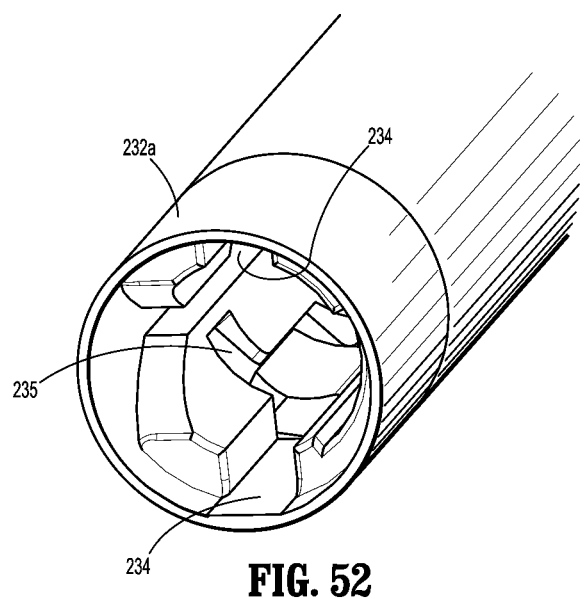
FIG. 52 is a front, perspective view of the distal end of the elongated body shown in the disengaged position.
Figure 67:
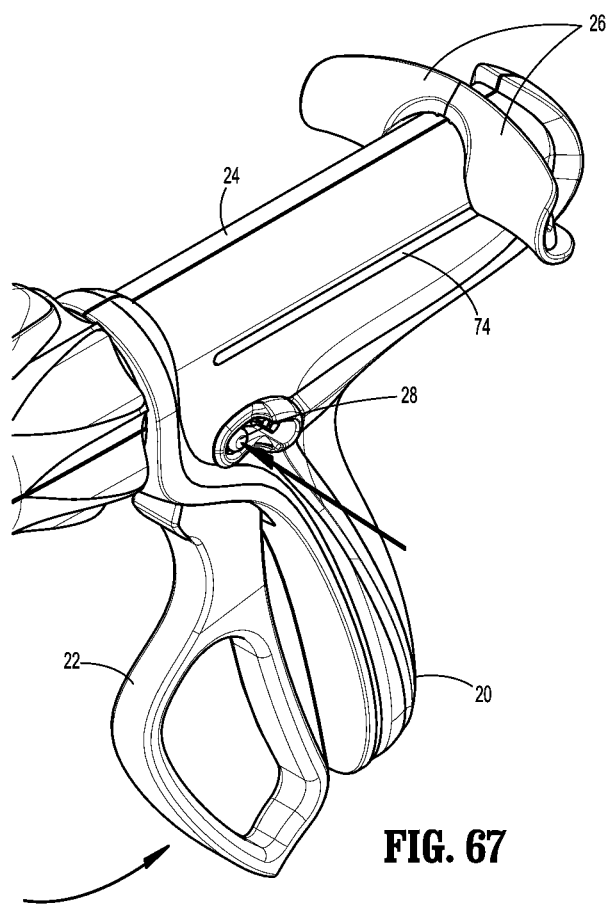
FIG. 67 is a perspective view of the handle assembly illustrating the actuator assembly transitioning to the firing mode.
Figure 68:
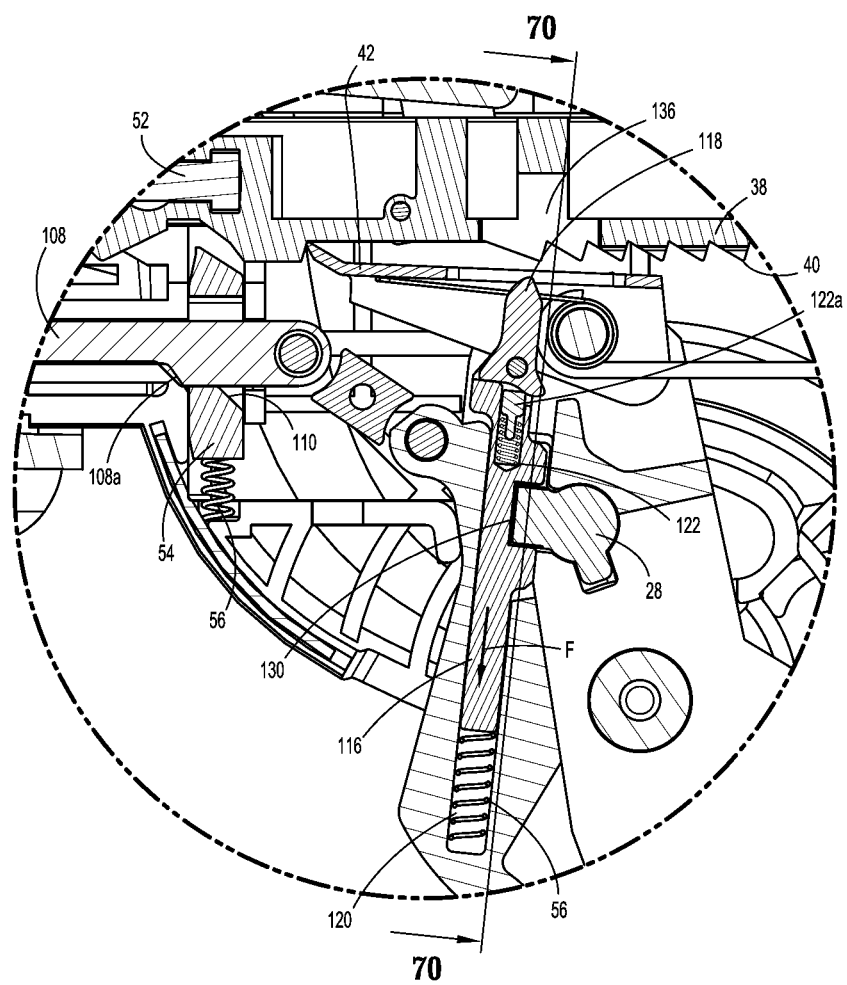
FIG. 68 is a longitudinal, cross-sectional view of the actuator assembly showing the movable handle in the compressed position and the actuator assembly transitioning to the firing mode.

Referring to FIGS. 1, 49 and 67, actuator button 28 is supported on movable handle 22 and extends through each of housing sections 12a and 12b of handle assembly 12. In order to facilitate movement of actuator button 28 with movable handle 22, arc shaped slots 90 are provided in each of housing sections 12a and 12b. Raised surfaces or bosses 92, are provided about a portion of arc shaped slots 90 to prevent depression of actuator button 28 until movable handle 22 has been moved to a compressed position.

Figure 41:
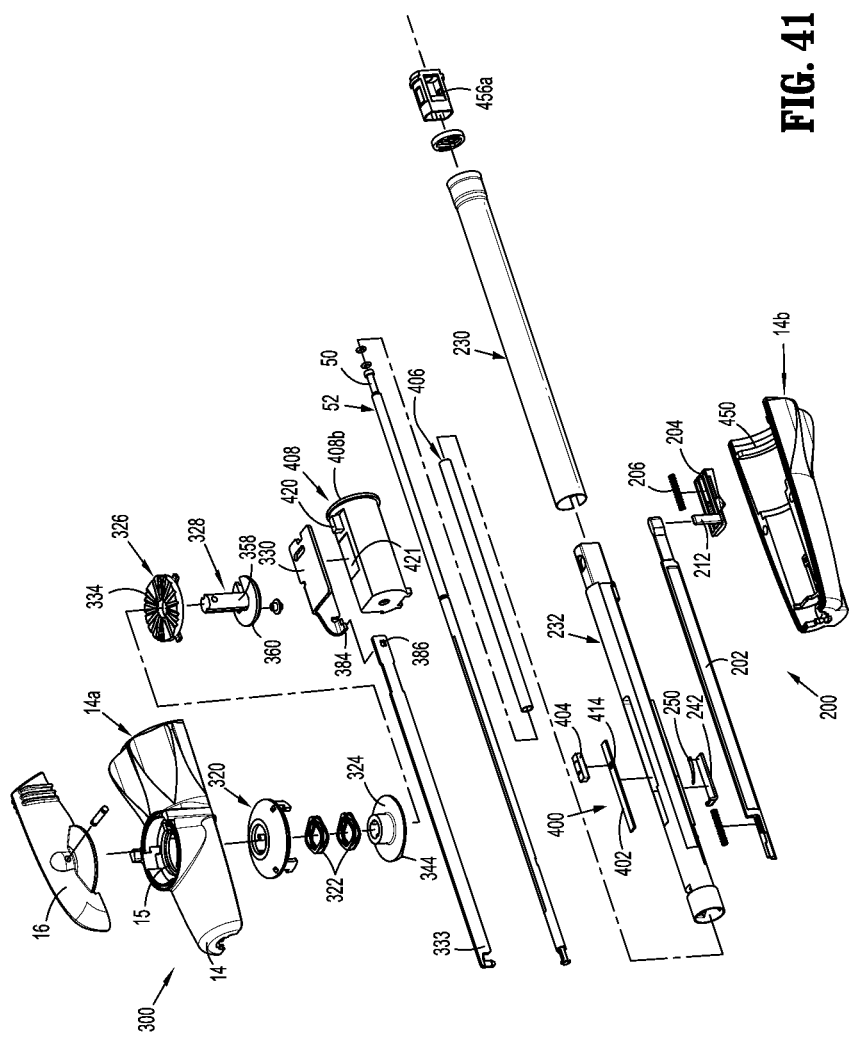
FIG. 41 is a front, perspective view of the elongated body portion of the stapler shown with parts separated.
Figure 43:
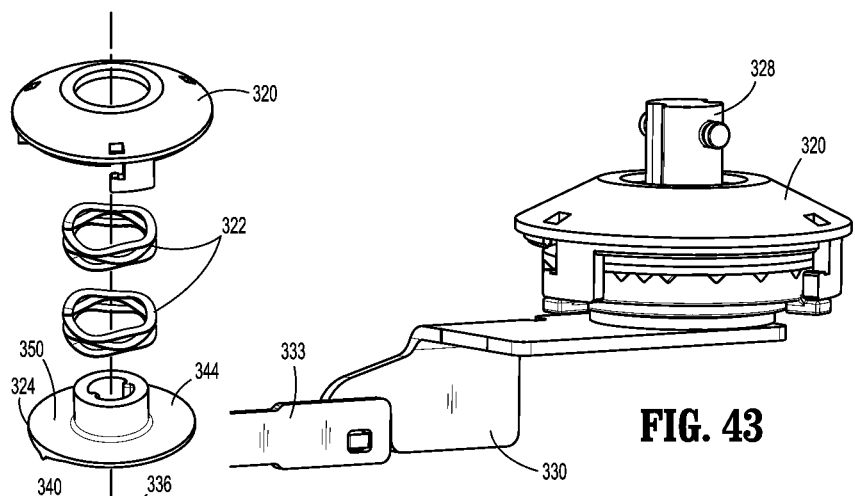
FIG. 43 is a side view of the clutches of the articulation assembly.
Figure 47:
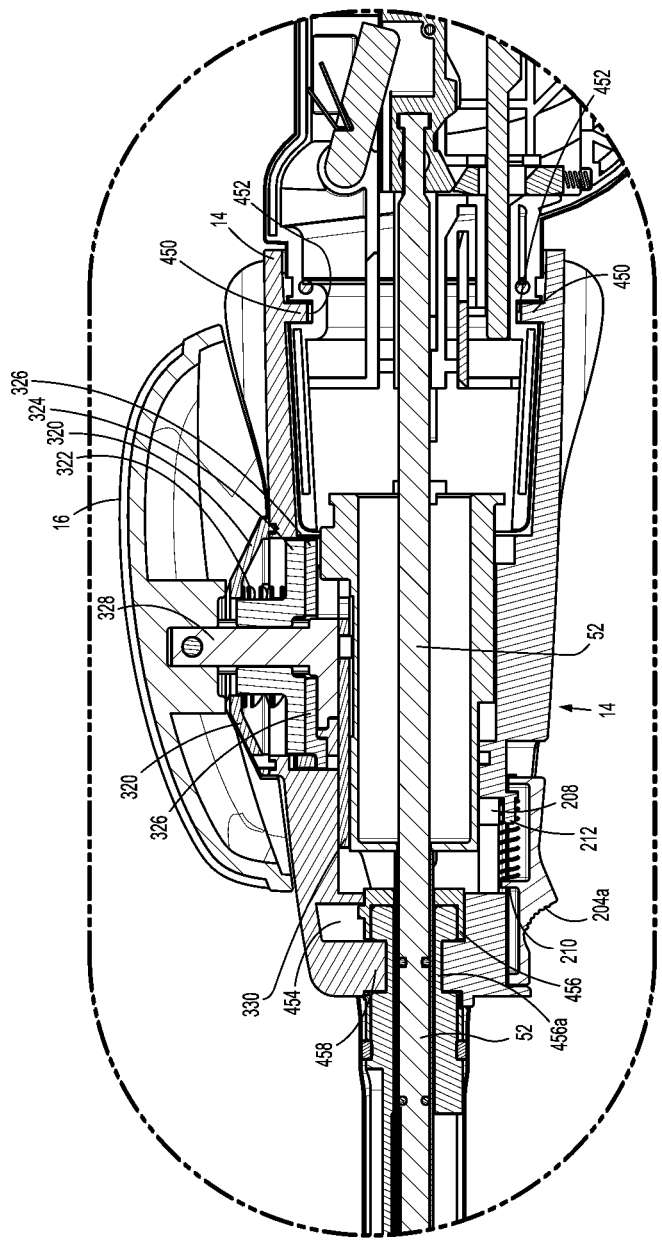
FIG. 47 is an enlarged view of the indicated area of detail of FIG. 45.
Figure 48:
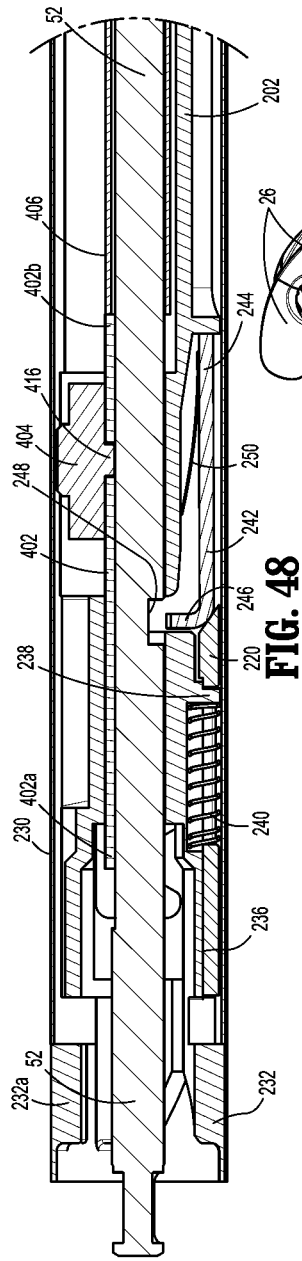
FIG. 48 is an enlarged view of the indicated area of detail of FIG. 45.

Referring to FIGS. 36, 41 and 47, rotation knob 14 is constructed from molded half-sections 14a and 14b. Each half-section 14a, 14b includes an internal annular projection 450 on its proximal end which is received within an annular recess 452 formed in the distal end of handle assembly 12 to rotatably secure rotation knob 14 to handle assembly 12. A distal end of each mold half-sections 14a and 14b defines a recess 454 (FIG. 47) for non-rotatably receiving a fitting 456. Fitting 456 includes cutouts 456a for receiving a projection 458 (FIG. 47) formed on half-sections 14a and 14b. Fitting 456 is fixedly secured to the proximal end of body 18 such that rotation of rotation knob 14 effects rotation of body 18 and, thus, SULU 500 (FIG. 1).

Referring to FIGS. 41-44 and 47, articulation mechanism 300 is supported in a receptacle 15 formed in rotatable knob 14 (FIG. 41) and is configured to articulate an articulatable SULU. Although SULU 500 (FIG. 1) is not shown including articulation features, it is envisioned that SULU 500 (FIG. 1) include articulation features configured to articulate SULU 500 (FIG. 1) in response to the operation of articulation mechanism 300, i.e., upon rotation of articulation lever 16. Alternatively, stapler 10 may be configured as a cross-compatible device that is usable with articulating SULUs as well as non-articulating SULUs. When used with non-articulating SULU, articulation assembly 300 would simply be inoperable.

Figure 44:
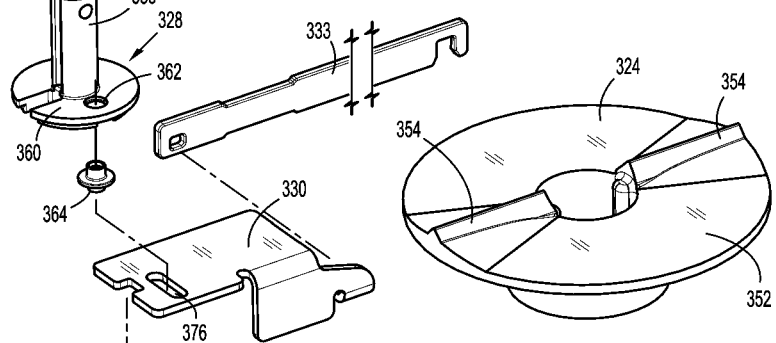
FIG. 44 is a bottom, perspective view of the upper clutch of the articulation assembly.
Figure 42:
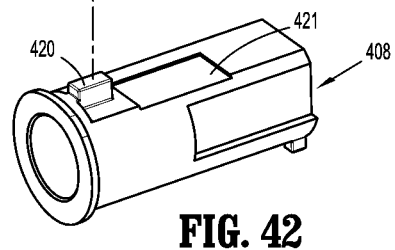
FIG. 42 is an enlarged, perspective view of the articulation assembly of the shaft assembly.
Figure 45:
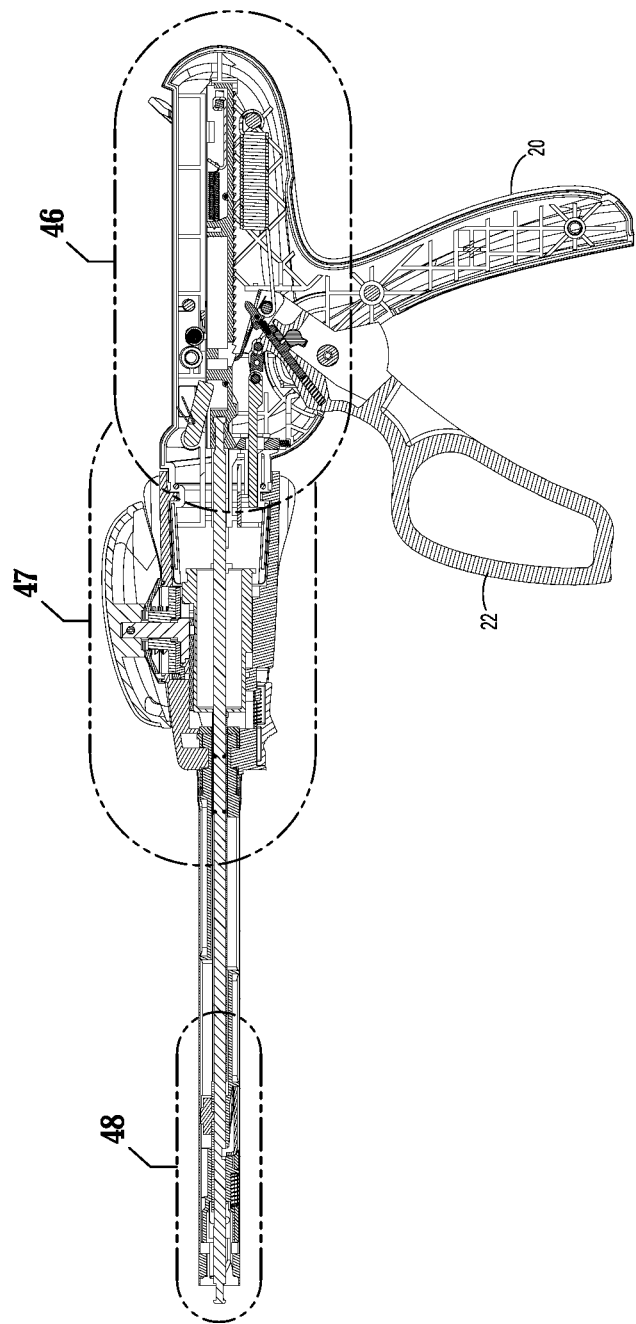
FIG. 45 is a longitudinal, cross-sectional view of the stapler shown in the original position and absent the SULU.

Articulation mechanism 300 includes articulation lever 16, a mechanism cover 320, biasing members 322, an upper clutch 324, a lower clutch 326, a main shaft 328, and a translation member 330. Lower clutch 326 is rotatably fixed within receptacle 15 and includes a circular serrated portion 334 having a series of shallow serrations 336 and a pair of spaced deep serrations 338 (FIG. 42). Lower clutch 326 also defines a central throughbore 340 which is dimensioned to receive main shaft 328. Upper clutch 324 is rotatably fixed to main shaft 328 and includes a base portion 344 having an upper face 350 and a lower face 352 (FIG. 44). Lower face 352 includes a plurality of spaced projections 354 which are received within deep and shallow serrations 336 and 338 of lower clutch 326. Biasing members 322 urge lower face 352 of upper clutch 324 into engagement with serrated portion 334 of lower clutch 326 to releasably secure articulation mechanism 300 in a fixed position and, thus, to releasably secure the articulatable SULU at a fixed angle of articulation.

Main shaft 328 includes a substantially cylindrical body portion 358 and a disc-shaped base portion 360. Base portion 360 defines an opening 362 which receives a cam member 364. Body portion 358 is dimensioned to extend through both lower clutch 326 and upper clutch 324 such that base portion 360 is positioned beneath upper clutch 324 and lower clutch 326 within receptacle 15 of rotation knob 14. Translation member 330 (FIG. 42) includes a cam slot 376 dimensioned to slidably receive cam member 364 of main shaft 328.

When articulation lever 16 is rotated, base portion 344 of upper clutch 324 is rotated in relation to serrated portion 334 of lower clutch 326 to urge upper clutch 324 upwardly against the bias of biasing members 322, disengaging projections 354 from serrations 336 or 338 and allowing rotation of upper clutch 324 and main shaft 328. Thereafter, biasing member 322 urges upper clutch 324 downwardly to urge projections 354 back into engagement with the next serration (FIG. 41). Projections 354 are positioned to be received within deep serrations 338 when the SULU is in its non-articulated position to provide increased resistance to movement of the SULU from its non-articulated position. Rotation of articulation lever 16 also effects rotation of cam member 364 in relation to translation member 330. When cam member 364 is driven in rotation, translation member 330 is urged to move linearly. Translation member 330 is configured to engage an articulation link 333 of an articulatable SULU such that linear movement of translation member 330 effects linear movement of the articulation link 333 to effect articulation of the articulatable SULU.

Referring to FIGS. 34, 37, 38, 41 and 47-57, stapler 10 includes a SULU release link assembly 200 which includes a SULU release link 202, a SULU release button 204 and a biasing member 206. Release button 204 includes a gripping surface 204a and is slidably positioned within a cavity 208 formed in rotation knob 14 (FIG. 47). Release button 204 includes a central wall 210 and a transversely extending post 212. Biasing member 206 is positioned between a proximal surface of central wall 210 and a spring post 214 formed on rotation knob 14 to urge release button 204 distally within cavity 208.

Figure 37:
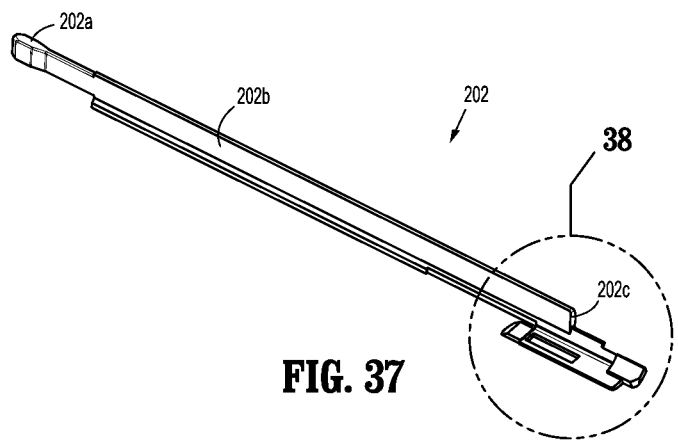
FIG. 37 is a perspective view of the SULU release link of the shaft assembly.
Figure 38:
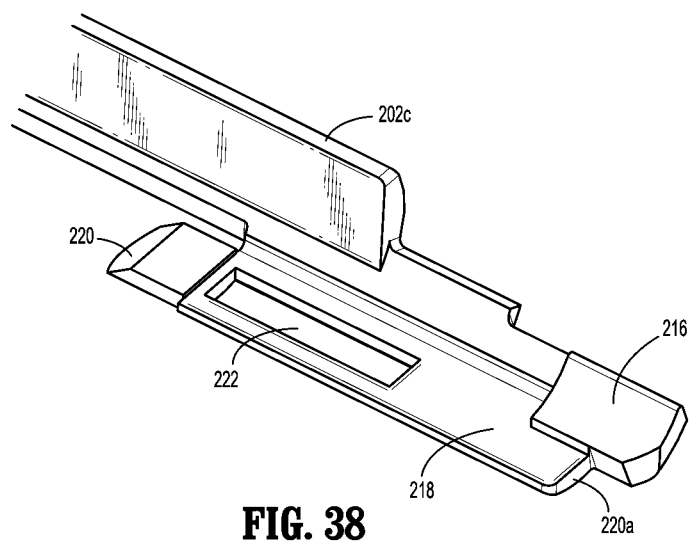
FIG. 38 is an enlarged view of the indicated area of detail of FIG. 37.

Referring to FIGS. 37 and 38, release link 202 includes a proximal end 202a, an elongated central body portion 202b and a distal end 202c. Proximal end 202a defines a blind bore (not shown) dimensioned to receive post 212 of release button 204 (FIG. 34) such that biasing member 206 urges button 204 and link 202 in a distal direction. Distal end 202c of release link 202 includes a distal abutment member 216 and a transverse extension 218. A proximal end of transverse extension 218 defines a ramped cam surface 220 and a distal end of transverse extension 218 defines a tab retention recess 220 with abutment member 216. Transverse extension 218 also includes a rectangular opening 222.

Referring to FIGS. 41 and 47-57, elongated body portion 18 of stapler 10 includes an outer tube 230 and an inner body portion 232 through which control rod 52 is inserted. Inner body 232 is received within outer tube 230 and includes a distal end 232a defining a pair of diametrically-spaced longitudinal channels 234 (FIG. 52) and proximally-spaced annular channel 235 which intersects longitudinal channels 234. Inner body 232 also defines a recess 236 (FIG. 48) for slidably receiving release link 202 such that release link is slidably positioned between outer tube 230 and inner body portion 232. A projection 238 extending radially outwardly from body 232 extends into rectangular opening 222 of transverse extension 218 of release link 202. A spring 240 is positioned within rectangular opening 222 between projection 238 and a distal end of opening 222 (FIG. 38) to urge release link 202 distally.

A hook 242 is positioned between outer tube 230 and inner body portion 232 adjacent ramped cam surface 220. Hook 242 includes an elongated body 244 having a transverse distal end 246. Transverse distal end 246 is positioned adjacent to a cutout 248 in control rod 52. Hook 242 is urged by a biasing member 250 to a position in which distal end 246 of hook 242 is located externally of cutout 248. When release link 202 is moved proximally against the urging of biasing members 206 and 240 by pulling release button 204 proximally, cam surface 220 moves distal end 246 of hook 242 into cutout 248 of control rod 52. If control rod 52 is not in its retracted position shown in FIG. 48 and notch 248 is not positioned to receive distal end 246 of hook 242, cam surface 220 will not be able to move hook 242 inwardly and link 202 will not be able to move proximally. Thus, a SULU cannot be removed or installed if control rod 52 is not in the retracted position.

Figure 53:
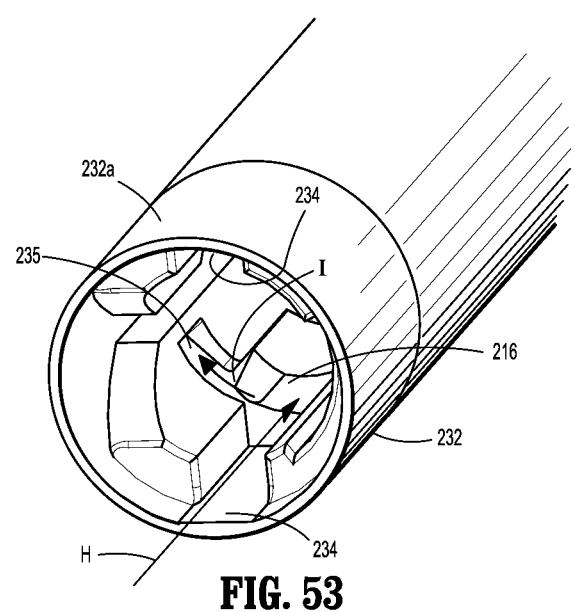
FIG. 53 is a front, perspective view of the distal end of the elongated body shown in the engaged position.

Referring to FIGS. 50-57, in order to fasten a SULU 500 to elongated body 18 of stapler 10, tabs 260 must be aligned with and advanced through longitudinal channels 234 of inner body 232 in the direction indicated by arrow "H" in FIG. 53 and rotated into annular channel 235 in the direction indicated by arrow "I". As discussed above, abutment member 216 is positioned to engage a tab 260 as tab 260 exits longitudinal channel 234. When tab 260 engages abutment member 216 of release link 202, release link 202 moves proximally in the direction indicated by arrow "J" in FIG. 51 against the urging of biasing members 206 and 240 until tab 260 is positioned entirely within annular channel 235. As this occurs, hook 242 is moved by cam surface 220 into cutout 248 of control rod 52. When tab 260 is positioned entirely within annual channel 235, SULU 500 is rotated in relation to elongated body portion 18 in the direction indicated by arrow "K" in FIG. 56 such that tabs 260 move out of alignment with longitudinal channels 234 (FIG. 56). When this occurs, release link 202 is returned to its distal position in the direction indicated by arrow "L" in FIG. 57 such that a tab 260 is retained within tab retention recess 220a. When tab 260 is positioned within tab retention recess 220a, SULU 500 is prevented from rotating in relation to body portion 18 and, thus, is locked onto body portion 18.

In order to remove SULU 500 from body portion 18, SULU release button 204 is moved proximally (FIG. 50) in the direction indicated by arrow "M" in FIG. 50 to retract abutment member 216 proximally and remove tab 260 from tab retention recess 220a. When tab 260 clears recess 220a, SULU 500 can be rotated to align tabs 260 with longitudinal channels 234 and SULU 500 can be detached from body portion 18.

Stapler 10 also includes a sensor mechanism 400 for preventing operation of stapler 10 before a SULU 500 has been attached to body portion 18 of stapler 10. Referring to FIGS. 36, 41, 48, and 50, sensor mechanism 400 includes a first link 402, a spacer 404, a connecting tube 406, an articulation locking member 408, a second link 410, and an actuation shaft locking member 412. First link 402 includes a plate-like member which is supported between control rod 52 and inner body portion 232 of elongated body portion 18 of the stapler 10 on a flat surface which is ground into control rod 52. Prior to attachment of SULU 500 to elongated body portion 18, the distal end 402a (FIG. 48) of first link 402 is positioned to engage the proximal end of SULU 500 when a SULU 500 is attached to body portion 18. First link 402 includes a hole 414 (FIG. 41) which is dimensioned to receive a protrusion 416 (FIG. 48) formed on spacer 404. spacer 404 fits between first link 402 and an inner surface of outer tube 230 with a slight interference. Spacer 404, link 402 and the flat surface on control rod 52 function together to prevent control rod 52 from rotating in housing 232. This ensures proper rotational alignment between hook 242 and notch 248 in control rod 52. The proximal end 402b of first link 402 abuts the distal end of connecting tube 406 such that linear movement of first link 402 effects linear movement of sensor tube 406.

Connecting tube 406 is slidably positioned about control rod 52 and has a proximal end 406a which abuts a distal face 408a of locking member 408 (FIG. 50). Locking member 408 is also slidably positioned about control rod 52. When connecting tube 406 is moved proximally by first link 402, locking member 408 is also moved proximally. Lock member 408 is substantially cylindrical and includes a lock tab 420, an upper flat 421 for supporting translation member 330 of articulation mechanism 300.

Second link 410 (FIG. 36) has a distal end 410a positioned to engage the proximal end 408b of locking member 408 and a proximal end 410b positioned to engage locking member 412. Distal end 410a of second link 410 includes an enlarged head 426 positioned to abut the proximal face of locking member 408. Proximal end 410b includes a stepped portion 428 which is positioned to engage a wing 430 formed on locking member 412. A biasing member 440 urges second link 410 distally out of engagement with locking member 412.

Locking member 412 is pivotally secured within handle assembly 12 between housing sections 12a and 12b about pivot member 432. A biasing member 436 urges locking member 412 into a slot 434 (FIG. 40) formed in actuation shaft 38 to lock actuation shaft 38 in its retracted position. When locking member 408 is moved proximally to move second link 410 proximally, proximal end 410b of second link 410 engages wing 430 of locking member 412 to disengage locking member 412 from actuation shaft 38 to allow for distal movement of actuation shaft 38.

Prior to attachment of SULU 500 to stapler 10, locking member 412 is positioned in slot 434 of actuation shaft 38 to prevent movement of shaft 38. When SULU 500 is inserted into distal end 232a of inner body 232 (FIG. 48), the proximal end of SULU 500 engages first link 402 and moves first link 402, connecting tube 406, locking member 408 and second link 410 proximally. When second link 410 moves proximally, proximal end 410b of link 410 engages wing 430 of locking member 412 to pivot locking member 412 from within slot 434 of actuation shaft 38 to unlock actuation shaft 38.

Figure 60:
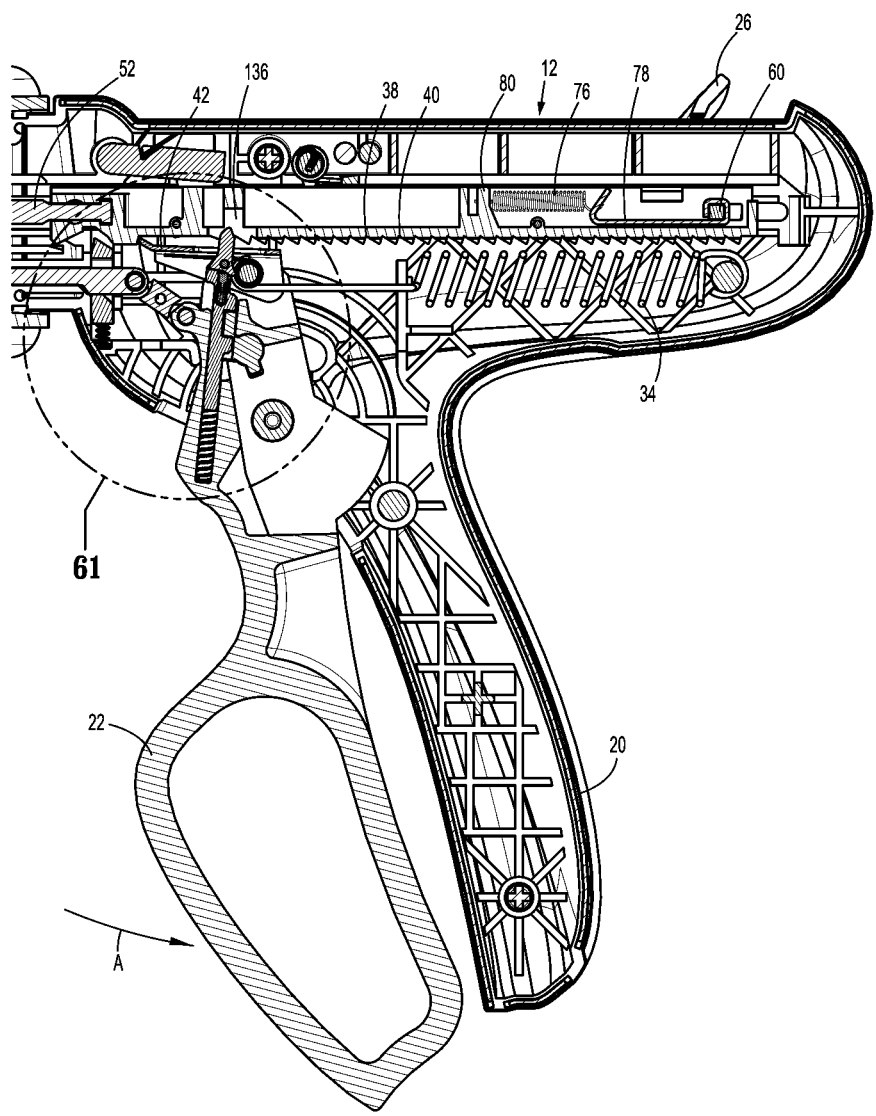
FIG. 60 is a longitudinal, cross-sectional view of the handle assembly with the movable handle in the compressed position, in the grasper mode.

The use and operation of stapler 10 is described with reference to FIGS. 59-91. Initially, fire and reload assembly 600 is disposed in the firing mode, wherein drive bar 591 is engaged to rotary coupler 620 (see FIGS. 30-31 and 63-64). With reference to FIGS. 59-61, with actuator button 28 is in its centered position, as mentioned above, pawl arm 116 is urged to its extended position by biasing member 122. When pawl arm 116 is in the extended position, grasping pawl 118 is positioned to extend into a slot 136 (FIG. 61) formed in actuation shaft 38. This position corresponds to the grasper mode of handle assembly 12. Thus, when movable handle 22 is actuated in the direction indicated by arrow "A" in FIG. 60, driving pawl 42 engages an abutment 138 on actuation shaft 38 (FIG. 61) to advance the actuation shaft 38 distally in the direction indicated by arrow "B" in FIG. 61 to move control rod 52 distally. Distal translation of control rod 52, in turn, translates rotary coupler 620 distally, which urges drive bar 591 and dynamic clamping member 593 distally to move SULU 500 to the clamped position, as described above. In this grasper mode, because vertical pawl 54 is disengaged from actuation shaft 38, movable handle 22 may be returned to the non-compressed position to return control rod 52 proximally, thus translating drive bar 591 proximally and returning SULU 500 to the unclamped position (FIG. 3).

Compression of movable handle 22 towards stationary handle 20 and return of movable handle 22 to a non-compressed position spaced from stationary handle 20 when handle assembly 12 is in the grasper mode effects clamping and unclamping, respectively, of SULU 500. More specifically, with additional reference to FIGS. 63-66, control rod 52 is advanced partially distally upon compression of movable handle 22 towards stationary handle 20 such that rotary coupler 620 is urged partially distally, thus urging drive bar 591 distally such that upper beam 593a of dynamic clamping member 593 is advanced into the upper transverse portion of T-shaped channel 509, distal beam 593b is translated along the exterior of frame member 516 and central support member 531, and upright member 593c is translated into channel 574 to pivot anvil assembly 506 relative to cartridge assembly 514 to the clamped position (see FIGS. 3-6). This partial advancement of drive bar 591 may correspond to about a 15 mm increment of drive bar 591, although other incremental distances are also contemplated depending on the configuration of the SULU. Upon return of movable handle 22 to the non-compressed position, control rod 52 is returned proximally such that rotary coupler 620 is returned proximally. Proximal translation of rotary coupler 620 effects proximal translation of drive bar 591 (e.g., about 15 mm in the proximal direction) such that upper beam 593a is removed from the upper transverse portion of T-shaped channel 509, distal beam 593b is translated proximally of the exterior of frame member 516 and central support member 531, and upright member 593c is removed from channel 574 to pivot anvil assembly 506 relative to cartridge assembly 514 back to the unclamped position (see FIGS. 3-6).

Referring in particular to FIGS. 63-64, with rotary coupler 620 only translating partially distally (e.g., a 15 mm increment) and subsequently returning proximally, rotary coupler 620 remains proximal of distal cam 640 and, thus, fire and reload assembly 600 remains disposed in the firing mode as handle assembly 12 is repeatedly compressed and released while in the grasper mode. That is, with handle assembly 12 in the grasper mode, anvil assembly 504 is repeatedly pivotable between the open position (FIG. 3) and the clamped position (FIG. 4), as described above, without transitioning fire and reload assembly 600 to the reload position.

Referring again to FIGS. 59-61, as movable handle 22 is compressed towards stationary handle 20 in the grasper mode, distal link 108 is also moved distally in the direction indicated by arrow "C" in FIG. 61 such that stepped portion 108a of distal link 108 engages cam surface 110 of vertical pawl 54 to urge vertical pawl 54 downwardly in the direction indicated by arrow "D" in FIG. 61 against the bias of spring 112 away from cutout 58 of actuation shaft 38.

Figure 62:
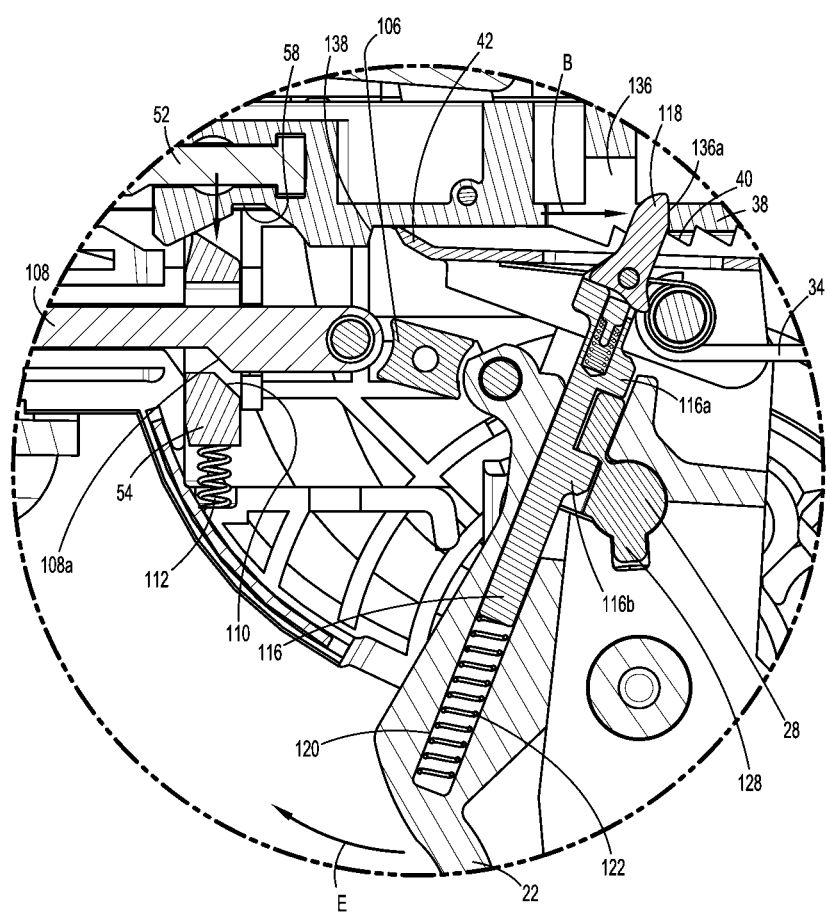
FIG. 62 is a longitudinal, cross-sectional view illustrating the movable handle returning to the original position in the grasper mode.

Referring also to FIG. 62, when movable handle 22 is returned to its non-compressed position in the direction indicated by arrow "E" in FIG. 62 by spring 34, grasping pawl 118 engages the proximal portion 136a of actuation shaft 38 defining slot 136 to retain movable handle in an intermediate position between the non-compressed and compressed positions. It is noted that spring 34 is a light spring which cannot move actuation shaft 38 (and control rod 52) proximally because of friction associated with components of SULU 500. However, a surgeon can manipulate movable handle 22 by moving handle 22 in the direction indicated by arrow "E" in FIG. 62 to move actuation shaft 38 in the direction indicated by arrow "B" and, thus, move SULU 500 (FIG. 1) to the unclamped position (FIG. 3). Because vertical pawl 54 is retained in its retracted position by distal link 108, actuation shaft 38 is permitted to move proximally. Movable handle 22 is prevented from moving to the fully non-compressed position by engagement of grasping pawl 118 with proximal portion 136a of slot 136. This prevents movable handle 22 from retracting distal link 108 to a position to disengage stepped portion 108a of distal link 108 from cam surface 110 of vertical pawl 54. Thus, vertical pawl 54 remains disengaged from actuation shaft 38 and, thus, handle assembly 12 remains in the grasper mode.

Referring to FIGS. 67-74, when movable handle 22 is moved to the compressed position and actuator button 28 is moved from the centered position to the off-center position, handle assembly 12 is transitioned to the firing mode. More specifically, when movable handle 22 is moved to the compressed position and actuator button 28 is moved from the centered position to the off-center position, V-shaped cam member 130 engages lower cam surface 116b on pawl arm 116 to retract pawl arm 116 in the direction indicated by arrow "F" within recess 120 (FIG. 68) of movable handle 22 and retract grasping pawl 118 from within slot 136 of actuation shaft 38. When grasping pawl 118 is removed from slot 136, biasing member 34 (FIG. 61) returns movable handle 22 in the direction indicated by arrow "G" in FIG. 73 to its fully non-compressed position. When this occurs, distal link 108 is pulled proximally by movable handle 22, disengaging stepped portion 108a of distal link 108 from cam surface 110 of vertical pawl 54. Vertical pawl 54 is moved by biasing member 56 into engagement with cutout 58 in actuation shaft 38 to prevent proximal movement of actuation shaft 38, i.e., to prevent retraction of actuation shaft 38 back to its initial position. As such, control rod 52 (FIG. 60), rotary coupler 620 (FIG. 63), and drive bar 591 (FIG. 63) are also inhibited from returning proximally to their respective initial positions. Thus, as shown in FIG. 74, when movable handle 22 is again moved to the compressed position, driving pawl 42 (FIG. 61) engages toothed rack 40 of actuation shaft 38 to advance actuation shaft 38 further distally, e.g., another 15 mm increment, thus advancing control rod 52 (FIG. 60), rotary coupler 620 (FIG. 63), and drive bar 591 (FIG. 63) another increment to at least partially fire SULU 500 (FIG. 1). As actuation shaft 38 is moved distally, vertical pawl 54 and grasping pawl 118 ratchet or slide over toothed rack 40 of actuation shaft 38.

With reference to FIGS. 74-80, as mentioned above, when movable handle 22 is moved to the compressed position with handle assembly 12 in the firing mode (see FIG. 74), driving pawl 42 (FIG. 61) engages toothed rack 40 of actuation shaft 38 to advance actuation shaft 38 to advance control rod 52 (FIG. 60) distally an additional increment. With fire and reload assembly 600 disposed in the firing mode, as control rod 52 is advanced distally the additional increment, rotary coupler 620 is likewise incrementally translated distally. This distal translation of rotary coupler 620, in turn, effects distal translation of drive bar 591 since block protrusions 622 of rotary coupler 620 are received within opposed cut-outs 683, 684 of drive bar 591. More specifically, drive bar 591 is advanced distally an additional increment relative to lock ring 650, rotating lock ring 650 to the first position, thus inhibiting translation of reload bars 660, 670 and permitting advancement of drive bar 591 therethrough.

As drive bar 591 is advanced this distal increment, cam bars 595, which are coupled to drive bar 591, are also advanced distally the length of the increment, e.g., about 15 mm. As such, cam wedges 596 of cam bars 595 are eventually translated into contact with the proximal-most pushers 580 of conveyors 540, 550. As cam wedges 596 of cam bars 595 contact the proximal-most pushers 580, the proximal-most pushers 580 are urged partially from the conveyor links 566 on the lower portions of conveyors 540, 550 into the conveyor links 566 disposed on the upper, tissue-contacting surfaces 570, 556 of conveyors 540, 550, respectively, to an intermediate position wherein the proximal-most pushers 580 are partially disposed within each of the upper and lower conveyor links 566. In one embodiment, the proximal-most conveyor links 566 do not include staples "S" disposed therein, as shown in FIGS. 65-66, such that no staples "S" are fired at this point. The translation of proximal-most pushers 580 to the intermediate position, wherein the proximal-most pushers 580 are partially disposed within each of the upper and lower conveyor links 566, locks conveyors 540, 550 from rotating, thus ensuring that proper positioning of conveyor links 566 is maintained during subsequent the firing operation(s).

Figure 72:
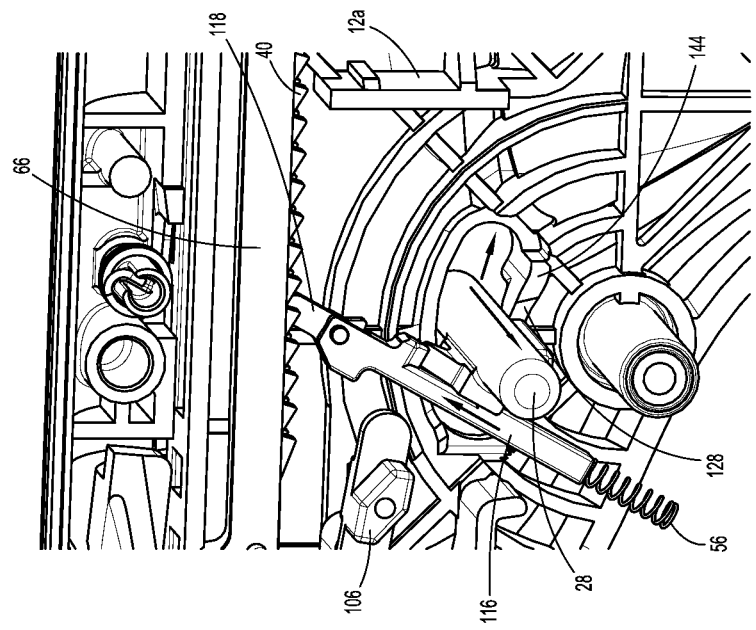
FIG. 72 is a longitudinal, cross-sectional view of the actuation assembly in the firing mode wherein the movable handle has been released from the compressed position.
Figure 71:
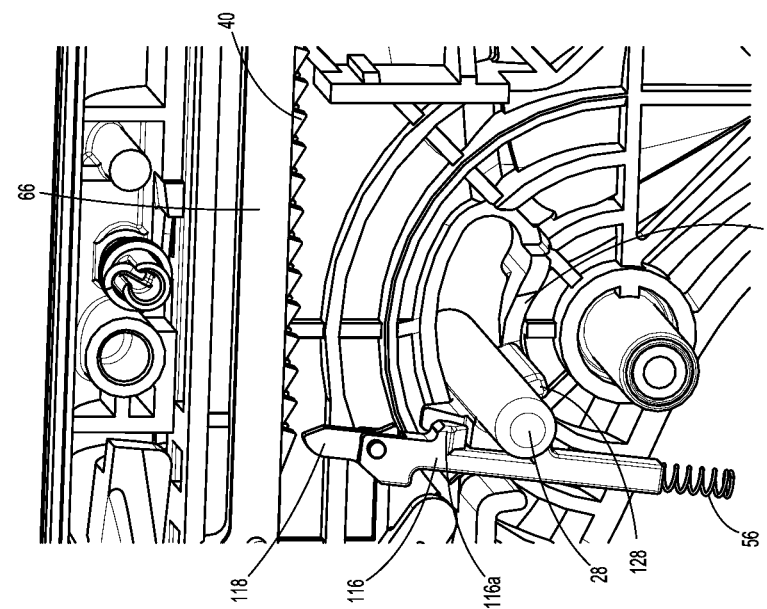
FIG. 71 is a longitudinal, cross-sectional view of the actuation assembly in the firing mode wherein the movable handle is in the compressed position.
Figure 73:
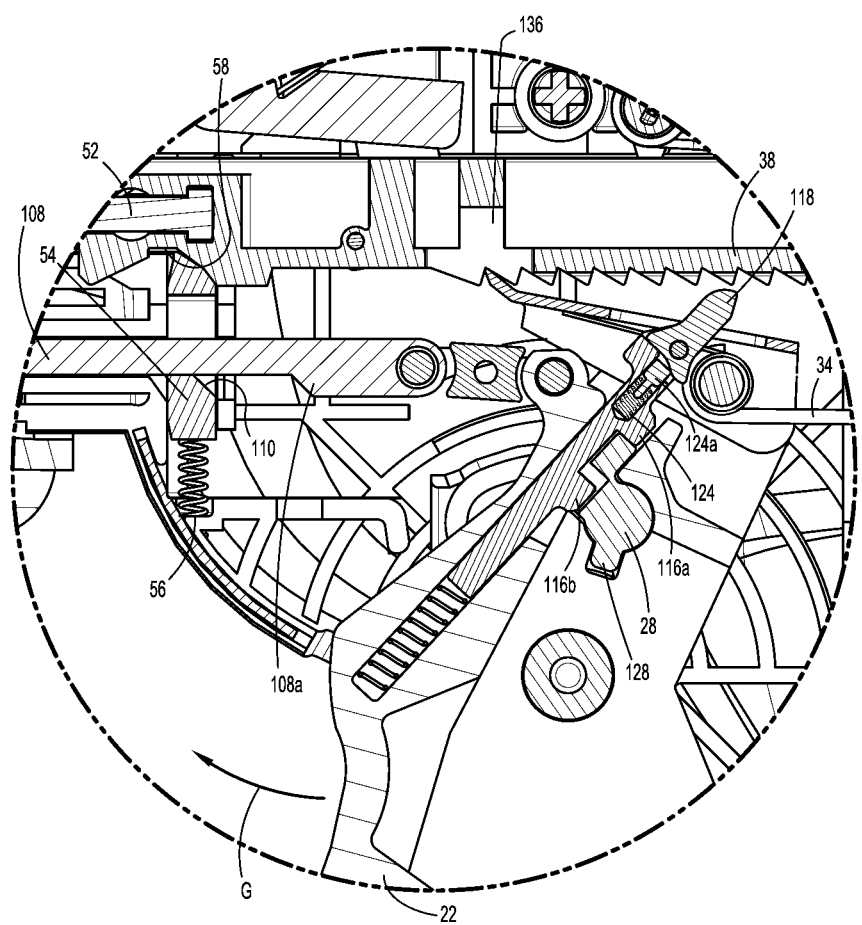
FIG. 73 is a longitudinal, cross-sectional view of the actuation assembly in the firing mode with the movable handle returning towards the original position.

Referring to FIG. 72, when actuator button 28 has been actuated and is in its off-center position, i.e., when handle assembly 12 (FIG. 1) is in the firing mode, linear rib 128 is moved to a position to engage a cam surface 144 positioned on an inner wall of housing section 12a. Cam surface 144 includes an angled face which is positioned to engage linear rib 128 when movable handle 22 (FIG. 67) returns to its non-compressed position to return actuator button 28 to its centered position. The interaction of upper cam surface 116a and V-shaped cam member 130 also urges actuator button 28 to its centered position. When this occurs, pawl arm 116 and grasping pawl 118 return to their extended positions. Since actuation shaft 38 has been advanced distally and grasping pawl 118 is not aligned with slot 136 of actuation shaft 38, movable handle 22 is returned to its non-compressed position after each actuation stroke of movable handle 22.

Upon subsequent compression of movable handle 22, control rod 52, rotary coupler 620, and drive bar 591 are translated distally an additional increment. As drive bar 591 is advanced this additional increment, e.g., another 15 mm, cam wedges 596 of drive bar are urged into contact with pushers 580 disposed within conveyor links 566 on the lower portions of conveyors 540, 550. The angled surfaces defining cam wedges 596 cam along angled surfaces 584 of pushers 580 as cam bars 595 are urged further distally such that pushers 580 are urged upwardly into conveyor links 566 forming the upper tissue-contacting surface of cartridge assembly 614 to eject staples "S." Slightly delayed behind advancement of cam bars 595, dynamic clamping member 593 is advanced through channel 574 to divide tissue between conveyors 540, 550. As can be appreciated, this incremental (15 mm) advancement of drive bar 591 fires only those staples "S" from the next most-proximal group of conveyor links 566 and cuts only the tissue adjacent those conveyor links 566. Subsequent compression(s) of movable handle 22 incrementally advances drive bar 591 further distally (in 15 mm increments) such that additional groups of staples "S" are ejected from their respective conveyor links 566 and such that additional portions of tissue are cut. Thus, depending on the length of the staple line, e.g., 15 mm, 30 mm, 45 mm, etc., several compressions and returns of movable handle 22 may be required to fully fire SULU 500 for stapling and dividing the entire portion of tissue grasped between anvil assembly 506 and cartridge assembly 514. Handle assembly 12 may alternatively be configured such that SULU 500 is fully fired to eject staples "S" and cut tissue upon a single compression of movable handle 22.

After SULU 500 has been fully fired, i.e., at the end of the full firing stroke of drive bar 591, rotary coupler 620 contacts toothed proximal portion 642 of distal cam 640 and is partially rotated relative to distal cam 640 due to the engagement of the respective teeth thereof.

With reference to FIGS. 81-86, retraction knobs 26 (FIG. 36) are translated proximally once SULU 500 has been fully fired to translate control rod 52 and, thus, rotary coupler 620 of fire and reload assembly 600 proximally. More specifically, rotary coupler 620 is moved proximally upon retraction of retraction knobs 26 (FIG. 36) such that toothed proximal portion 627 of rotary coupler 620 ultimately contacts toothed distal portion 632 of proximal cam 630 causing rotary coupler 620 to rotate from the partially rotated position to a position in which drive bar 591 is disengaged from rotary coupler 620 and reload bars 660, 670 are engaged to rotary coupler 620. This position corresponds to the reload mode of fire and reload assembly 600.

Figure 87:
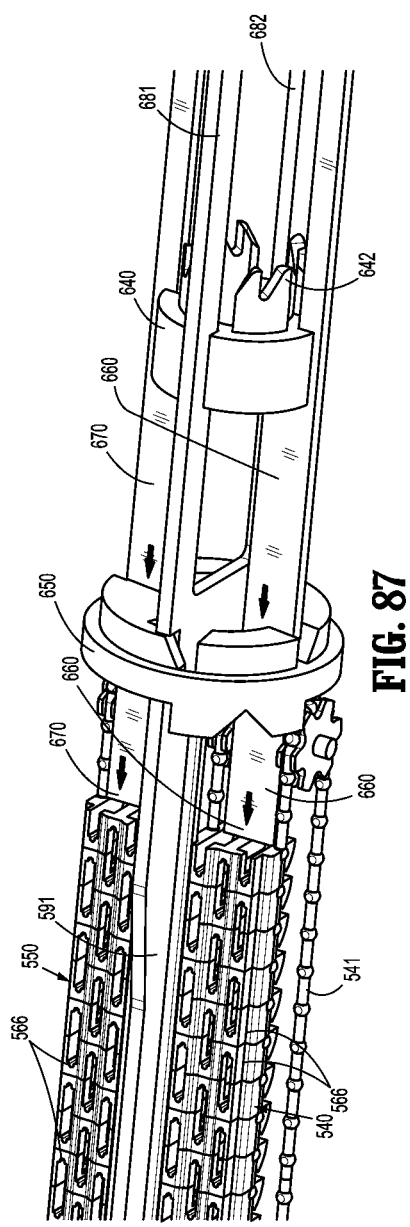
FIG. 87 is a top, perspective view of a portion of the conveyor assembly and a portion of the fire and reload assembly during reloading of the SULU.
Figure 88:
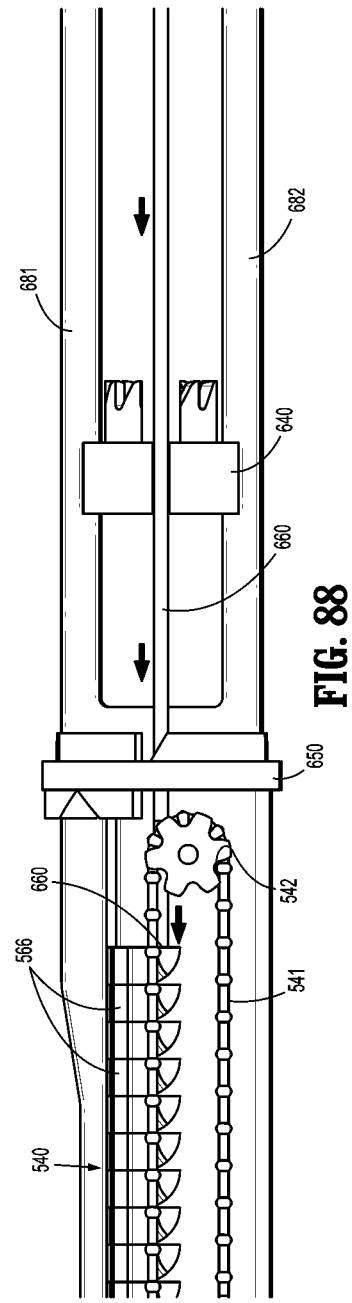
FIG. 88 is a longitudinal, cross-sectional view of a portion of the conveyor assembly and a portion of the fire and reload assembly during reloading of the SULU.

Referring additionally to FIGS. 87-91, with fire and reload assembly 600 now in the reload mode, wherein reload bars 660, 670 are engaged to rotary coupler 620, movable handle 22 (FIG. 36) may be compressed once again to reload SULU 500 such that a new set of conveyor links 566 form the upper, tissue-contacting surface of cartridge assembly 514. In order to reload SULU 500, movable handle 22 (FIG. 36) is compressed a first time to advance control bar 52 and rotary coupler 620 distally one increment. As rotary coupler 620 is advanced distally, reload bars 660, 670, which are coupled to rotary coupler 620 in the reload mode, are likewise translated distally one increment. As reload bars 660, 670 are translated this initial increment, reload bars 660, 670 are translated distally through lock ring 650, thus rotating lock ring 650 to the second position to inhibit translation of drive bar 591. Upon subsequent compression (s) of movable handle 22, reload bars 660, 670 are incrementally translated further distally such that reload bars 660, 670 contact the proximal ends of the proximal-most conveyor links 566 that form the upper, tissue-contacting surface of cartridge assembly 514 and urge conveyor links 566 distally such that conveyors 540, 550 are rotated about proximal and distal sprockets 542, 552 and 544, 554, respectively. Eventually, upon a sufficient number of compressions of movable handle 22, conveyors 540, 550 are rotated such that a new set of conveyor links 566 is positioned to form the upper, tissue-contacting surface of cartridge assembly 514, while the conveyor links 566 (which now include pushers 580 disposed therein and which supported the previously fired staples) are rotated about distal sprockets 544, 554 to the lower portion of cartridge assembly 514, as best shown in FIGS. 87-89. As can be appreciated, once pushers 580 are disposed on the lower portion of cartridge assembly 514, and with a new set of conveyor links 566 disposed on the upper portion of cartridge assembly 514, cartridge assembly 514 is fully reloaded for subsequent use.

Figure 90:
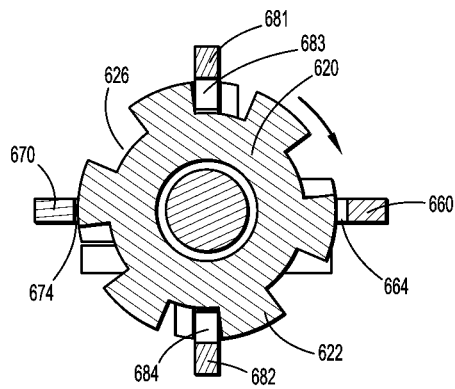
FIG. 90 is a transverse, cross-sectional view of the fire and reload assembly shown partially rotated from the reload mode towards the firing mode.
Figure 91:
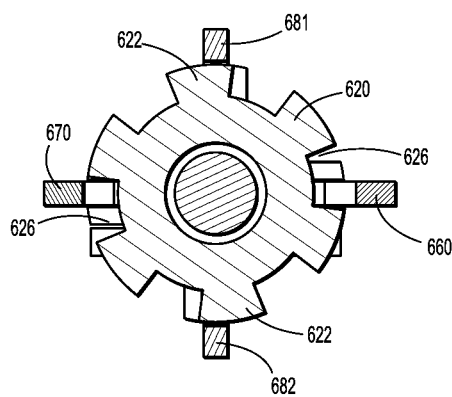
FIG. 91 is a transverse, cross-sectional view of the fire and reload assembly shown in the firing mode.

Referring still to FIGS. 87-91 and in particular to FIG. 90, as the full reload stroke of reload bars 660, 670 has been achieved to rotate a new set of conveyor links 566 into position to form the upper, tissue-contacting surface of cartridge assembly 514, rotary coupler 620 contacts toothed proximal portion 642 of distal cam 640 and is partially rotated relative to distal cam 640 due to the engagement of the respective teeth thereof. Thereafter, upon full retraction of rotary coupler 620, e.g., via retraction of retraction knobs 26 (FIG. 1), rotary coupler 620 is pulled proximally such that toothed proximal portion 627 of rotary coupler 620 ultimately contacts toothed distal portion 632 of proximal cam 630, causing rotary coupler 620 to rotate from the partially rotated position to a position in which reload bars 660, 670 are disengaged from rotary coupler 620 and drive bar 591 is engaged to rotary coupler 620. This position corresponds to the firing mode of fire and reload assembly 600. As can be appreciated, with fire and reload assembly 600 once again disposed in the firing mode, and with conveyors 540, 550 rotated to position a new set of staple-containing conveyor links 566 on the upper surface of cartridge assembly 514, stapler 10 may be operated similarly as described above to fire a second, third, etc. set of staples "S."

Although described with respect to a releasable SULU 500, it is envisioned that surgical stapler 10 may also formed with an integrated tool assembly. More specifically, the cartridge and anvil assemblies, i.e., the tool assembly, may be integrally formed with elongated body portion 18 of stapler 10 such that, for example, conveyors 540, 550 may define an increased length to permit a greater number of firing/reloading operations. Stapler 10 may also be adapted for use in conjunction with open surgical procedures (as opposed to endoscopic procedures). It is also envisioned that stapler 10 be configured to be operated, e.g., fired and reloaded, robotically, or via any other suitable system or mechanism, rather than being operable via actuation of handle assembly 12.

Finally, it is also envisioned that mechanisms other than a conveyor assembly may be provided to effect reloading of the stapler. For example, a rotatable barrel assembly is envisioned. The rotatable barrel assembly may include a rotatable barrel defining a longitudinal axis and including a plurality of longitudinal rows, or sets of links (similar to conveyor links 566) that are engaged to the rotatable barrel at various equally-spaced radial positions, e.g., 0 degrees (wherein the links form a tissue-contacting surface), 90 degrees, 180 degrees, and 270 degrees. In such an embodiment, a drive bar may be advanced through the rotatable barrel to eject the staples from those links forming the tissue-contacting surface. Thereafter, the barrel may be rotated about the longitudinal axis to position a new set of links to form the tissue-contacting surface (i.e., to rotate a new set of links to the 0 degree position) for subsequent firing.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A method of surgery, comprising:
effecting a first actuation of a surgical stapling apparatus to fire a first plurality of staples through tissue clamped between an anvil assembly and a cartridge assembly of the surgical stapling apparatus;
decoupling at least one firing component;
coupling at least one reloading component;
effecting a second actuation of the surgical stapling apparatus to move a second plurality of staples into a firing position within the cartridge assembly;
decoupling the at least one reloading component;
coupling the at least one firing component; and
effecting a third actuation of the surgical stapling apparatus to fire the second plurality of staples through tissue clamped between the anvil assembly and the cartridge assembly.

2. The method according to claim 1, wherein effecting the first actuation includes moving a movable handle in relation to a stationary handle through a first actuation stroke for clamping tissue between the anvil assembly and the cartridge assembly, and moving the movable handle in relation to the stationary handle through at least one second actuation stroke for firing the first plurality of staples.

3. The method according to claim 2, wherein the movable handle is moved in relation to the stationary handle through a plurality of second actuation strokes for incrementally firing the first plurality of staples.

4. The method according to claim 2, wherein moving the movable handle in relation to the stationary handle through each of the first actuation stroke and the at least one second actuation stroke includes moving the movable handle in relation to the stationary handle from an un-compressed position to a compressed position.

5. The method according to claim 4, wherein effecting the first actuation further includes actuating an actuator button when the movable handle is disposed in the compressed position relative to the stationary handle after the first actuation stroke and before the at least one second actuation stroke.

6. The method according to claim 4, wherein the movable handle is returned from the compressed position to the un-compressed position in relation to the stationary handle after the first actuation stroke and before the at least one second actuation stroke.

7. The method according to claim 6, wherein the movable handle is returned from the compressed position to the un-compressed position in relation to the stationary handle after each of the at least one second actuation strokes.

8. The method according to claim 1, wherein the at least one firing component includes a drive bar, and wherein effecting the first actuation includes advancing the drive bar relative to the cartridge assembly to fire the first plurality of staples.

9. The method according to claim 8, wherein the at least one reloading component includes a reload bar, and wherein effecting the second actuation includes advancing the reload bar relative to the cartridge assembly to move the second plurality of staples into the firing position.

10. The method according to claim 9, wherein decoupling the at least one firing component includes decoupling a movable handle from the drive bar, and wherein coupling the at least one reloading component includes coupling the movable handle to the reload bar after the first actuation and before the second actuation.

11. The method according to claim 9, wherein effecting the third actuation advances the drive bar relative to the cartridge assembly to fire the second plurality of staples.

12. The method according to claim 11, wherein decoupling the at least one reloading component includes decoupling a movable handle from the reload bar, and wherein coupling the at least one firing component includes coupling the movable handle to the drive bar after the second actuation and before the third actuation.

13. The method according to claim 1, wherein effecting the second actuation includes moving a movable handle in relation to a stationary handle through at least one actuation stroke for moving the second plurality of staples into the firing position.

14. The method according to claim 13, wherein the movable handle is moved in relation to the stationary handle through a plurality of actuation strokes for incrementally moving the second plurality of staples into the firing position.

15. The method according to claim 1, wherein effecting the third actuation includes moving a movable handle in relation to a stationary handle through a first actuation stroke for clamping tissue between the anvil assembly and the cartridge assembly, and moving the movable handle in relation to the stationary handle through at least one second actuation stroke for firing the second plurality of staples.

16. The method according to claim 15, wherein moving the movable handle in relation to the stationary handle through each of the first actuation stroke and the at least one second actuation stroke includes moving the movable handle in relation to the stationary handle from an un-compressed position to a compressed position.

17. The method according to claim 16, wherein effecting the third actuation further includes actuating an actuator button when the movable handle is disposed in the compressed position relative to the stationary handle after the first actuation stroke and before the at least one second actuation stroke.

18. The method according to claim 16, wherein the movable handle is returned from the compressed position to the un-compressed position in relation to the stationary handle after the first actuation stroke and before the at least one second actuation stroke.

19. The method according to claim 16, wherein the movable handle is returned from the compressed position to the un-compressed position in relation to the stationary handle after each of the at least one second actuation strokes.

20. The method according to claim 1, further comprising retracting a retraction knob of the surgical stapling apparatus in relation to a housing of the surgical stapling apparatus at least one of between the first and second actuations or between the second and third actuations.

* * * * *